(12) United States Patent
Cruz

(10) Patent No.: US 7,879,793 B2
(45) Date of Patent: Feb. 1, 2011

(54) TREATMENT OF MEDICAL CONDITION WITH A2 DOMAIN OF VON WILLEBRAND FACTOR

(75) Inventor: Miguel A. Cruz, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 211 days.

(21) Appl. No.: 11/874,316

(22) Filed: Oct. 18, 2007

(65) Prior Publication Data

US 2009/0118161 A1 May 7, 2009

Related U.S. Application Data

(60) Provisional application No. 60/852,482, filed on Oct. 18, 2006, provisional application No. 60/890,910, filed on Feb. 21, 2007.

(51) Int. Cl.
*A61K 38/00* (2006.01)
(52) U.S. Cl. .................... 514/1.1; 514/1.4; 514/13.5; 514/13.7; 514/13.8
(58) Field of Classification Search ............... None
See application file for complete search history.

(56) References Cited

U.S. PATENT DOCUMENTS 6,887,474 B1    5/2005   Stewart et al.
2005/0186646 A1   8/2005   Cruz

OTHER PUBLICATIONS

International Preliminary Report on Patentability issued Apr. 22, 2009 (Published Apr. 22, 2009), during the prosecution of International Application No. PCT/US2007/081767.
International Search Report issued Sep. 26, 2008 (published Dec. 18, 2008), during the prosecution of International Application No. PCT/US07/81767.
Written Opinion issued Sep. 26, 2008, during the prosecution of International Application No. PCT/US07/81767.

*Primary Examiner*—Gary B. Nickol
*Assistant Examiner*—Daniel C Gamett
(74) *Attorney, Agent, or Firm*—Fulbright & Jaworski L.L.P.

(57) ABSTRACT

The present invention is directed to methods for the prevention, treatment and/or diagnosis of a medical condition, such as sepsis, systemic inflammatory reaction syndrome, and/or thrombosis, for example. In particular, the method employs part or all of the A2 domain of von Willebrand factor. In certain cases, a recombinant A2 domain is utilized for the treatment of sepsis, systemic inflammatory reaction syndrome, and/or thrombosis, for example.

9 Claims, 26 Drawing Sheets

Exemplary peptides to narrow the N-terminal (half) A2 domain (1481-1605)
1-GLLGVSTLGPKRNSM (SEQ ID NO:16)

2-NSMVLDVAFVLEGSD (SEQ ID NO:17)

3-GSDKIGEADFNRSKE (SEQ ID NO:18)

4-SKEFMEEVIQRMDVG (SEQ ID NO:19)

5-DVGQDSIHVTVLQYS (SEQ ID NO:20)

6-QYSYMVTVEYPFSEA (SEQ ID NO:21)

7-SEAQSKGDILQRVRE (SEQ ID NO:22)

8-VREIRYQGGNRTNTG (SEQ ID NO:23)

9-NTGLALRYLSDHSFL (SEQ ID NO:24)

10-SFLVSQGDREQAPNLVY (SEQ ID NO:25)

FIG. 17

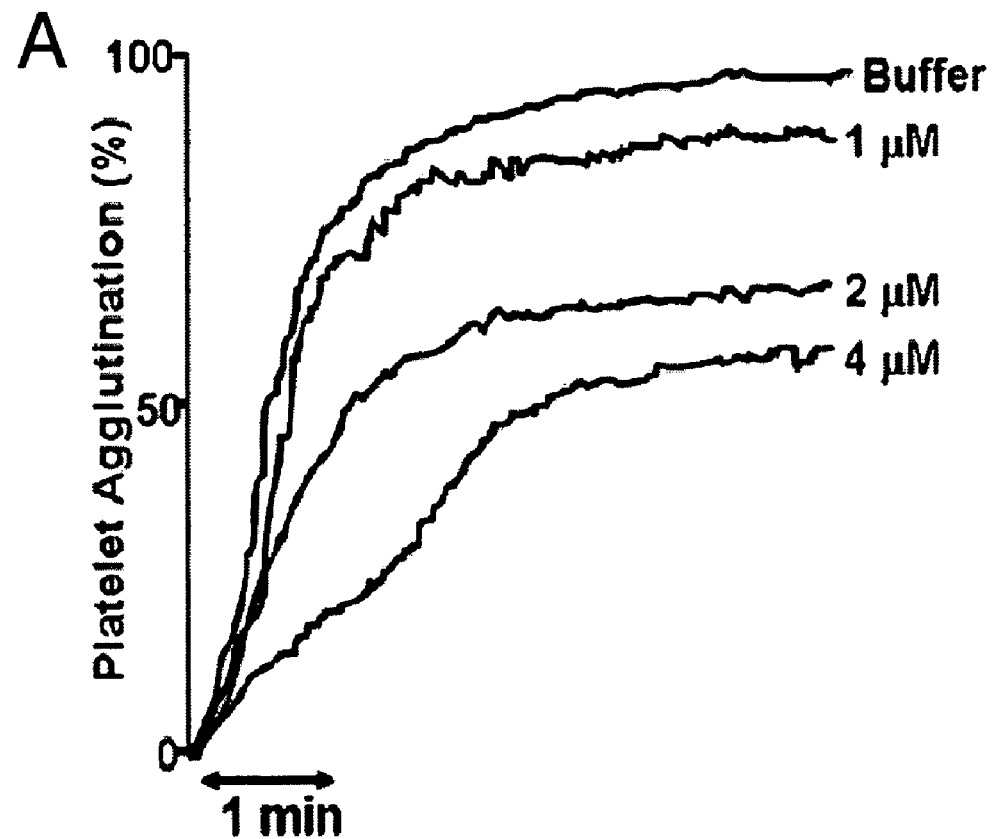
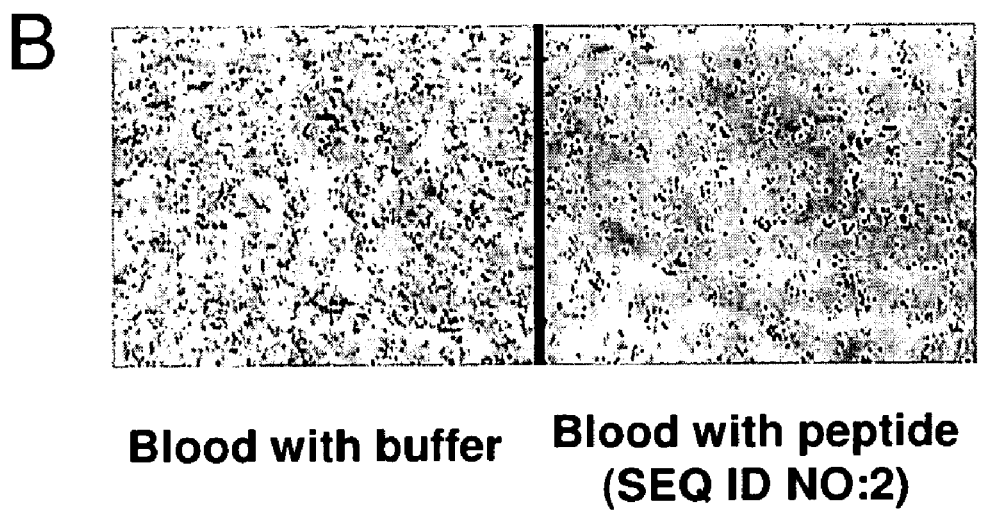
FIG. 23

SEQUENCE LISTING

<160> NUMBER OF SEQ ID NOS: 31

<210> SEQ ID NO 1
<211> LENGTH: 188
<212> TYPE: PRT
<213> ORGANISM: Human

<400> SEQUENCE: 1

Gly Leu Leu Gly Val Ser Thr Leu Gly Pro Lys Arg Asn Ser Met Val
1               5                   10                  15

Leu Asp Val Ala Phe Val Leu Glu Gly Ser Asp Lys Ile Gly Glu Ala
            20                  25                  30

Asp Phe Asn Arg Ser Lys Glu Phe Met Glu Glu Val Ile Gln Arg Met
        35                  40                  45

Asp Val Gly Gln Asp Ser Ile His Val Thr Val Leu Gln Tyr Ser Tyr
    50                  55                  60

Met Val Thr Val Glu Tyr Pro Phe Ser Glu Ala Gln Ser Lys Gly Asp
65                  70                  75                  80

Ile Leu Gln Arg Val Arg Glu Ile Arg Tyr Gln Gly Gly Asn Arg Thr
                85                  90                  95

Asn Thr Gly Leu Ala Leu Arg Tyr Leu Ser Asp His Ser Phe Leu Val
            100                 105                 110

Ser Gln Gly Asp Arg Glu Gln Ala Pro Asn Leu Val Tyr Met Val Thr
        115                 120                 125

Gly Asn Pro Ala Ser Asp Glu Ile Lys Arg Leu Pro Gly Asp Ile Gln
    130                 135                 140

Val Val Pro Ile Gly Val Gly Pro Asn Ala Asn Val Gln Glu Leu Glu
145                 150                 155                 160

Arg Ile Gly Trp Pro Asn Ala Pro Ile Leu Ile Gln Asp Phe Glu Thr
                165                 170                 175

Leu Pro Arg Glu Ala Pro Asp Leu Val Leu Gln Arg
            180                 185

<210> SEQ ID NO 2
<211> LENGTH: 125
<212> TYPE: PRT
<213> ORGANISM: Human

<400> SEQUENCE: 2

Gly Leu Leu Gly Val Ser Thr Leu Gly Pro Lys Arg Asn Ser Met Val
1               5                   10                  15

Leu Asp Val Ala Phe Val Leu Glu Gly Ser Asp Lys Ile Gly Glu Ala
            20                  25                  30

Asp Phe Asn Arg Ser Lys Glu Phe Met Glu Glu Val Ile Gln Arg Met
        35                  40                  45

Asp Val Gly Gln Asp Ser Ile His Val Thr Val Leu Gln Tyr Ser Tyr
    50                  55                  60

Met Val Thr Val Glu Tyr Pro Phe Ser Glu Ala Gln Ser Lys Gly Asp
65                  70                  75                  80

```
Ile Leu Gln Arg Val Arg Glu Ile Arg Tyr Gln Gly Gly Asn Arg Thr
                85                  90                  95

Asn Thr Gly Leu Ala Leu Arg Tyr Leu Ser Asp His Ser Phe Leu Val
            100                 105                 110

Ser Gln Gly Asp Arg Glu Gln Ala Pro Asn Leu Val Tyr
        115                 120                 125

<210> SEQ ID NO 3
<211> LENGTH: 63
<212> TYPE: PRT
<213> ORGANISM: Human

<400> SEQUENCE: 3

Met Val Thr Gly Asn Pro Ala Ser Asp Glu Ile Lys Arg Leu Pro Gly
1               5                   10                  15

Asp Ile Gln Val Val Pro Ile Gly Val Gly Pro Asn Ala Asn Val Gln
            20                  25                  30

Glu Leu Glu Arg Ile Gly Trp Pro Asn Ala Pro Ile Leu Ile Gln Asp
        35                  40                  45

Phe Glu Thr Leu Pro Arg Glu Ala Pro Asp Leu Val Leu Gln Arg
    50                  55                  60

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gacagttacc cccaacctga                                          20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tggatgtcag catcttcctg                                          20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
agccaacagg aaccattgac                                          20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcttcctgca catcttcctc                                          20
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aagccaatat agggcctcgt                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctcagcaaat gggctttctc                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aggggagatt cagtgtggtg                                               20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cgaccacttt gtcaagctca                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggcagtttca tcattgctgg                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttgaacgcct caggtgattc                                               20

<210> SEQ ID NO 14
<211> LENGTH: 22
<212> TYPE: DNA
<213> ORGANISM: Artificial Sequence
<220> FEATURE:
<223> OTHER INFORMATION: Primer
```

```
<400> SEQUENCE: 14 tccccctcggc ttacagctaa tg                                           22

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tggtactcgc agttggctct gaag                                          24

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Gly Leu Leu Gly Val Ser Thr Leu Gly Pro Lys Arg Asn Ser Met
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Asn Ser Met Val Leu Asp Val Ala Phe Val Leu Glu Gly Ser Asp
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Gly Ser Asp Lys Ile Gly Glu Ala Asp Phe Asn Arg Ser Lys Glu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Ser Lys Glu Phe Met Glu Glu Val Ile Gln Arg Met Asp Val Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Asp Val Gly Gln Asp Ser Ile His Val Thr Val Leu Gln Tyr Ser
```

-continued

```
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

```
Gln Tyr Ser Tyr Met Val Thr Val Glu Tyr Pro Phe Ser Glu Ala
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 22

```
Ser Glu Ala Gln Ser Lys Gly Asp Ile Leu Gln Arg Val Arg Glu
1               5                   10                  15
```

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

```
Val Arg Glu Ile Arg Tyr Gln Gly Gly Asn Arg Thr Asn Thr Gly
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 24

```
Asn Thr Gly Leu Ala Leu Arg Tyr Leu Ser Asp His Ser Phe Leu
1               5                   10                  15
```

<210> SEQ ID NO 25
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 25

```
Ser Phe Leu Val Ser Gln Gly Asp Arg Glu Gln Ala Pro Asn Leu Val
1               5                   10                  15

Tyr
```

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 26

```
Ser Lys Gly Asp Ile Leu Gln Arg Val Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Ile Leu Gln Arg Val Arg Glu Ile Arg Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Val Arg Glu Ile Arg Tyr Gln Gly Gly Asn
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Ile Gly Glu Ala Asp Phe Asn Arg Ser Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

His Val Thr Val Leu Gln Tyr Ser Tyr Met
1               5                   10

<210> SEQ ID NO 31
<211> LENGTH: 564
<212> TYPE: DNA
<213> ORGANISM: Human

<400> SEQUENCE: 31
gggctcttgg gggtttcgac cctggggccc aagaggaact ccatggttct ggatgtggcg      60
ttcgtcctgg aaggatcgga caaaattggt gaagccgact tcaacaggag caaggagttc     120
atggaggagg tgattcagcg gatgatgtg ggccaggaca gcatccacgt cacggtgctg      180
cagtactcct acatggtgac tgtggagtac cccttcagcg aggcacagtc caaaggggac     240
atcctgcagc gggtgcgaga gatccgctac cagggcggca acaggaccaa cactgggctg     300
gccctgcggt acctctctga ccacagcttc ttggtcagcc agggtgaccg ggagcaggcg     360
```

```
-continued cccaacctgg tctacatggt caccggaaat cctgcctctg atgagatcaa gaggctgcct    420
ggagacatcc aggtggtgcc cattggagtg ggccctaatg ccaacgtgca ggagctggag    480
aggattggct ggcccaatgc ccctatcctc atccaggact ttgagacgct cccccgagag    540
gctcctgacc tggtgctgca gagg                                          564
```

TREATMENT OF MEDICAL CONDITION WITH A2 DOMAIN OF VON WILLEBRAND FACTOR

The present application claims priority to U.S. Provisional Patent Application Ser. No. 60/852,482, which was filed Oct. 18, 2006, and to U.S. Provisional Patent Application Ser. No. 60/890,910, which was filed on Feb. 21, 2007, both applications of which are incorporated by reference herein in their entirety.

STATEMENT REGARDING FEDERALLY SPONSORED RESEARCH OR DEVELOPMENT

The present invention utilized funds from National Institutes of Health (NIH) grant HL72886. The United States Government has certain rights in the invention.

FIELD OF THE INVENTION

The present invention is related at least to the fields of medicine, molecular biology, and cell biology. The invention is directed to methods to treat, diagnose and/or prevent medical conditions, such as sepsis or thrombosis, utilizing aspects of the A2 domain of von Willebrand factor.

BACKGROUND OF THE INVENTION

Sepsis

Sepsis is a systemic inflammatory response to an infection or insult (Aird, 2003; Dremsizov et al., 2004). Severe sepsis is a serious public health concern in the United States. It is a common diagnosis among critically ill patients and carries a high mortality rate. However, the pathophysiology of sepsis is not well understood (Riedemann et al., 2003) and afflicted patients deteriorate rapidly as a result of the progressive failure of multiple organs. The bulk of recent investigations suggest that it results from uncontrolled responses of the immune and inflammatory systems that are clinically manifested by an acute systemic inflammatory reaction syndrome (SIRS) (Tetta et al., 2005). In sepsis, hyperactivation of the immune response leads to the excessive production of various proinflammatory cytokines and cellular injury (Pinsky, 2004).

LPS

Sepsis can be caused by a non-infectious or infectious insult, including Lypolysaccharide (LPS or endotoxin). LPS is a component of the outer cell membrane of Gram-negative bacteria that can initiate a parallel cascade of events that contribute to the clinical manifestations of sepsis (Alexander and Riestschel, 2001; Dauphinee and Karsan, 2006). For example, in vitro and in vivo studies have shown that LPS interact with cells of the immune system through antigen recognition pattern and with inflammatory cells such as leukocytes, platelets and endothelial cells. Interaction between the cells of the immune and inflammatory systems leads to several responses including the activation of downstream signaling pathways that promote posttranscriptional changes in cell function; up-regulation of cell adhesion molecules that promote interaction between endothelial cells leukocytes and platelets; and increased expression of procoagulants. These responses are maintained by a continuous recruitment and activation of leukocytes and platelets to the site of endothelial injury. One of the consequences is the formation of microthrombi. The endothelium shifts from an anticoagulant surface to a procoagulant surface. Activated endothelium expresses tissue factor, releases Von Willebrand factor (VWF), decreases the expression of endothelial protein C receptor (EPCR) and natural anticoagulants such as thrombomodulin (TM) (Li et al., 2005; Iwaki et al., 2005). Endothelial cells (EC) are also greatly responsible for an uncontrolled inflammatory response (Aird, 2003; Peters et al., 2003; Chen and Lopez, 2005). They can be activated directly by LPS or by a number of other mechanisms observed in patients with sepsis such as complement, cytokines, chemokines, coagulation factors, fibrin, activated platelets and activated leukocytes. The result is a self feeding enhancement of the inflammatory response that if uncontrolled becomes irreversible. The clinical manifestation is a rapid deterioration of the patient with progressive failure of multiple target organs and death (Guidet et al., 2005; O'Brien et al., 2005). There are several markers of endothelial cell activation (Meisner, 2005), VWF being one of the most used (Schorer et al., 1987).

VWF

Mature VWF consists of a 2,050-residue polypeptide that contains multiple copies of A, B, C and D type domains, arranged in the order D'-D3-A1-A2-A3-D4-B1-B2-B3-C1-C2-CK (cystine knot) (FIG. 1) (Bonthron et al., 1986; Verweij et al., 1986). Pro-VWF subunits dimerize through disulfide bonds near their carboxyl termini. These pro-VWF dimers form disulfide bond between N-terminal D3 domains and C-terminal CK domains, generating VWF multimers that may contain more than 80 subunits and exceed 20 million daltons (Girma et al., 1987). VWF is synthesized and secreted by endothelial cells into plasma and the vascular subendothelium (Sussman and Rand, 1982). VWF is also stored in and secreted from the α-granules of megakaryocytes and platelets (Nachman et al., 1977). VWF has a significant physiological relevance in hemostasis, thrombosis and inflammation. It interacts with coagulation factor VIII, platelet glycoproteins (GP) Ib/IX, GPIIb/IIIa, fibrin, and collagen (Koppelman et al., 1996; Beacham et al., 1992; Keuren et al., 2004).

As shown in FIG. 1, the central portion of the VWF subunit contains a triplicate repeat sequence, or A domain, that has been identified in other proteins (Whittaker and Hynes, 2002). Investigators have established that the VWF-A1 domain contains binding sites for GPIb/IX, heparin, cell surface sulfatides and collagen types I, III and VI (Vasudevan et al., 2000; Cruz et al., 1993; Perrault et al., 1999; Sobel et al., 1992; Christophe et al., 1991; Borthakur et al., 2003; Mazzucato et al., 1999; Hoylaerts et al., 1997; Morales et al., 2006). Furthermore, investigators have established that the highly homologous VWF-A3 domain, which does not interact with platelets, binds to collagen fibrils, types I and III (Cruz et al., 1995; Lankhof et al., 1996).

The A2 Domain of VWF

The VWF-A2 domain (amino acid residues 1480-1673) (Verweij et al., 1986; Bonthron et al., 1986), is functionally important because it contains the cleavage site for the enzyme ADAMTS-13, a metalloproteinase that controls the size of VWF multimers. In an inflammatory environment, endothelial cells secrete ultralarge multimers of VWF (ULVWF) that constitutively bind platelet GPIb (Moake, 2002) and proficiently recruit platelets to the site of endothelial injury. ADAMTS-13 limits the size of the VWF multimers and prevents spontaneous formation of microthrombi (Fujikawa et al., 2001; Zheng et al., 2001). The site of cleavage is located between the residues Y1605 and M1606 of the A2 domain, (Furlan et al., 1996; Tsai, 1996). Very recently, investigators have expressed in bacteria the VWF-A2 domain for use as a substrate in assays to measure the activity of ADAMTS-13 in plasma (Cruz et al., 2003; Kokame et al., 2004; Whitelock et al., 2004).

VWF and Microvascular Thrombosis

Under healthy conditions VWF is constitutively secreted as high molecular weight multimers into plasma or subendothelium. However, in conditions associated with SIRS, such as in endotoxemia, endothelial cells are activated and release ULVWF from intracellular storage granules (i.e. Weibel-Palade bodies)(van Mourik et al., 2002). As mentioned earlier, ULVWF multimers make a strong bond with the platelet receptor GPIbα, facilitating local accumulation of platelets and formation of thrombi (Dong et al., 2002; Arya et al., 2002).

The release of ULVWF can be induced on human umbilical vein endothelial cells (HUVEC) by a variety of factors that are present in sepsis such as inflammatory cytokines, thrombin, histamine, leukocyte elastase, high shear, hypoxia and endotoxin (LPS) (Aird, 2003; Dong et al., 2002; Gimbrone et al., 2000; Zeuke et al., 2002). In fact, a study showed that inflammatory cytokines such as interleukin (IL)-8 and tumor necrosis factor-alpha (TNFα), induced the release of ULVWF (Bernardo et al., 2004). This newly secreted ULVWF binds to platelets, activating more platelets that in turn activate the endothelial cells. This process, together with the activation of the coagulation cascade, leads to the generation of thrombin and the formation of fibrin. Clinically, these interactions are translated into a thrombotic and hypercoagulable tendency.

The present invention provides novel solutions for long-felt needs in the art to treat medical conditions that are treatable by the A2 domain of VWF, such as sepsis, systemic inflammatory reaction syndrome, and/or thrombosis, for example.

SUMMARY OF THE INVENTION

The present invention concerns the treatment and/or prevention of at least one symptom of sepsis, thrombosis, and/or systemic inflammatory response syndrome in a mammal, and/or the diagnosis of said conditions.

Severe sepsis remains the dominant challenge in the care of critically ill patients. Insufficient development in both medical diagnosis and treatment has led to continued growth in reported cases over the past two decades with little improvement in mortality statistics. Effective treatment early in the course of the disease is critical to reduce complications and avoid mortality. Therefore, the present invention concerns novel compositions and methods at least for the treatment of sepsis. It is demonstrated that in vitro purified A2 domain from VWF blocks the binding of platelet GPIb to the A1 domain in VWF and it inhibits VWF-mediated platelet adhesion to fibrin, indicating that A2 prevents further progression of thrombus formation. In vivo, A2 rescues LPS-treated mice. The animals treated with A2 protein recover quickly and 100% survived compared with controls. Therefore, the inventor has identified a novel therapeutic agent for sepsis. The role of the recombinant VWF-A2 polypeptide attenuating microvascular thrombosis leads to the identification of novel therapeutic targets that would greatly contribute to the treatment of patients with not only sepsis but also those affected with systemic inflammatory reaction syndrome.

In particular embodiments of the invention, the interaction between VWF and fibrin is significant. This interaction facilitates platelet adhesion to fibrin (Keuren et al., 2004; Endenburg et al., 1995). Very recently, the inventor has identified a binding site for fibrin in the A2 domain of VWF. It has also been found that the isolated A2 domain inhibits VWF-mediated platelet adhesion to fibrin under high flow conditions. Thus, the isolated A2 domain inhibits the formation of microthrombi induced by deposited fibrin, in certain embodiments of the invention. To further characterize this aspect of the invention, the protein was tested in vivo and under inflammatory conditions where large amounts of ULVWF are released by the endothelium. It was observed that systemic administration of the A2-domain of VWF had a beneficial effect in mice treated with LPS. Interestingly, the A2-domain led to a complete recovery of the LPS-treated animals with 100% survival compared with controls. Preliminary immunohistochemical analyses demonstrated a marked reduction of microvascular thrombi in the liver vasculature. In specific embodiments of the invention, there is further characterization of the biological mechanisms that are set off by the A2-domain of VWF during a state of systemic inflammation.

In particular embodiments of the invention, the interaction between the A2 domain and vimentin is significant. Recently the inventor demonstrated that the A2 domain binds to endothelial cells (EC) and that the specific interaction was between A2 and Vimentin. In some embodiments the interaction is direct, whereas in other embodiments the interaction is indirect. Vimentin is one of the members of the intermediate filaments (IF) in addition to being implicated in critical functions involved in adhesion, migration, and cell signaling (Ivaska et al., 2007). The protective effect of the recombinant A2 domain protein on LPS-treated mice and the novel binding activity of the A2 domain of VWF for vimentin indicates that in some embodiments one of the biological mechanisms by which the A2 protein sets off the recuperation of the sick mice is via an interaction with vimentin. Thus, the A2 domain interaction with vimentin has a role in preventing and/or treating sepsis, in certain aspects. In specific embodiments of the invention, there is further characterization of the biological mechanisms that are set off by the A2-domain of VWF and its interaction with vimentin during a state of systemic inflammation.

In specific embodiments of the invention, the A2 domain used in certain embodiments of the invention comprises a fibrin binding site, a vimentin binding site, the activity to bind endothelial cells, the activity to bind neutrophils, and/or the activity to bind the A1 domain of VWF, for example. The A2 domain may comprise one or more alpha helices and/or one or more beta sheets. In certain aspects of the invention, the A2 domain comprises a peptide. The peptide may be of any suitable size, and in specific aspects the peptide is 4, 5, 6, 7, 8, 9, 10, 11, 12, 13, 14, 15, 16, 17, 18, 19, 20, 21, 22, 23, 24, 25, 26, 27, 28, 29, or 30 or more amino acids in length. The peptide may also be any combination and/or mixture of said peptides.

In particular embodiments of the invention, the A2 domain is delivered to an individual for the prevention and/or treatment of sepsis, etc. In specific embodiments, the A2 domain is delivered to the individual prior to and/or concomitantly upon exposure of a condition wherein the individual may become particularly susceptible to infection, such as before, during, and/or after surgery, before, during, and/or after a hospital visit, before, during, and/or after chemotherapy and so forth. The individual may have a weakened immune system or other medical illness, in certain embodiments. The sepsis can originate at any location in the body, although common sites include the kidneys (for example, an upper urinary tract infection); the liver; the gall bladder; the bowel, such as is seen with peritonitis; the skin (for example, with cellulitis); and the lungs (such as with bacterial pneumonia), for example. In individuals subject to a hospital setting, usual sites of infection include sites associated with intravenous lines, surgical wounds, surgical drains, catheters, and/or sites of skin breakdown, such as decubitus ulcers or bedsores, for example. Regardless of where the infection started, the end point is a systemic infection, affecting many organs.

In certain embodiments of the invention, the A2 domain or a fragment thereof is a diagnostic tool to detect the levels of circulating activated VWF in blood. In specific embodiments, high levels represent high risk for one or more medical conditions, such as thrombosis, for example. Upon determination of the % of activated VWF, the subject can be treated with anti-VWF (i.e. A2 protein, which recognizes active A1 domain and inhibits GPIb interaction), for example.

In one embodiment of the invention, there is a method of treating and/or preventing sepsis in an individual, comprising delivering to the individual a therapeutically effective amount of an A2 domain of von Willebrand factor, or a fragment of said A2 domain. In specific embodiments, the A2 domain is delivered to the individual as a polypeptide, which may be comprised in a carrier, in certain aspects. In a specific embodiment, the carrier comprises lipid or liposome.

The A2 domain may be obtained from the N-terminal region of A2 or from the C-terminal region of A2, in certain cases. The A2 domain may be further defined as a polypeptide comprising at least 70% identity, at least 75% identity, at least 80% identity, at least 85% identity, at least 90% identity, at least 95% identity, at least 97% identity, at least 98% identity, or at least 99% identity to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30.

In certain aspects of the invention, the individual being treated with methods or compositions of the invention is a patient in a hospital. The individual may have undergone surgery, is undergoing surgery, and/or will undergo surgery, in specific embodiments. The A2 domain may be delivered intravenously, in certain cases. Methods of the invention may further comprise delivering one or more antibiotics to the individual.

In other embodiments of the invention, there is a method of treating and/or preventing thrombosis in an individual, comprising delivering to the individual a therapeutically effective amount of an A2 domain of von Willebrand factor, or a fragment of the A2 domain.

In additional embodiments, there is a method of treating and/or preventing systemic inflammatory reaction syndrome (SIRS) in an individual, comprising delivering to the individual a therapeutically effective amount of an A2 domain of von Willebrand factor, or a fragment of said A2 domain.

In specific embodiments of the invention, there is a kit for treating and/or preventing sepsis, comprising a) one or more of SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30; and/or b) a composition that is at least 70% identical to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 or SEQ ID NO:30.

In additional embodiments, there is a kit for treating and/or preventing thrombosis, comprising a) one or more of SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30; and/or b) a composition that is at least 70% identical to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30.

In further embodiments, there is a kit for treating and/or preventing systemic inflammatory reaction syndrome, comprising a) one or more of SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30; and/or b) a composition that is at least 70% identical to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30.

In an additional embodiment of the invention, there is a method for diagnosing a medical condition in an individual, comprising using the A2 domain to assay a sample from the individual for activated VWF. In specific embodiments of the invention, the assay used is an immuno assay. In one embodiment, this assay could be performed by developing a standard curve of A2 to activated VWF from a pool of normal patients, and comparing the level of activated VWF found by the assay from a patient suspected of having a medical condition against the standard curve. The medical condition may be thrombosis, in specific embodiments, and in further specific embodiments the sample comprises blood, plasma, serum, tissue, or a combination thereof. The A2 domain may be further defined as a) one or more of SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30; or b) a composition that is at least 70% identical to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:30.

The method may be further defined as assaying the level of A2 domain in the sample from the individual, in specific embodiments. Also, the level of A2 domain may be compared with the level of A2 domain in a reference sample and/or the level of A2 domain may be compared with a known standard, such as one determined upon ascertaining levels of multiple individuals with the medical condition, for example.

In some embodiments of the invention, there is a peptide consisting essentially of SEQ ID NO:26, SEQ ID NO:27, SEQ ID NO:28, or SEQ ID NO:30. In other embodiments of the invention, there is a peptide consisting of SEQ ID NO:26, SEQ ID NO:27, SEQ ID NO:28, or SEQ ID NO:30. In additional embodiments, there is a peptide comprising SEQ ID NO:26, SEQ ID NO:27, SEQ ID NO:28, or SEQ ID NO:30.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying FIG.s. It is to be expressly understood, however, that each of the FIG.s is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

(FIG. 2B) human fibrinogen, Fragment D or Fragment E of fibrinogen. Bound protein was determined by ELISA using anti-H is antibody. Each point represents the mean±SD of values obtained from one triplicate assay from three independent experiments.

In FIG. 3B, the bar graph shows the number of platelets adhered/field after 2 min of perfusion of the blood. Columns represent three separate experiments.

In FIG. 4A, photomicrographs showing the adhered platelets without or with rolling leukocytes after 3 min perfusion are provided. The arrowheads point to leukocytes. In FIG. 4B, the graph shows the number of leukocytes observed in a total of 15 fields.

In FIG. 5A, the HUVECs were perfused with whole blood (citrated) that had been mixed with LPS and/or A2 protein at low shear rate (200 s$^{-1}$). During the 2 min of perfusion, the number of transmigrating leukocytges (clearly viewed by transillumination) was counted in 5 contiguous fields. Similarly, the number of ULVWF-plately strings, (FIG. 5B) (between brackets) were counted during the same time of perfusion. In FIG. 5C, it shows the number of strings observed during 2 min of perfusion.

In FIG. 7A, there is necrosis in the gut and discoloration in both the liver, and in FIG. 7B, the kidney, from the mouse with LPS only. In contrast, no difference was observed between mouse with LPS+A2 protein and control (none).

FIG. 1B demonstrates that after 3 min of perfusion, the number of BSA- or A2-coated beads was counted in 12 contiguous fields.

In FIG. 12A, the purified A2 polypeptide was tested for its ability to bind full length VWF. Increasing concentrations of the A2 polypeptide were incubated with immobilized VWF. Bound protein was determined by ELISA as described under Materials and Methods. Each point represents mean±S.D. of two independent sets of triplicate determinations. In FIG. 12B, increasing concentrations of the A2 polypeptide were incubated with immobilized A1 domain polypeptide. Bound protein was determined by ELISA and each point represents mean±S.D. of four determinations.

In FIG. 14A, purified plasma VWF (5 µg/ml) mixed with buffer or ristocetin (0.5 mg/ml) was incubated in wells coated with the VWF-A2 polypeptide. Bound VWF was detected by ELISA as described herein. The VWF efficiently bound to A2 polypeptide only in the presence of ristocetin. The VWF-A1 polypeptide inhibited the ristocetin-induced binding of VWF to A2 protein. Columns represent mean±S.D. of two sets of triplicate assays. FIG. 14B shows testing of the ability of Ultra-large (UL) VWF multimers to bind recombinant VWF-A2 domain polypeptide. ULVWF (0.5 µg/ml) had comparable binding activity to immobilized VWF-A2 polypeptide in the presence or absence of ristocetin. Columns represent mean±S.D. of two sets of triplicate assays.

In FIG. 15A, whole blood was perfused over each coverslip coated with the recombinant VWF-A1 domain polypeptide (4 µM) and pre-incubated with A3 or A2 polypeptide (4 µM). The bar graph shows the number of platelets tethered to the surface (mean±S.D.) after 2 min perfusion of the whole blood. Columns represent six separated experiments. In FIG. 15B, VWF-coated surfaces were pre-incubated with A3 or A2 polypeptide (4 µM). Whole blood was perfused through the chamber at 1500 s$^{-1}$. Platelets adherent to VWF-coated coverslips pre-incubated with A3 or A2 polypeptide are seen under phase contrast frames. The photomicrographs depict the platelets tethered to the surface after 2 min of perfusion. In comparison with VWF containing the A3 polypeptide, platelet attachment was significantly reduced after perfusion with whole blood over a surface of VWF previously incubated with the A2 polypeptide. The figure is representative of three independent experiments.

In FIG. 16A, each of VWF-A1, A2 or A3 polypeptide (4 µM) was incubated with PRP diluted in PBS (1:2) for 2 min at 37° C. in an aggregometer cuvette. Agglutination was initiated by the addition of 1 mg/ml ristocetin. Platelets were stirred continuously at 1,200 rpm at 37° C. As expected, the VWF-A1 domain polypeptide completely inhibited while the VWF-A3 domain polypeptide did not inhibit ristocetin-induced platelet agglutination at the concentration tested. The VWF-A2 polypeptide inhibited 50% of platelet agglutination. Figure represents four independent assays. In FIG. 16B, increasing concentrations of VWF-A2 polypeptide were incubated with PRP for 2 min at 37° C. Agglutination was initiated by the addition of 1 mg/ml ristocetin. Figure represents four independent assays.

FIG. 17 illustrates exemplary synthetic peptides (10) to narrow the N-terminal (half) A2 domain (1481-1605).

In FIG. 19A, the purity of the recombinant A1A2 protein was verified by SDS gel electrophoresis under non-(NR) or reducing (R) conditions (inset). The purified protein was then tested for its ability to bind platelet GPIbα. Increasing concentrations of VWF-A1 or A1A2 protein were incubated with immobilized fixed platelets. Bound proteins were detected with anti-His tag antibody. Graph shows specific binding, and it is representative of two independent triplicate experiments (mean±SD). In FIG. 19B, VWF-A1 or A1A2 protein (2 µM) was incubated with PRP diluted in TBS (1:2) for 3 min at 37° C. in an aggregometer cuvette. Agglutination was initiated by the addition of 1 mg/ml ristocetin. Platelets were stirred continuously at 1200 rpm at 37° C. The A1 domain protein inhibited 100% agglutination, while the A1A2 protein inhibited 40%. The figure is representative of four independent experiments. In FIG. 19C, whole blood was perfused over each coverslip coated with the recombinant A1 or A1A2 polypeptide (4 µM). The bar graph shows the number of platelets tethered to the surface (mean±S.D.) after 2 min perfusion of the whole blood. Columns represent three separated experiments.

FIGS. 23A-23B show the effect of exemplary peptide of SEQ ID NO:2 on thrombosis. FIG. 23A shows the effect of the peptide on RIPA. FIG. 23B demonstrates platelet adhesion to immobilized collagen under high flow conditions with the peptide FIG. 24A shows the effect of the peptide on RIPA. FIG. 23B demonstrates platelet adhesion to immobilized collagen under high flow conditions with the peptide.

FIG. 26A shows the A2 domain bound to vimentin using two different anticlonal antibodies: Anti-2 (triangles) and VP-1 (squares). FIG. 26B shows the binding of two different A2 domain peptides (diamond and square) of increasing concentration to vimentin after the subtraction of non-specific binding

DETAILED DESCRIPTION OF THE INVENTION

I. DEFINITIONS

Figure 1:
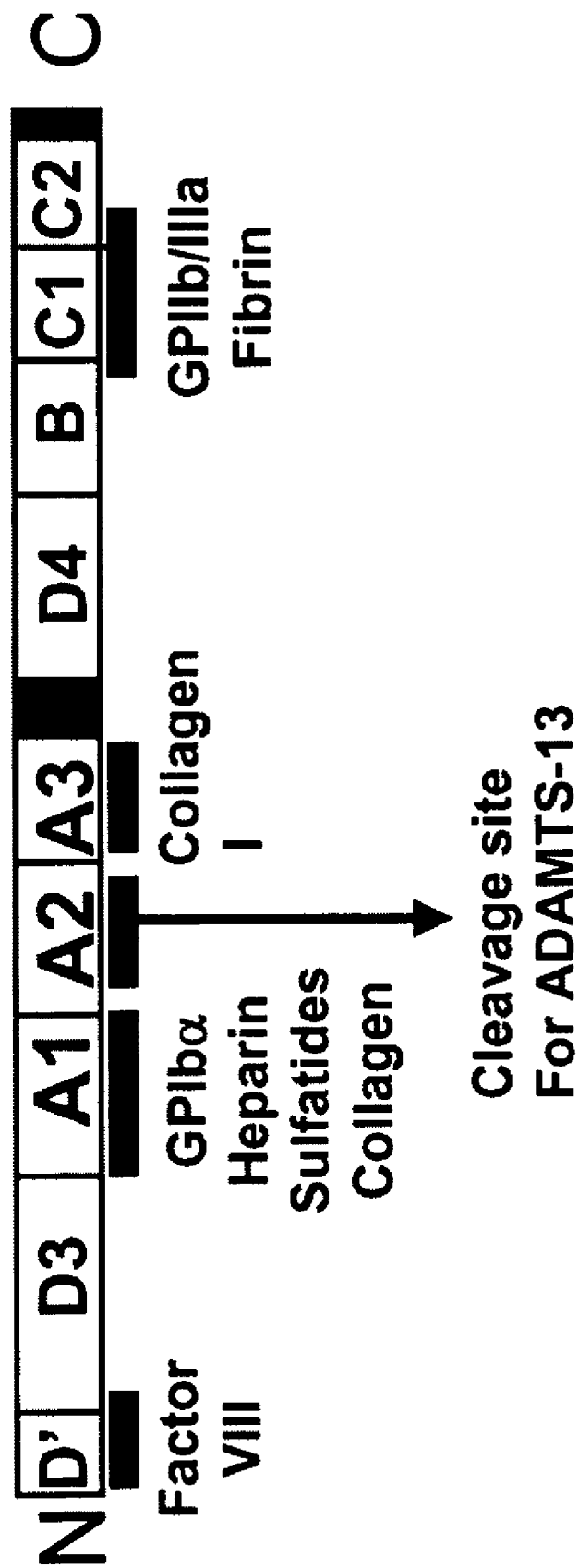
FIG. 1 illustrates an exemplary representation of a mature von Willebrand factor subunit.

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

The term "biological sample" refers to a sample obtained from a mammal for the purpose of diagnosis, prognosis, or evaluation. In certain embodiments, such a sample may be obtained for the purpose of determining the outcome of an ongoing condition or the effect of a treatment regimen on a condition, or both. Examples of biological samples are blood samples, serum samples, plasma samples, cerebrospinal fluid, tissue samples, and urine samples. In a preferred embodiment, the biological sample is a blood sample.

The term "domain" as used herein refers to a subsection of the polypeptide which possesses a unique structural and/or functional characteristic; typically, this characteristic is similar across diverse polypeptides. The subsection typically comprises contiguous amino acids, although it may also comprise amino acids that act in concert or that are in close proximity due to folding or other configurations. An example of a protein domain is the A2 domain of VWF.

A portion of a protein, such as a peptide, for example, is "functionally active" when it displays physiological activity to diagnose, treat and/or prevent at least one of the symptoms of sepsis, thrombosis and/or SIRS. For example, the portion could comprise a fibrin binding site, a vimentin binding site, the activity to bind endothelial cells, and/or the activity to directly or indirectly bind to fibrin and/or vimentin.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, horses, cows, goats, sheep, mice, rats, and chimpanzees. Mammals may be referred to as "patients".

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

As used herein, "plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

The term "prevention" includes either preventing the onset of at least one symptom of a medical condition, for example, preventing the onset of at least one symptom of sepsis, SIRS, or thrombosis, for example. The prevention may refer to delaying the onset of at least one symptom of a medical condition, in certain embodiments.

The term "thrombosis" as used herein refers to the formation of a clot or thrombus inside a blood vessel, and in specific embodiments obstructs the flow of blood through the circulatory system of an individual.

The term "treatment" refers to any process, action, application, therapy, or the like, wherein a mammal, including a human being, is subject to medical aid with the object of improving the mammal's condition, directly or indirectly.

The terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence. The terms "variant" and "mutant" when used in reference to an amino acid sequence refer to an amino acid sequence that differs by one or more amino acids residues from another, usually a related amino acid sequence. A "variation" is a difference between two different amino acid sequences; typically, one sequence is a reference sequence.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

II. EMBODIMENTS OF THE PRESENT INVENTION

The present invention concerns the diagnosis, treatment and/or prevention of sepsis, SIRS, and/or thrombosis, for example, with the A2 domain of VWF or a portion thereof.

In severely traumatized and critically ill patients, the development of sepsis remains the leading clinical concern and late cause of death (tenth cause of death in U.S.). With an estimate of 2% to 11% of all admissions treated in hospitals and intensive care units throughout the world, the incidence of sepsis and sepsis-related deaths is still increasing and represents a major burden to the U.S. healthcare system with costs of over $16 billion annually. Sepsis is frequently characterized by an early systemic inflammatory response to infection, associated with hypoperfusion followed by tissue injury and subsequent organ damage. To date there is only one drug to treat sepsis and the outcome is not as expected.

Von Willebrand factor (VWF) is a multimeric plasma glycoprotein that plays a critical role in supporting platelet adhesion and aggregation at sites of vessel injury. The A2 domain is the second domain of a sequence of three domains in VWF. This human VWF domain, expressed as a recombinant protein contains binding activity for fibrin. This A2 protein was tested in mice challenged with lipopolysaccharide (LPS) to analyze its effect on platelets adhesion on deposited fibrin. Mouse model of endotoxemia (LPS) is a well known animal model to study sepsis and disseminated intravascular coagulation (DIC). This is a disorder characterized by massive systemic intravascular activation of coagulation, leading to widespread deposition of fibrin in the circulation that can compromise the blood supply to various organs, thus contributing to multiple organ failure.

The inventor demonstrated that mice containing LPS (i.p.)+A2 protein (i.v.) after being very sick recovered between 36 and 48 hours after the injection while those mice only with LPS+buffer died. The phenotype (i.e., hair, eyes, activity) of the recovered mice (LPS+A2) is identical to control mice (none). In addition, mice containing LPS only or LPS+low dose of A2 protein demonstrated defect in organs such as kidneys, heart, lung, gastrointestinal tract and liver. In fact, the appearance of the organs from the recovered LPS+ A2 protein mice was identical to the control mice. These animals received only one single dose of the A2 protein. Therefore, recombinant human VWF-A2 protein is useful for the treatment and/or prevention of sepsis.

Other embodiments of the invention relate to the A2 domain polypeptide interacting with the A1 domain in VWF and inhibiting platelet adhesion under high flow conditions. Von Willebrand factor (VWF) contains a triplicate repeat sequence or A domains that play an important function in the biology of VWF. The second repeat of this sequence, the A2 domain, contains the cleavage site for the metalloprotease ADAMTS-13, which converts the hyperreactive unusually large (UL) forms of VWF into less active plasma forms. The inventor characterized the relationship between the A2 domain and its neighboring A1 domain, which binds to platelet glycoprotein (GP) Ibα using recombinant A domain polypeptides, purified plasma VWF and monoclonal antibodies. The A2 domain polypeptide specifically bound to immobilized A1 domain polypeptide or full length VWF with a half-maximal binding occurred at 65 or 190 nM, respectively. This interaction was effectively blocked by monoclonal antibodies against the A2 domain. Plasma VWF bound immobilized A2 domain polypeptide only in the presence of ristocetin, while in sharp contrast the ULVWF multimers bound without ristocetin. The involvement of the A1 domain in this interaction was further supported by showing that the A1 domain polypeptide effectively blocked the ristocetin-induced VWF-binding to the A2 domain polypeptide. Therefore, using recombinant human VWF-A2 protein to detect for activated VWF is useful for the diagnosis of thrombiosis. This invention also concerns a novel inhibitory function for the isolated A2 domain in which its binding to A1 domain polypeptide or multimeric VWF blocked the interaction with platelet GPIbα under high flow conditions. The A2 domain polypeptide also inhibited ristocetin-induced platelet agglutination. These results indicate that an interaction between the A2 and the A1 domains in full length VWF inhibits the binding to platelet GPIbα.

III. THE A2 DOMAIN OF VON WILLEBRAND FACTOR

In particular embodiments of the invention, the A2 domain of von Willebrand Factor is employed. The A2 domain may be utilized as a whole or as a functional fragment thereof. For example, one of skill in the art may employ SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, or SEQ ID NO:30 as the certain embodiment of the A2 domain, or another A2 domain molecule may be used, such as one having conservative substitutions of SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:27, SEQ ID NO:28, or SEQ ID NO:30. In particular embodiments, there may be 1, 2, 3, 4, 5, 6, 7, 8, 9, 10, 11, 12, 13, 14, 15, or more conservative substitutions in the A2 domain. In other aspects of the invention, fragments of the A2 domain are used, and one of skill in the art may identify such fragments by standard means in the art.

In certain aspects, potential yet exemplary synthetic peptides to narrow the N-terminal (half) A2 domain (1481-1605) are illustrated in FIG. 17. A similar approach may be used for the C-terminal A2 polypeptide or any other polypeptide. Recombinant A2 domain polypeptide of VWF (published) is as follows: 1481-GLLGVSTLGPKRNSMVLDVAFV-LEGSDKIGEADFNRSKEFMEEVIQRMD-VGQDSIHVTV LQYSYMVTVEYPFSEAQSKG DILQRVREIRYQGGNRTNTGLALRYLS-DHSFLVSQGDRE QAPNLVY-MVTGNPAS-DEIKRLPGDIQVVPIGVGPNANVQE-LERIGWPNAPILIQDF ETLPREAPDLVLQR-1668 (SEQ ID NO:1). The N-terminal (half) of the A2 domain of VWF (new) is as follows: 1481 (718)-GLLGVSTLGPKRNSMV-LDVAFVLEGSDKIGEADFNR-SKEFMEEVIQRMDVGQDSIHVTV LQYSYM-VTVEYPFSEAQSKGDILQRVREIRYQGGNRTNTGLAL-RYLSDHSFLVSQGDRE QAPNLVY-(842)1605 (SEQ ID NO:2).

The C-terminal (half) of the A2 domain of VWF (new) is as follows: 1606 (843)-MVTGNPASDEIKRLPGDIQV-VPIGVGPNANVQELERIGWPNAPILIQD-FETLPREAPDLVL QR-(905)1668 (SEQ ID NO:3). The three polypeptides have been expressed in bacteria, for example.

IV. SEPSIS

Sepsis is a critical medical condition caused by excessive toxin-producing bacteria infection in the bloodstream. Symptoms include the following: fever or hypothermia (low body temperature); chills; shaking; hyperventilation; skin warm to the touch; rash; rapid heart beat; confusion or delirium; and/or decreased urine production. Tests for sepsis include at least an abnormal white blood cell count; low platelet count; positive bacterial blood culture; blood gases that indicate acidosis; and/or abnormal kidney function tests, for example.

Sepsis is conventionally treated with broad spectrum antibiotics, which may be delivered intravenously. If and when the causative organism is identified, the antibiotic course may be altered to treat the causative organism. If and when the source of the infection is identified, the source should be removed, if possible (such as infected intravenous lines or surgical drains, for example). Additional therapy using oxygen, intravenous fluids, and/or medications that increase blood pressure may be utilized, in certain cases. In particular embodiments of the invention, sepsis is treated with the methods or compositions of the invention in addition to a conventional treatment, such as one or more antibiotics (such as ceftriaxone, glycopeptides, carbapenems and some quinolones, amoxycillin, gentamicin, cefoxitin, flucloxacillin, amikacin, metronidazole, vancomycin, or cefotaxime, for example) or drotrecogin alfa (activated), for example.

In certain aspects, the invention is employed with one or more of these therapies to treat and/or prevent sepsis.

V. SYSTEMIC INFLAMMATORY RESPONSE SYNDROME (SIRS)

Systemic inflammatory response syndrome occurs upon a wide variety of severe clinical insults, manifested by two or more of the following conditions: temperature >38° C. or <36° C.; heart rate >90 beats/min; respiratory rate >20 breaths/min or $PaCO_2$<32 mm Hg; white blood cell (WBC) count >12,000/$mm^3$, <4000/$mm^3$, or >10% immature (band) forms. When SIRS occurs with a confirmed infection, such as one established through a positive blood culture and/or tissue sample positive for pathogenic organisms, for example, it is referred to as sepsis. Immunosuppressants, or broad-spectrum antibiotics are current treatment options for SIRS.

In certain aspects, the invention is employed with one or more of these therapies to treat and/or prevent SIRS.

VI. THROMBOSIS

Thrombosis is the formation of a clot or thrombus inside a blood vessel, obstructing the flow of blood through the circulatory system. A thrombus, or blood clot, is the final product of the blood coagulation step in hemostasis. It is achieved via the aggregation of platelets that form a platelet plug and the activation of the humoral coagulation system (i.e. clotting factors). A thrombus is physiologic in cases of injury, but pathologic in case of thrombosis.

Thrombosis is currently treated with a variety of methods depending on patient status such as age, general health and medical history. Anticoagulant medications including coumadin and heparin are used to treat the condition, as other medications such as tissue plasminogen activator (t-PA) and/or enzymes such as streptokinase. Physical methods such as catheters can also be employed to expand the width of involved vessels. A combination of these methods is used as needed. In certain aspects, the invention is employed with one or more of these therapies to treat, diagnose and/or prevent thrombiosis.

The acute inflammatory response to sepsis gives rise to significant morbidity and mortality. A generalized microvascular thrombosis may play an important role in tissue ischaemia. Microvascular thrombosis in certain embodiments is an adaptive response that prevents bacteria in the tissues reaching the systemic circulation via the capillaries. In time, a definitive response by leucocytes removes the bacteria and repairs the damaged tissues. There is, however, evidence that if microvascular thrombosis becomes generalized, then extensive tissue ischaemia may precipitate organ failure and death. Post-mortem studies of patients with sepsis demonstrate microvascular thrombi in many organs including the kidney, liver, lung, gut, adrenals and brain, and the degree of organ injury is related to the quantity of thrombi.

In addition, Disseminated Intravascular Coagulation (DIC) is a common acquired coagulation disorder resulting from excessive activation of the coagulation system, usually due to massive tissue injury, sepsis, or certain pregnancy complications. The normal anticoagulant and fibrinolytic systems are overwhelmed and cannot contain the coagulation activation, which becomes systemic, resulting in disseminated microvascular thrombi. In specific embodiments of the invention, one or more symptoms of DIC is ameliorated with methods and/or compositions of the invention.

VII. PHARMACEUTICAL PREPARATIONS

Exemplary pharmaceutical compositions of the present invention comprise an effective amount of one or more A2 domains of VWF or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one A2 domain of VWF or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The A2 domain of VWF may comprise different types of carriers depending on whether it is to be administered in solid, liquid or aerosol form, and whether it need be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference).

The A2 domain of VWF may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include A2 domain of VWF, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the A2 domain of VWF may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the A2 domain of VWF is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5, 580, 579 and 5, 792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629, 001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, A2 domain of VWF may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537, 514, 6, 613, 308, 5, 466, 468, 5, 543, 158; 5, 641, 515; and 5, 399, 363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound A2 domain of VWF may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5, 804, 212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. DIAGNOSIS

The A2 domain polypeptide can be used to distinguish between activated and non-activated circulating VWF. Activated VWF circulating in blood can be found in conditions where the vascular endothelium is dysfunctional such as preclampsia, cancer, inflammation, diabetes, metabolic syndrome and cardiovascular disease. A high level of activated VWF in patients is indicative of high risk to develop a medical condition such as thrombosis, in certain aspects. In one embodiment of the invention, the A2 polypeptide is used to assay for activated VWF. A standard curve of non-activated VWF is determined from serial dilutions of normal pool of individuals, and the percent of activated VWF from a sample is compared against a standard curve of non-activated VWF to determine the level of activated VWF. In specific embodiments, high levels of activated VWF indicate high risk for one or more medical conditions, such as thrombosis. In certain embodiments of the invention, the assay used to decect activated VWF is an immuno assay. In particular embodiments, the assay used is an immunosorbant assay. In specific embodiments, the assay used is an ELISA.

IX. KITS OF THE INVENTION

Any of the compositions described herein may be comprised in a kit. In a non-limiting example, an A2 domain of VWF may be comprised in a kit. The kits will thus comprise, in suitable container means, an A2 domain of VWF and, optionally, an additional agent, such as a carrier or another pharmaceutical composition, including one or more antibiotics.

The kits may comprise a suitably aliquoted A2 domain of VWF or fragment thereof of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the an A2 domain of VWF and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The A2 domain of VWF compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the ultimate an A2 domain of VWF composition within the body of an animal. Such an instrument may be a syringe, pipette, forceps, and/or any such medically approved delivery vehicle.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Embodiments of the Invention

The invention greatly contributes to alleviating patients with not only sepsis but also those affected with a systemic inflammatory reaction syndrome or thrombosis, for example, or any condition wherein A2 domain of VWF provides improvement of at least one symptom.

While characterizing the isolated form of the A2-domain of Von Willebrand Factor (VWF-A2 protein), a plasma glycoprotein that in specific embodiments of the invention plays an important role in thrombosis, it was noticed that in an inflammatory milieu, the recombinant A2-domain interfered with the interaction between endothelial cells, leukocytes and platelets. Knowing that an enhanced interaction between these cells is the common factor that underlies the pathophysiology of acute life threatening inflammatory reactions such as the one described in sepsis, this exemplary protein (A2-domain) was utilized in mice with a systemic inflammatory reaction induced by LPS. As described in the literature, LPS induces a clinical picture similar to the one observed in patients with sepsis.

Interestingly, this A2-domain led to a complete recovery of the LPS-treated animals with 100% survival compared with controls. Now fueled by this significant observation, the biological mechanisms that are set off by the isolated A2-domain of VWF during a state of systemic inflammation may be further characterized. In particular aspects, the following embodiments are further addressed: 1) evaluation of the using VWF-A2 protein or a fragment thereof, such as recombinant VWF-A2 protein or a fragment thereof, as a therapy for sepsis using a mouse model of endotoxemia. In specific aspects, a mouse model of endotoxemia is utilized to characterize survival studies. Mice in which endotoxemia has been induced by LPS are treated with purified VWF-A2 protein and compared with untreated controls. Clinical signs, recovery rate, and mortality may be measured, for example; 2) the effect of VWF-A2 protein on LPS, such as recombinant VWF-A2 protein on LPS, is examined on induced systemic inflammation. An animal model of endotoxemia may be employed to determine the beneficial physiological responses that are induced by intravenous administration of VWF-A2 protein; 3) the effect of recombinant VWF-A2 protein on platelets and leukocytes in endotoxemia is characterized. This embodiment may use intravital microscopy to observe the microcirculation in real time and measure the effect of the VWF-A2 protein on platelet adhesion to the endothelium, formation of microthrombi, and interaction of leukocytes with endothelial cells during LPS induced endotoxemia; and/or 4) the interaction of the VWF-A2 domain with endothelial cells is characterized, which in specific aspects identifies the protein(s) on the endothelial cell surface where the A2 protein interacts and identifies the cellular markers that are regulated by this interaction.

Example 2

The Recombinant VWF-A2 Domain Binds Fibrin

Figure 2:
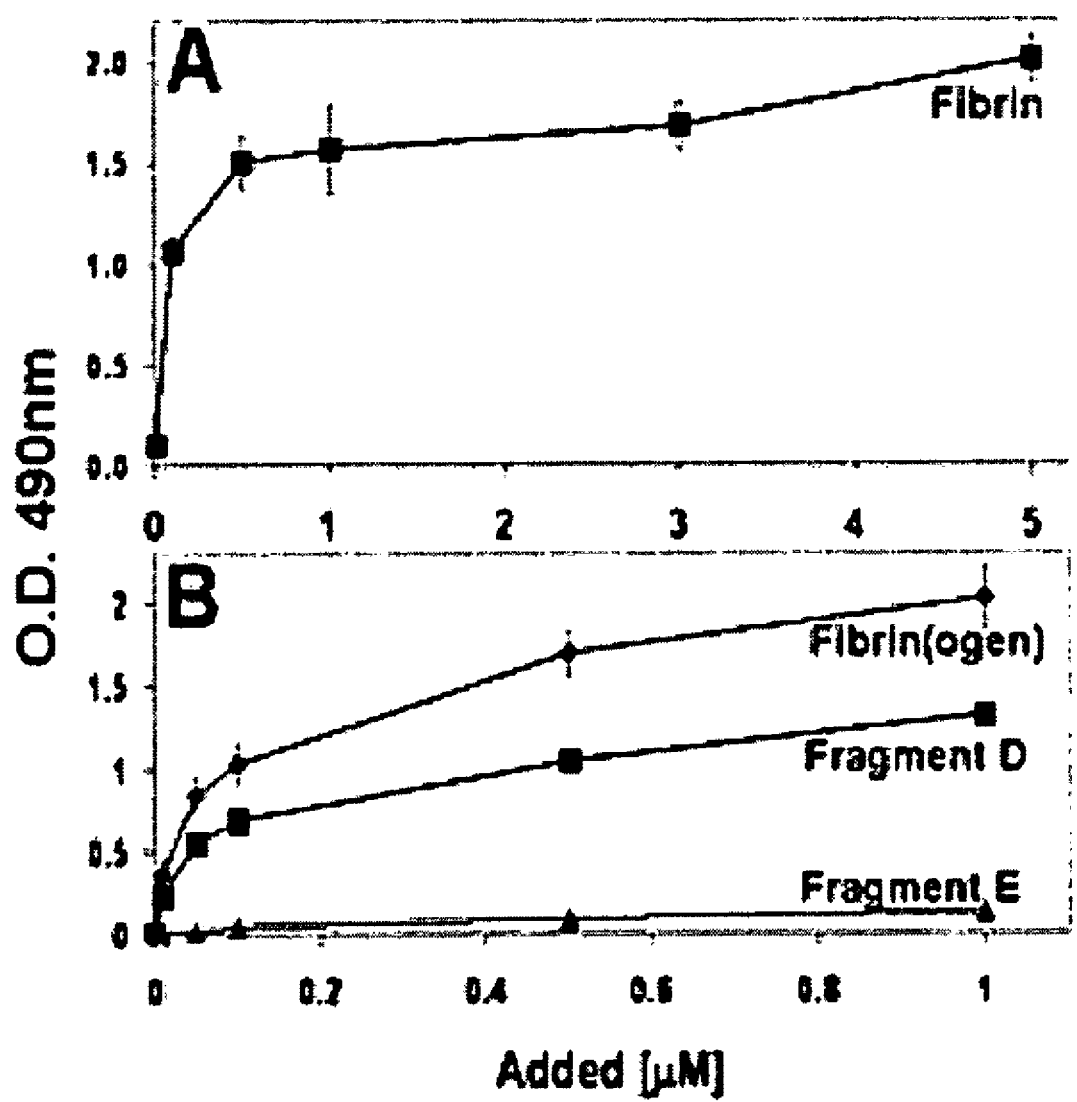
FIGS. 2A-2B demonstrate that increasing concentrations of A2 protein were incubated with either (FIG. 2A) immobilized human fibrin.

Although VWF and fibrinogen normally do not associate in plasma, VWF binds to surface-bound fibrinogen or to deposited fibrin (Endenburg et al., 1995; Loscalzo et al., 1986). Previously, it was reported that fibrin may induce VWF binding to platelet GPIb (Loscalzo et al., 1986). Among the recombinant A1, A2 and A3 proteins tested, only the A2 protein bound to both polymerized human fibrin (FIG. 2) and immobilized human fibrin(ogen) (FIG. 2B) in a concentration-dependent and saturable manner. The half-maximal binding to both forms of fibrinogen occurred at 150 nM. These results indicate that both fibrin and immobilized fibrin (ogen) expose the site(s) that recognizes the A2 domain. In addition, since fibrinogen is a large multidomain protein consisting of two major structural regions, D and E, the binding of the A2 protein to either fragment D or E was also tested. The A2 protein distinctively bound to fragment D of fibrinogen (FIG. 2B).

Figure 3:
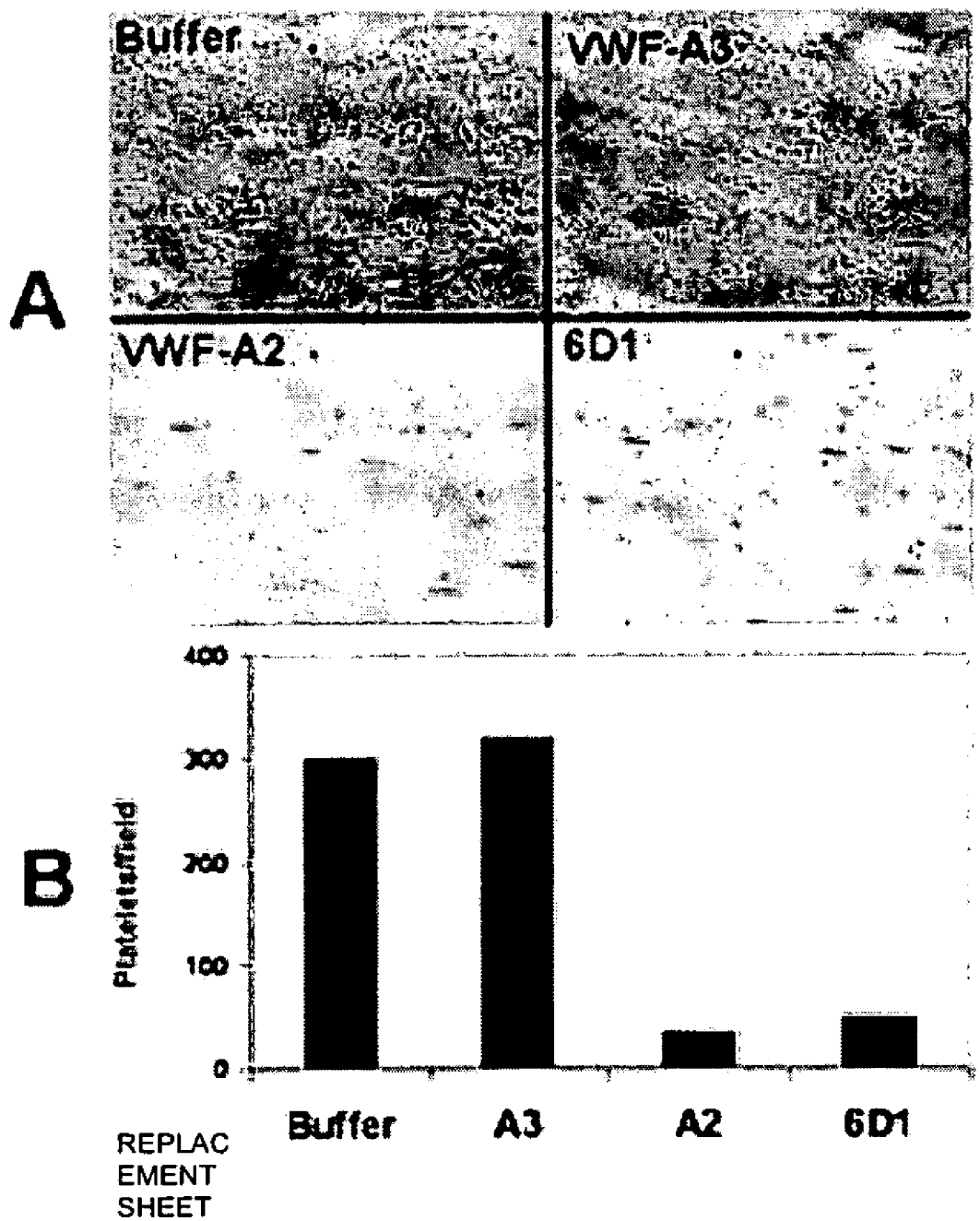
FIGS. 3A-3B show that (FIG. 3A) whole blood (containing sodium citrate as anti-coagulant) was perfused at flow rate of 1500 s$^{-1}$ over immobilized human fibrin(ogen) pre-incubated with each buffer. VWF-A3 or VWF-A2 protein (2 µM). In addition, blood containing antibody against GFIB (6D1) was perfused over fibrin(ogen) pre-incubated with buffer only. The photos depict the platelets adhered to the surface after 2 minutes of perfusion and represent three separated experiments with blood from different donors.

Since the A2 protein blocked the binding of multimeric VWF to fibrin(ogen), in a specific embodiment the A2 protein also inhibits the interaction of plasma VWF to fibrin or insoluble fibrin(ogen) under flow conditions, reducing the number of tethering platelets. In comparison with the positive controls assays (FIG. 3, buffer and VWF-A3) the number of rolling or adhered platelets on immobilized fibrin(ogen) incubated with A2 protein was markedly reduced (FIG. 3). The inhibition of the antibody 6D1, which is against platelet GPIbα, demonstrated that the platelet adhesion was mainly mediated by the GPIb-VWF interaction (FIG. 3). Identical results were obtained using fibrin. These results indicate that the A2 domain in VWF contains a binding site for fibrin, and that it recognizes a sequence within the fragment D of fibrinogen.

Figure 4:
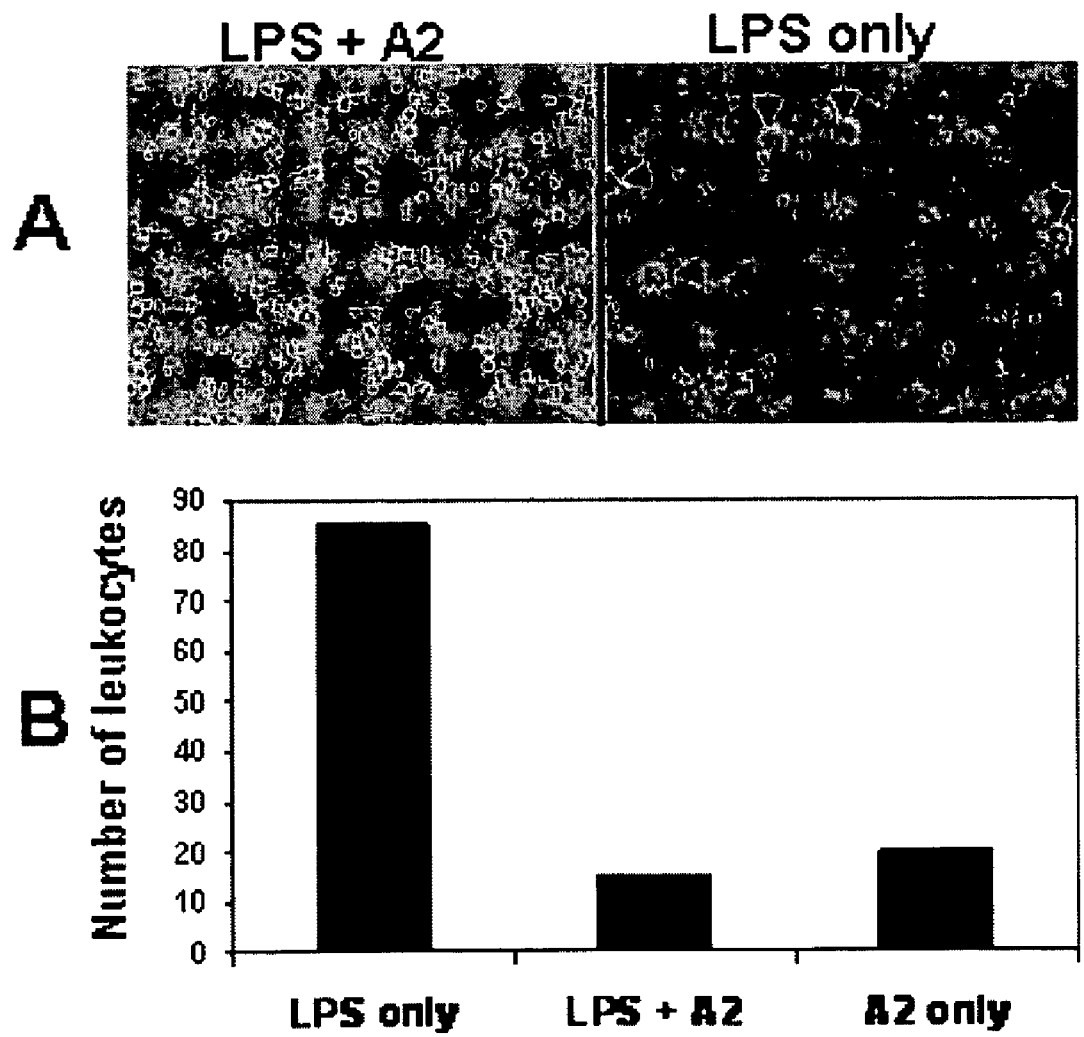
FIGS. 4A-4B show that whole blood (citrated) was incubated with LPS (60 g/ml) and/or A2 protein (80 µg/ml) 3 min prior to perfusion over a fibrinogen coated plates at low shear rate (200 s$^{-1}$).

It is well established that platelets interact with immobilized fibrin(ogen) via the fibrinogen receptor GPIIb/IIIa under low shear stress conditions (Reininger et al., 2000). However, very recently it was reported that treatment of platelets with LPS significantly increased the binding to immobilized fibin(ogen) under low shear conditions (Andonegui et al., 2005). The study demonstrated that this interaction was mediated via the Toll like receptor (TLR)-4. It was then investigated whether the A2 protein would be able to block the interaction of LPS-treated platelets with fibrinogen under low shear conditions. The reason was that in endotoxemia the fibrinolytic pathway is inhibited, increasing the deposition of fibrin on the endothelium (Wong et al., 2000), and therefore, it was examined if VWF is involved in this condition. The number of platelets adhered on fibrin(ogen)-coated plates was comparable between whole blood containing LPS only and whole blood containing LPS and A2 protein (FIG. 4A). This observation indicates that the interaction between LPS-treated platelets and immobilized fibrinogen is independent of VWF. However, the striking difference observed between the two experiments is that the number of transmigration leukocytes over the fibrin(ogen) surface was markedly reduced with the addition of the A2 protein to the blood containing LPS (FIG. 4B). Because leukocytes bind to fibrin (ogen) via integrin alpha(M)beta2 (Mac-1), which is a high-affinity receptor on stimulated monocytes and neutrophils, the A2 protein and Mac-1 may recognize a similar binding site in fibrinogen. The effect of the A2 protein on the interaction between leukocytes and endothelium may be studied in vivo using the ex vivo mouse model of endotoxemia described elsewhere herein.

Example 3

Recombinant VWF-A2 Domain Diminished the Formation of ULVWF-Platelet Strings and Reduced the Interaction Between Leukocytes and HUVEC in the Presence of LPS Under Flow Conditions The results obtained with LPS led the inventor to further study the effect of the recombinant VWF-A2 on a more physiological setting by perfusing whole blood with LPS over a surface of HUVEC. The reason is because LPS activates endothelial cells, leukocytes and platelets, stimulating the secretion of inflammatory markers. Whole blood (citrated) was incubated with LPS (80 µg/ml) and/or A2 protein (80 µg/ml) for 5 min prior to perfusing over a plate containing confluent HUVEC. During the perfusion of the blood containing LPS only (low shear rate, 200 s$^{-1}$) there were a large number of leukocytes slowly moving over the cells (transmigration) and a significant number of ULVWF-platelet strings (FIGS. 5A and 5C). In sharp contrast, when the blood incubated with both LPS and A2 protein was perfused, the number of rolling leukocytes was comparable to control experiments (blood+buffer or A2 only) and the several ULVWF-platelet strings formed were rapidly cleaved (FIGS. 5A and 5C). The results obtained in these studies performed in an inflammatory milieu, indicated a potential role for the A2 protein as an inhibitor of microvascular thrombosis, which is a complication manifested in sepsis.

Example 4

Figure 7:
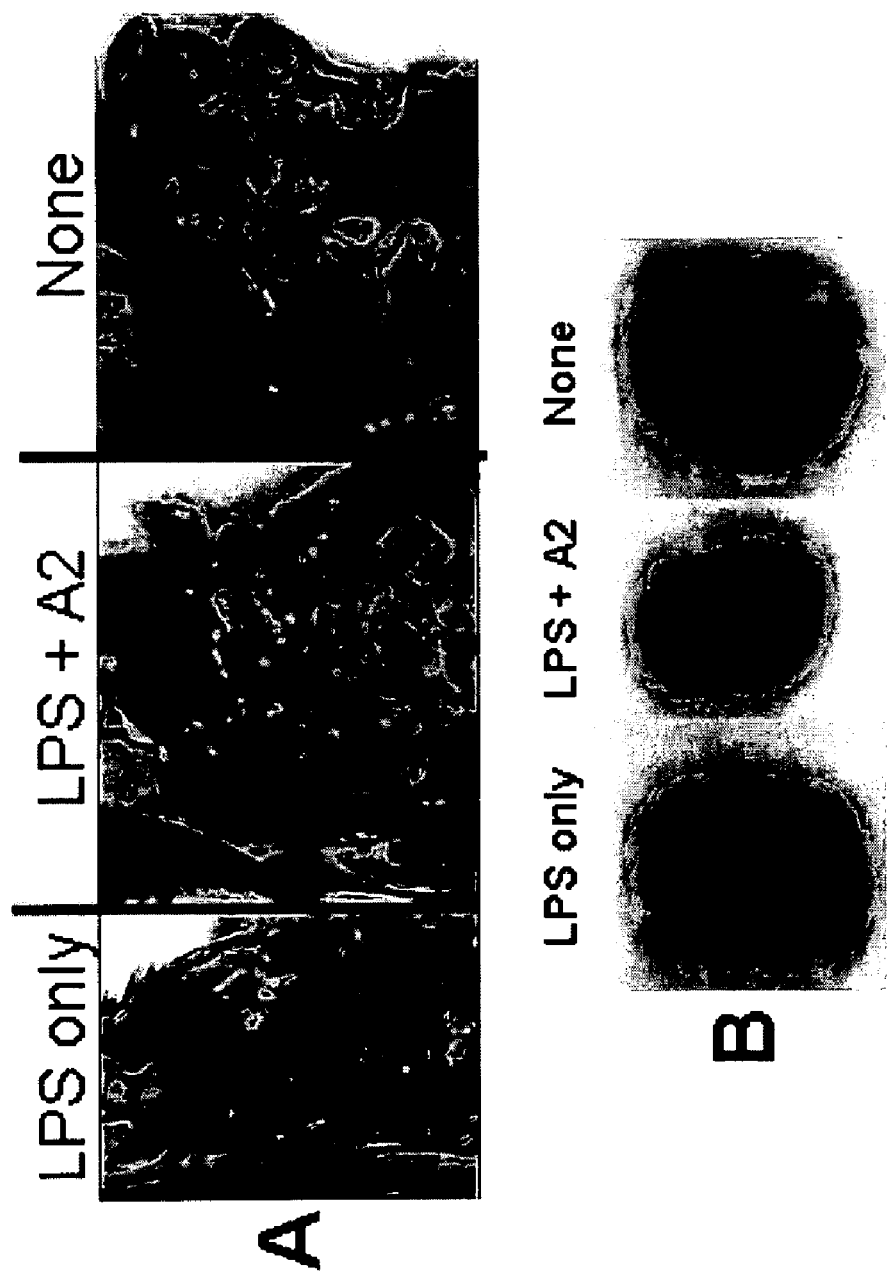
FIGS. 7A-7B show that after 96 hours, the mice were sacrificed to examine the organs.
Figure 8:
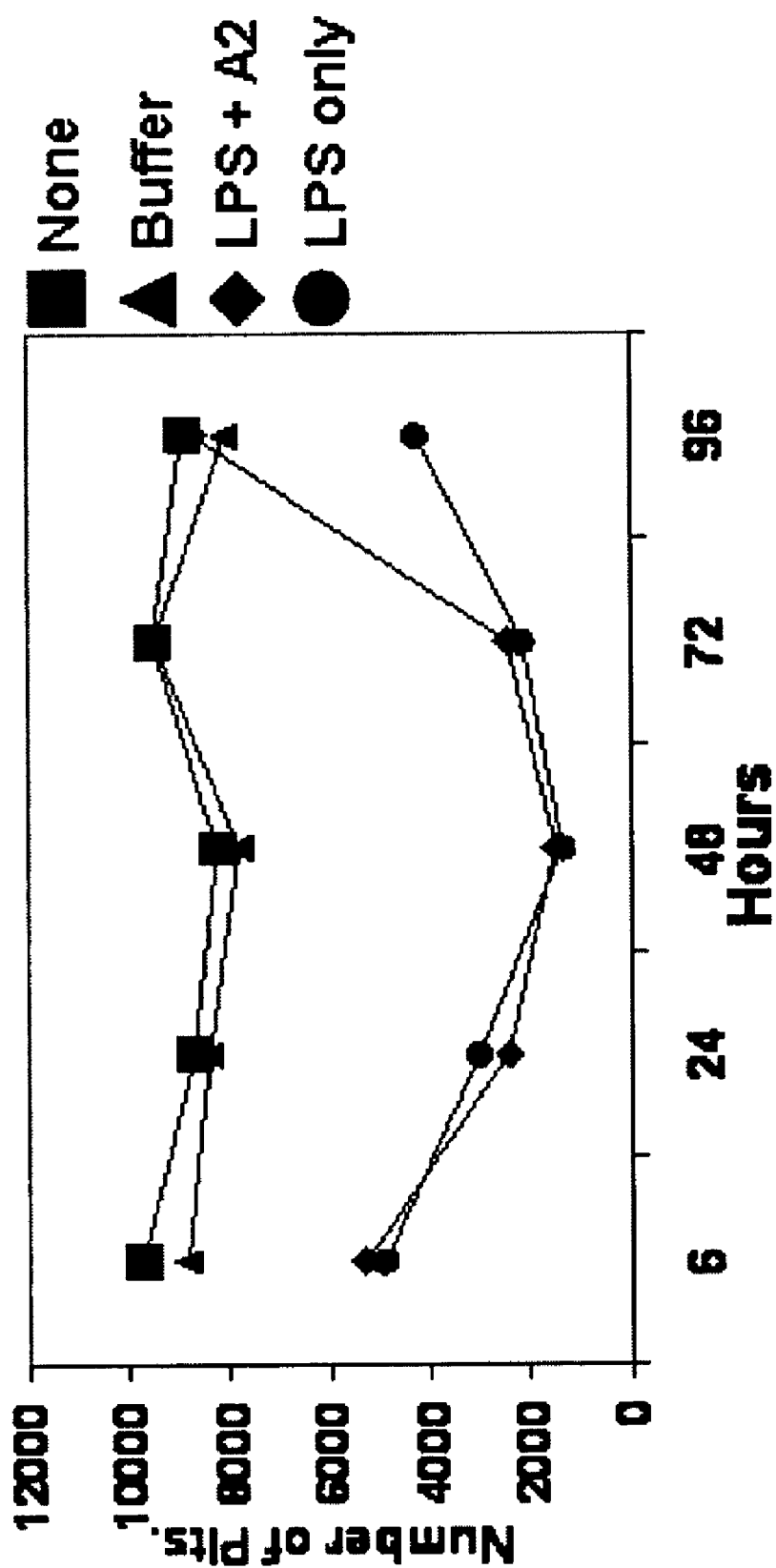
FIG. 8 shows a graph that illustrates the serial determination of platelet count at different time points. After collecting the blood, the platelets were counted using flow cytometry. The increment of the platelet counts observed in mouse with LPS+A2 protein after 72 h correlates with the recovery of the animal.
Figure 9:
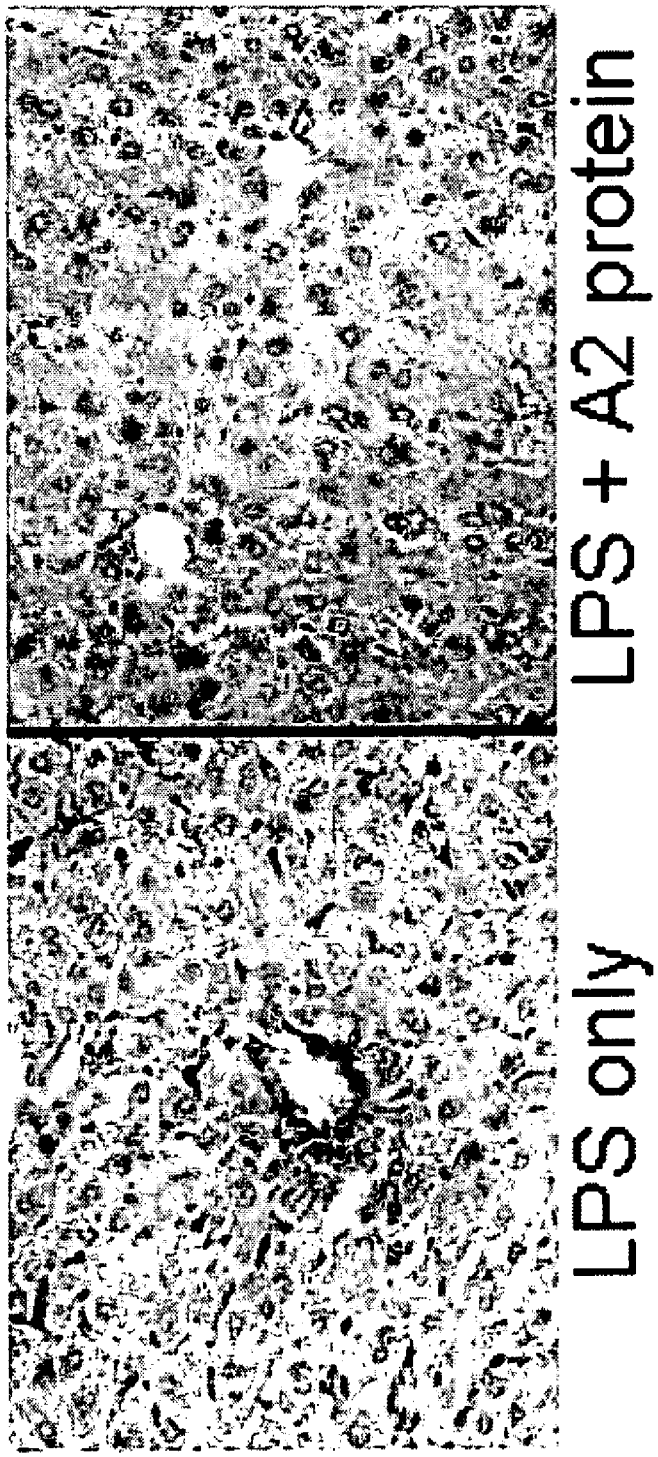
FIG. 9 demonstrates fibrin staining. Liver of mice at 12 hours after administration of LPS and/or A2 protein is demonstrated.

Protective Effects of Recombinant VWF-A2 Domain in LPS-Stimulated Mouse Model of Endotoxemia Previous results indicated that the A2 protein should have a beneficial effect on a mouse model of endotoxemia. Mice (C57BL/6J mice, 8-12 weeks old, 25-30 g) were used to analyze the effect of A2 in the presence of LPS. Some mice were pretreated with the A2 protein (10 mg/kg, intravenous) 5-10 min prior to the injection of LPS (50 or 5 mg/kg, intraperitoneal), other mice only were treated with either A2 protein or LPS only. In addition, some mice non-treated or treated with buffer/water were included as control. Twenty-four hours after the injections, all the animals were sick except those without LPS. At 36 h, it was noticed that the LPS+A2 protein mice had more activity (most of them comparable to the control animals), while the mice with LPS only were very sick and had no activity at all. In some experiments, several of these mice were dead after 36 h. After 96 h, the mice treated with A2 and LPS had the same activity as those from the control groups, showing a complete recovery (FIG. 6A). When low dose of LPS was used, less than 18% (compared with control) of the mice with LPS only survived 96 h (FIG. 6B), while 100% of those pre-treated with A2 protein survived. The animals were sacrificed at 96 h to examine the organs that are most affected during endotoxemia and sepsis. Striking differences were detected between mice with LPS only, LPS/A2 and buffer (none). For example, the mouse with LPS only had necrosis in the gastrointestinal tract, the liver was paled, and the kidneys were enlarged and discolored (FIGS. 7A and 7B). In another experiment, the mice were sacrificed at different time points (6, 24, 48, 72 and 96 h after injections) to determine the platelet counts, because thrombocytopenia is a common manifestation in endotoxemia. As shown in FIG. 8, at low dose of LPS, mice treated with LPS and A2 protein had a low platelet count during 36-48 h after the injections. Interestingly at 96 h, the platelet count for these animals was comparable to the control groups (FIG. 8). Finally, histologic studies showed more extensive fibrin deposition in the liver at 12 hours after LPS administration in mice treated with LPS only than the mice injected with LPS+A2 protein. Fibrin deposition was most pronounced in small and mid-sized vessels in the liver vasculature. FIG. 9 demonstrates the difference in fibrin deposition in liver between LPS only and LPS/A2 mice. In certain embodiments, survival studies are expanded to analyze the effectiveness of the recombinant VWF-A2 protein as a potential treatment for sepsis, while in additional aspects the effect of the A2 protein on inflammatory markers and microvascular thrombosis is analyzed using a mouse model of endotoxemia.

Example 5

Figure 10:
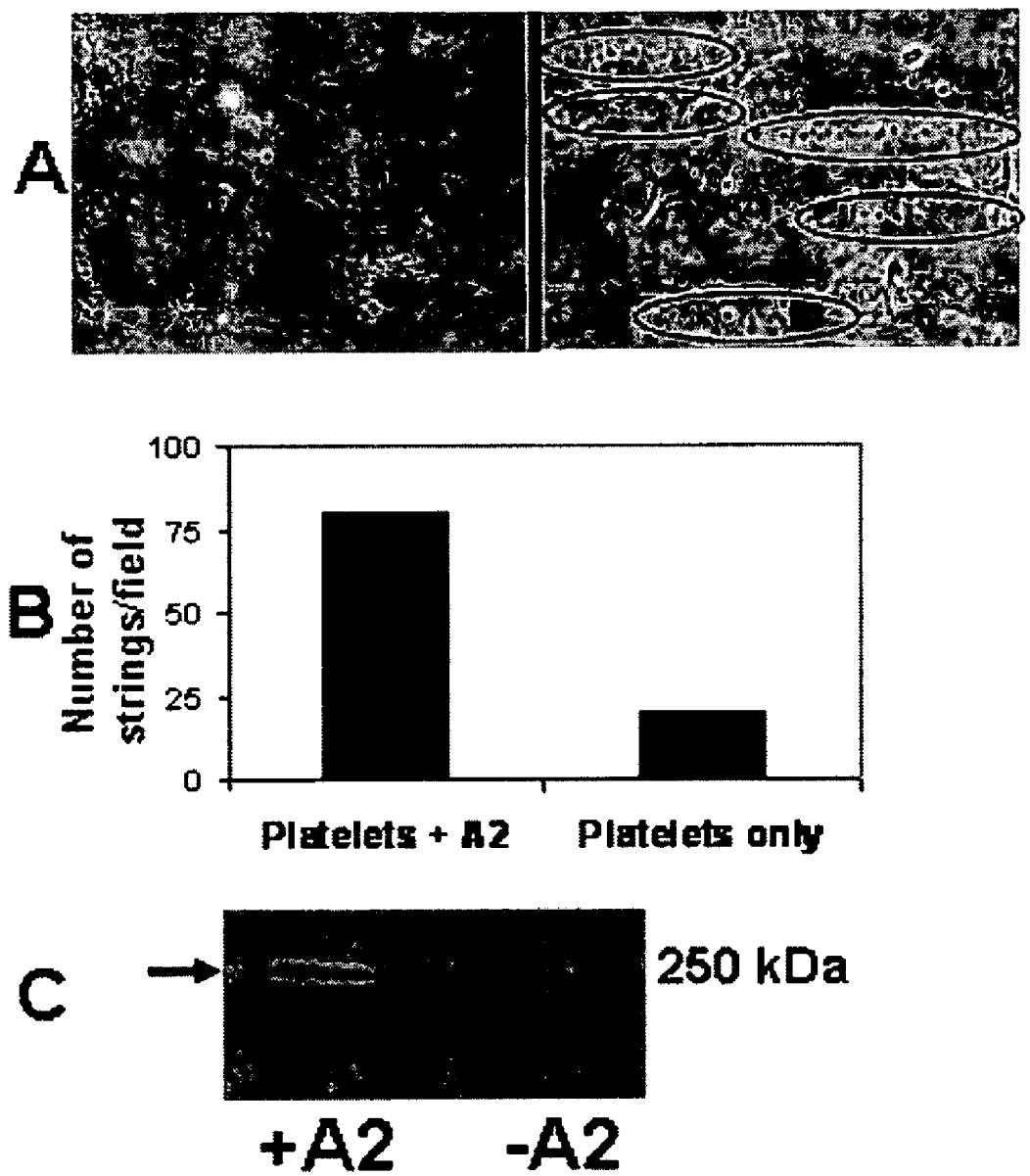
FIG. 10A shows that the HUVECs were perfused with washed normal platelets (suspended in Tyrodes buffer, left panel) or mixed with the A2 protein (right panel). Note the ULVWF-platelet strings inside the circles.
In FIG. 10B, after 2 min of perfusion, the number of ULVWF-platelet strings was counted in 20 contiguous fields.
FIG. 10C shows detection of VWF (arrow) in the supernatant from HUVECs incubated with the A2 protein. The VWF was analyzed by SDS-PAGE under reduced conditions and visualized by immunoblotting using an anti-VWF antibody.
Figure 11:
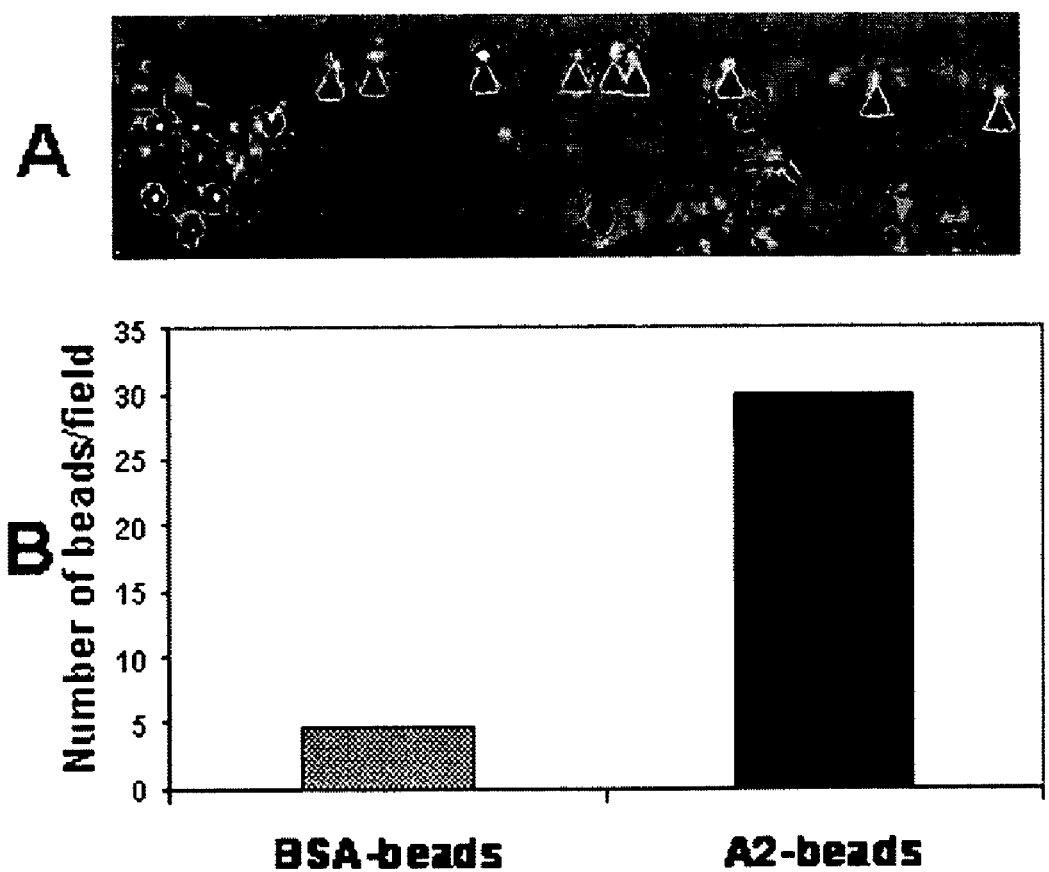
FIG. 11A shows that the HUVECs were perfused with beads coated with A2 protein followed by fixed platelets suspended in Tyrodes buffer. The bright spheres at the left of the photo are the beads bound to a cell. The arrowheads point to platelets attached to nascent ULVWF.

Recombinant VWF-A2 Domain Interacts with Human Umbilical Vein Endothelial Cells (HUVEC), Stimulating the Secretion of ULVWF To test if the A2 protein directly affects endothelial cells, the A2 protein (80 μg/ml) was added to a suspension of washed platelets and perfused over a surface of HUVEC. These experiments preclude the use of whole blood in order to exclude endogenous ADAMTS-13 and VWF. Unexpectedly, the number of ULVWF-platelet strings formed on the HUVEC surface was markedly increased in comparison to the control experiments (platelets+buffer) (FIGS. 10A and B), indicating that the A2 protein may stimulate the cells and induce the secretion of ULVWF. To test this embodiment, plates containing confluent HUVEC were incubated with buffer only or A2 protein (80 μg/ml) for 30 min. Then the conditioned medium was collected and examined by immunoblotting using an anti-VWF antibody (Dako). As shown in FIG. 9C, the A2 protein definitely stimulated the secretion of VWF. The ability of the A2 protein to bind to HUVEC was then tested. As described previously (REF), polystyrene beads were coated with the A2 protein (150 μg/ml) or bovine serum albumin (1%). First, plates with HUVEC were perfused with the A2-coated beads followed by a suspension of fixed-platelets (1×109/ml) to detect the formation ULVWF-platelets strings. In comparison with the control experiment (BSA-coated beads), a large number of A2-coated beads were observed to be firmly adhered on the cells and also ULVWF-platelet strings were observed (FIG. 11). These experiments clearly indicate that the isolated A2 domain of VWF is capable of not only binding HUVEC but also of stimulating the secretion of VWF. In certain embodiments, the interaction of the A2 protein with HUVEC is characterized, and it is identified where the cell surface protein(s) binds the A2 protein.

Example 6

Exemplary Research Design and Methods

The protective effect of recombinant VWF-A2 protein makes it a strong candidate as a novel therapy not only for sepsis but for other pathological conditions where microvascular thrombosis is one of the complications. The beneficial effect of the A2 protein in particular aspects is mediated by its interaction with endothelial cells that stimulates the cells, so this novel observation is further characterized, in specific embodiments. Therefore, the effects of VWF-A2 protein on mortality and organ dysfunction may be determined in a murine model of sepsis, for example.

Evaluate using Recombinant VWF-A2 Protein as a Therapy for Sepsis using a Mouse Model of Endotoxemia The novel observations obtained with the recombinant VWF-A2 domain in LPS-challenged mice indicated that this polypeptide has a therapeutic use in patients with sepsis. Although two different doses of LPS and A2 protein were used in some initial studies, this polypeptide notably improved the survival of the infected animal 100% (n=8) compared with control. In contrast, 18% (n=12) of the mice with LPS only survived the same number of days. Thus, in specific embodiments of the invention the most effective dose of the A2 protein that improves the survival of our mouse model of endotoxemia is characterized.

Figure 6:
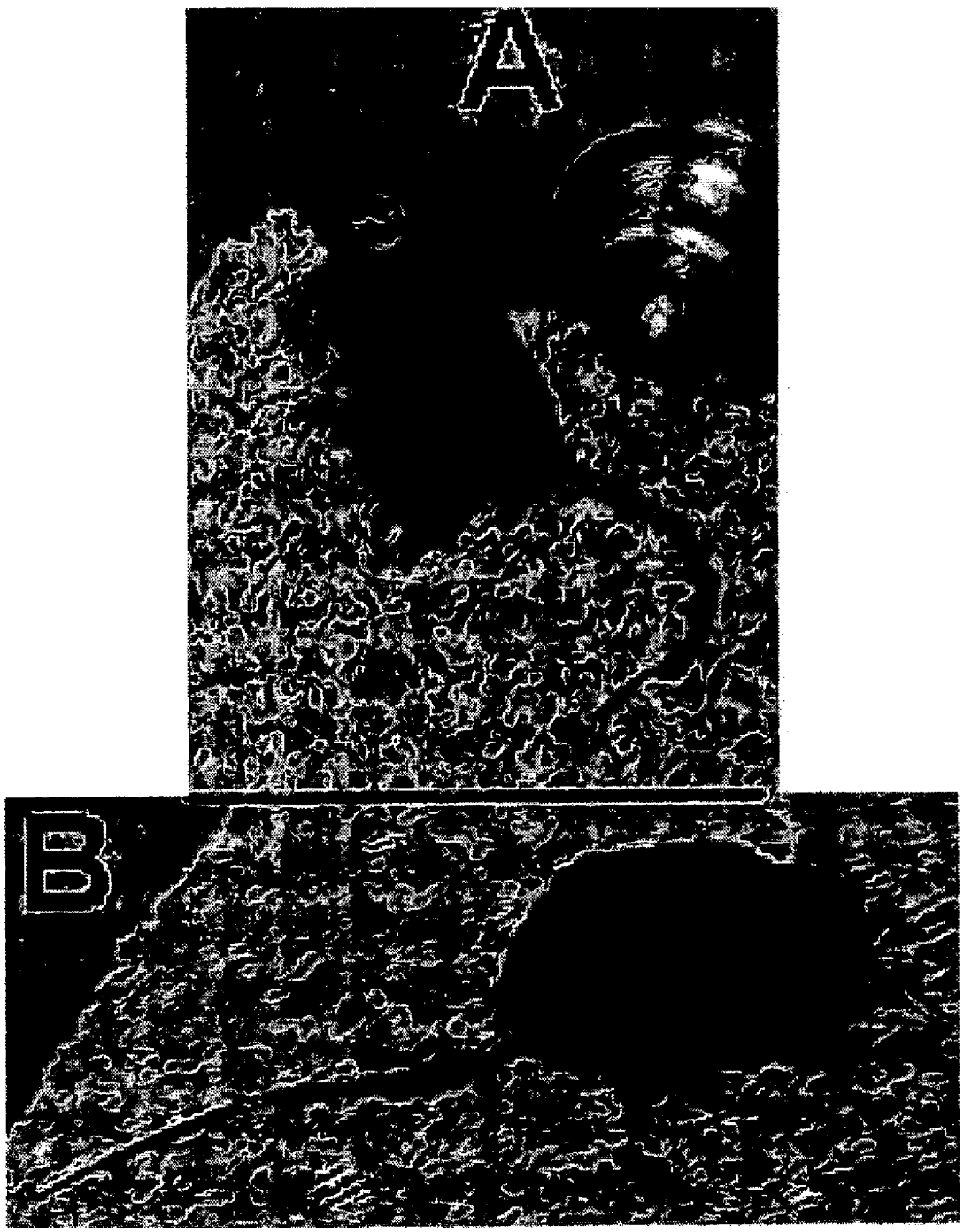
FIG. 6A demonstrates that after 96 h, the LPS-challenged mice pre-treated with the A2 protein (5 mg/kg) was as active as the control mice.
In FIG. 6B, some mice injected with LPS only died before or continued to be very sick at 96 h after the injections.

Exemplary survival studies may be as follows. The inventor demonstrated that the recombinant A2 domain polypeptide effectively rescued LPS-challenged mice (FIGS. 6 and 7). In initial studies, all of the mice injected only with the highest dose of LPS (50 mg/kg) died approximately between 24 and 36 h after injection. At lower dose of LPS (5 mg/kg) some of the animals lived (2 out of 5) until the last day of observation (day 6th). In this specific embodiment, the lowest and most effective dose of the A2 protein that will rescue the mice treated with 50 or 5 mg/kg dose of LPS is determined. Three exemplary different concentrations of the A2 protein (2, 5 or 10 mg/kg) are tested. Thus, this embodiment will carry out survival studies of mice treated with LPS and/or A2 protein for a period of time of 6 days. To assess survival, animals are monitored every 3 hours and euthanize any mouse in distress or with a body temperature of less than 36° C. measured with an infrared gun thermometer pointed to their abdomen. Previous observations have shown that all mice that reach this degree of hypothermia eventually die (Soothill et al., 1992; Kort et al., 1998). This has been confirmed by the inventor in initial studies. Survival studies are performed in C57BL/6J mice (8-12 weeks old, 25-30 g), purchased from the Jackson Laboratory, and maintained under a 12 h light/dark cycle at a controlled temperature (23±2° C.) with free access to food and tap water. In certain aspects, two different doses of LPS (50 or 5 mg/kg) are utilized. Three different exemplary doses of the A2 protein (2, 5 or 10 mg/kg, intra venous) are used in each LPS group. A2 is administered by intravenous tail vein injection 10 min prior the administration of LPS. LPS is administered by intraperitoneal injection. The exemplary controls are non-treated mice and animals treated with diluent of A2 protein (TBS-T) and LPS (water). Survival is monitored every 6 h until 144 h.

Similar survival studies are also performed injecting the A2 protein 3 or 6 h after LPS (50 or 5 mg/kg). It is noteworthy that mice with LPS only have demonstrated symptoms of illness (i.e. fever, reduced activity, ruffled hair) between 3 and 6 hours after the injection. Thus, these experiments allow determination if the A2 protein can prevent the clinical manifestations after initiation of the LPS induced inflammation.

In some embodiments there is variability of LPS potency, which has been recently reported (Rumbaut et al., 2006). It is known that even with using aliquots from the same batch of LPS, one can observe differences marked by the animal response. Therefore, in alternative embodiments, one may use cecal ligation puncture (CLP), which is a widely used experimental model that gives more consistent results and that closely mimics an acute infection/inflammation in humans (Corral et al., 2005). Basically, anesthetized animals are placed on a surgical board and the abdominal skin opened (2-cm midline incision) to allow exposure of the cecum with adjoining intestine. The cecum is tightly ligated below the ileo-cecal valve, and is punctured twice with an 18-gauge needle (top and bottom). The cecum is then squeezed to allow extrution of intestinal contents and then returned to the peritoneal cavity. The laparotomy site is then closed and animals observed for the length of the study.

Examine the Effect of Recombinant VWF-A2 Protein on LPS Induced Systemic Inflammation The mechanism by which the recombinant VWF-A2 protein rescues the mouse model of endotoxemia may be further characterized. One may examine the effect of the A2 protein on markers of inflammation (i.e. cytokines, chemokines and soluble cell adhesion molecules), whose expression levels are significantly increased in LPS-stimulated mouse model (Copeland et al., 2005). By identifying which markers are directly affected by the A2 protein, one can examine the markers' roles in the pathophysiology of sepsis.

Determine the Effect of A2 Proteins in Blood Cells

These studies may be done using the dose of LPS and A2 that most effectively affects morbidity and mortality (as determined as described elsewhere herein). One may use five groups of mice treated with LPS, A2 or LPS plus A2. A control non-treated mice or mice treated with buffer is employed (Table 1).

TABLE 1

| Five groups of mice treated differently | | | | |
|---|---|---|---|---|
| Group 1 | Group 2 | Group 3 | Group 4 | Group 5 |
| LPS only | LPS + A2 | A2 only | Vehicles | none |

Although no phenotypical difference was observed between mice treated with A2 protein, they may be included because in vitro observations indicate that the A2 protein stimulates HUVEC and because this can open up the possibility of detecting changes of some anti- or proinflammatory mediators in plasma induced by A2 alone. Blood is drawn from the inferior vena cava into a syringe containing 3.8% sodium citrate. The platelet and leukocyte counts and activation markers are determined by flow cytometry, red blood cell count and hematocrit by automated cell counter. The morphology of the cells is analyzed on peripheral blood cell smear stained with Wright-Giemsa. The remaining of the blood is centrifuged to obtain plasma that is stored at −80° C. for the analysis outlined in subsequent embodiments.

Determine the Effect of the A2 Protein on Markers of Inflammation (I.e. Cytokines, Chemokines and Soluble Cell Adhesion Molecules Inflammatory markers are measured in C57BL/6J injected with LPS at 0, 2, 4, 8, 10 and 24 h post the injections. The time points are chosen based on recent reports that indicate that LPS triggers the release of inflammatory markers in a rather acute fashion. Increased levels of cytokines (interleukin (IL)-1β, IL-6, and tumor necrosis factor alpha (TNF-α(Copeland et al., 2005) as well as chemokines, keratinocyte-derived chemokine (KC) and macrophage inflammatory protein-2 (MIP-2) can be observed only after 2 hours of intraperitoneal injection of LPS. These time points are useful to monitor the progression of the disease and the effect of the recombinant VWF-A2 protein on these markers. Commercially available ELISA kits may be employed for mice to measure cytokines and chemokines including the most common markers for sepsis such as TNF-α, IL-β, IL-6, IL-8, IL-10, IL-12 p70, RANTES, KC and macrophage inflammatory protein (MIP)-2. In specific embodiments, there is a significant difference between mice treated with A2 versus the ones untreated (LPS only).

Examine the Effect of Recombinant VWF-A2 Protein on Cell Adhesion Molecules In Vivo Sepsis also results in the release in plasma of soluble forms of adhesion and inflammatory molecules in relation to endothelial cell activation. They are involved in leukocyte recruitment and transmigration and are responsible for the inflammatory reactions of vulnerable organs such as lung, liver, kidney and peritoneum (Springer, 1994). It has been observed in vitro experiments that the A2 protein significantly reversed the effect of LPS on the translocation of leukocytes over a surface of endothelial cells under flow conditions (FIG. 5), indicating that the A2 protein in some way interrupts the interaction between leukocytes and activated endothelial cells. The interaction between leukocytes and endothelial cells may be mediated by the intercellular adhesion molecule (ICAM)-1, vascular cell adhesion molecule (VCAM)-1, E-selectin and P-selectin. In some aspects, the A2 protein blocks this interaction by making a direct contact to at least one of these molecules or by down regulating their cell membrane expression. Thus, levels of the soluble forms of these adhesion molecules are measured in mice from the same five groups using commercially available ELISA kits. In specific embodiments, treatment with A2 results in a reduction in the expression of adhesion molecules.

Analyze ADAMTS-13 and VWF

Figure 5:
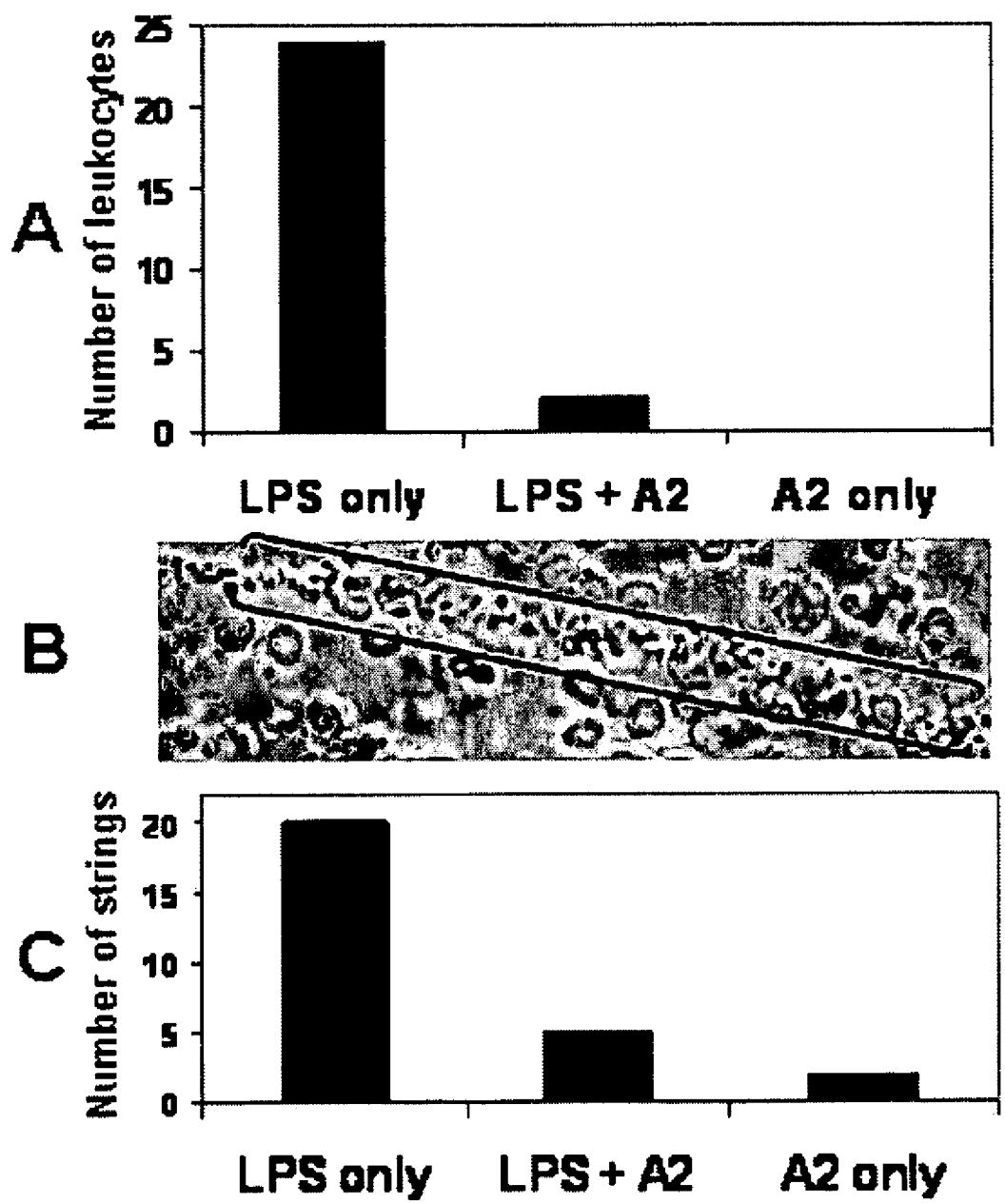
FIGS. 5A-5C shows HUVECs grown on culture dishes that became the bottom of the flow chamber.

Very recently, it was reported that the activity of the enzyme ADAMTS-13 is decreased during sepsis (Ono et al., 2006). In fact, a large number of platelets has been observed attached to strings of ULVWF when whole blood containing LPS was perfused over a surface of endothelial cells (FIG. 5). In contrast, the presence of the A2 protein effectively reduced the formation of ULVWF-platelet strings (FIG. 5). Therefore, the effect of the A2 protein on ADAMTS-13 activity is investigated using an in vivo model for sepsis, determining the enzyme activity in the plasma samples collected at the different time points described above. Cleavage activity is determined in plasma using an ELISA method that was previously described (Whitelock et al., 2004), which is also effective for murine ADAMTS-13. Additionally, ADAMTS-13 antigen levels are measured. Currently, there is only one antibody available that reacts with both human and murine ADAMTS-13, limiting the possibility of using a capture ELISA technique that would be a simple method to measure antigen levels. Thus, ADAMTS-13 is measured in plasma by Western Blot and densitometry (Dong et al., 2004). ADAMTS-13 is detected using the antibody 157 (Bethyl Co., The Woodlands, Tex.).

Low activity of ADAMTS-13 also correlates with increased levels of ULVWF. Thus, the multimeric pattern of VWF is examined following an SDS-agarose electrophoresis method that is already known for its use with mice plasma.

The observation that A2 stimulates secretion of ULVWF in HUVEC (FIG. 10) may seem to contradict the certain embodiment that A2 prevents thrombosis. However, the interaction of A2 protein with endothelial cells may be stimulating the secretion of ADAMTS-13. In fact, a very recent study described that endothelial cells synthesize ADAMTS-13 (Turner et al., 2006). Nevertheless, it is investigated whether the combination of A2 protein and LPS induce an exaggerated increment of plasma VWF. This is done in plasma obtained from the five groups of mice at the 6 time points.

Quantitation of mRNA in Tissues using Real Time RT-PCR

It is also analyzed whether the changes in plasma concentration of the cytokines, chemokines and soluble cell adhesion molecules reflect the corresponding changes in messenger RNA content. Thus, real time reverse-transcription polymerase chain reaction (RT-PCR) is performed to analyze the presence and quantity of mRNA for the corresponding testing molecule.

Anesthetized mice are sacrificed, the chest opened, the cardiovascular system perfused, a sample of different tissues harvested (kidney, adrenal, liver, lung, heart and gut) and snap frozen in liquid nitrogen. Total RNA is extracted from pulverized frozen (−80° C.) mouse tissues using the TRIzol®Reagent (Invitrogen) according to the manufacturer's instructions. RNA integrity is assessed by formaldehyde gel electrophoresis and A260/A280 absorbance ratio. One microgram of total RNA is used to synthesize cDNA using oligo (dT) primers with the Advantage™ RT—for PCR kit (BD Biosciences). Five ng of cDNA is then used for the 40 cycles of PCR amplification (95° C., 15 sec; 60° C., 1 min) in a 20 μl-reaction mixture (SYBR®Green PCR Master Mix, Applied Biosystems) containing 300-900 nM of each mouse-specific forward and reverse primers. The primers for the cytokines, chemokines and cell adhesion molecules to be tested in this sub-aim are commercially available. Real-time amplification data is collected by an ABI Prism 7700 Sequence Detection System (Applied Biosystems) and analyzed using its accompanying Sequence Detector System (SDS) 1.9.1. software. During the primer optimization steps, DNA agarose gels are run after the RT-PCR reactions to corroborate the specificity of the reaction. Samples will be run in triplicates.

Immunohistochemical Analyses for VWF, Fibrin and A2 Protein

Systemic microvascular thrombosis is present in severe cases of sepsis. Post-mortem studies demonstrate microvascular thrombi in many organs including the kidney, liver, lung, gut, and adrenals (Dixon, 2004). The initial data indicates that the administration of A2 protein inhibits thrombus formation in the LPS-challenged mice (FIG. 9). It is also observed that in vitro the A2 protein blocks platelet adhesion to fibrin (FIG. 3). These observations indicate that the inhibitory mechanism works via the binding to deposited fibrin. To achieve this, one can harvest a piece of the organs that are most likely involved in sepsis and perform histological analysis. The differences in fibrin and VWF deposition is determined between the organs from A2 treated mice and compare with controls. The localization of the A2 protein is also determined in the tissues by immunofluorescence using an anti-histidine tag antibody. It is anticipated that the A2 protein co-localizes with VWF and/or fibrin.

Study the Effect of Recombinant VWF-A2 Protein on Platelets and Leukocytes in Endotoxemia It is well-established that several inflammatory stimuli induce translocation and adhesive cell-cell interactions between platelet, leucocytes and endothelial cells (Cerwinka et al., 2002; Katayama et al., 2000) and formation of microthrombi. In this embodiment, it is investigated if the recombinant VWF-A2 protein impairs the adhesion of platelet and leucocytes to endothelial cells and if the protein affects the formation of thrombi. An animal model may be used, and the effect of the A2 protein is examined in adhesion and thrombosis by intravital microscopy. Methods for intravital microscopy to study mice treated with LPS may be employed (Rumbaut et al., 2006), including a procedure that has been previously described (Rumbaut et al., 2006; Rumbaut et al., 2004).

Male mice are injected with A2 protein (5 or 10 mg/kg/IV) and/or LPS (50 or 5 mg/kg/IP) 2 or 4 h before the experiments. Then, mice are anesthetized with pentobarbital sodium (50 mg/kg/IP), with additional doses (12.5 mg/kg) as needed. The mice are then placed on a custom Plexiglas tray and maintained at 37° C. with a homeothermic blanket and monitored with a rectal temperature probe. Mice are intubated, the internal jugular vein cannuladed or intravenous drug administration and the common carotid artery cannulated and blood pressure is monitored. To exteriorize the cremaster muscle a midline incision is made through the skin and fascia, and the cremaster muscle dissected from the connective tissue. The exposed muscle is pinned on a Sylgard (Dow) pedestal, and open from the apex to the inguinal canal. Then, the edges are pinned radially in order to expose the muscle open and the connective tissue between the cremaster and the epididymis dissected. After that, the testis and epididymis are pushed back into the abdominal cavity. Throughout the experiment, the cremaster is superfused with bicarbonate-buffered saline at the rate of 5 ml/min. The buffer are bubbled continuously with a 95% $N_2$-5% $CO_2$ gas mixture to maintain a pH between 7.35 and 7.45. The temperature of the buffer at the tissue interface is maintained at 35° C. The $PO_2$ of the superfusate at the tissue interface measured with an oxygen electrode (Microelectrodes) will be maintained at ~20 mmHg. The preparation is then transferred to the stage of an upright intravital videomicroscope (BX-50, Olympus). A x4 (numerical aperature 0.13) objective is used to survey the microvascular preparation for second- and third-order venules. Visualization of individual microvessels and formation of thrombosis is done with a x40 water immersion objective (numerical aperature 0.8). A video camera mounted on the microscope (Hitachi KP-M1AN) projects the transilluminated image onto a monitor, and the image is recorded using a videocassette recorder. Internal vessel diameters are recorded throughout the experiment with video analysis software (Image 1.6, NIH).

To study thrombosis, one may use 20 mice per group (donors are not required). In this ex vivo model, a light/dye injury of microvessel endothelium induces adhesion and aggregation of platelets, with platelet thrombus formation occurring in the absence of endothelial denudation (Rumbaut et al., 2004). Here, the microvascular thrombosis model is applied to determine whether the A2 protein modifies the rate of formation of microvascular thrombi in vivo during endotoxemia. The average times are compared to form a platelet thrombi in mice treated with either vehicle, LPS and/or A2 protein administered 2 or 4 h before the experiments. It is anticipated that in the LPS-challenged mice the A2 protein will increase the time required for onset of thrombus formation and cessation of flow.

To study cell adhesion, 20 mice per group plus 6 more mice may be employed that is used as platelet donors. The platelet-endothelial and leukocyte-endothelial adhesion is investigated in the same animal. Five groups of mice are tested as described in Table 1.

It is evaluated if the A2 protein reverses the effect of LPS by reducing the number of adherent platelets and leukocytes (Rumbaut et al., 2006). In these experiments, one can monitor adhesion of exogenously administered fluorescently labeled platelets in the absence of light/dye injury (Rumbaut et al., 2006). For these studies, blood is drawn from a donor mouse and the platelets are isolated, labeled ex vivo with a fluorescent dye, and infused intravenously to the recipient mouse (Rumbaut et al., 2006). Leukocyte adherence is evaluated by transillumination. The number of platelets or leukocytes adhered onto a defined area is compared between mice treated with LPS and/or A2 protein or vehicle only.

Characterize the Interaction of the VWF-A2 Domain with Endothelial Cells

During a systemic inflammatory reaction such as seen in endotoxemia and sepsis, the interaction of extracellular mediators with their receptors on EC leads to activation of signaling pathways, up-regulation of cell adhesion molecules, release of cytokines, increased expression of procoagulants and/or reduced expression of anti-coagulants (Aird, 2003). The beneficial effect observed from the A2 protein in the presence of LPS, indicates that the protein works by counteracting some of the effects induced by endothelia cell activation. LPS may induce thrombosis by down-regulation of EPCR and thrombomodulin (TM) that are expressed by activated endothelial cells (Li et al., 2005; Iwaki et al., 2005). It is investigated if the A2 protein is capable of reversing this effect in LPS-challenged mice treated with A2 protein. As mentioned above, in vitro studies indicated that the recombinant VWF-A2 protein stimulates secretion of VWF (FIG. 10). This observation indicates that A2 promotes thrombosis; however this study was done in vitro using washed platelets that do not contain endogenous ADAMTS-13 or plasma. Nevertheless, A2 may be interacting with endothelial cells and stimulate the release of ADAMTS-13 at the same time (Turner et al., 2006). This embodiment is evaluated in vivo using an animal model.

Identification of the Receptor(s) for the A2 Protein in Endothelial Cells

In this embodiment, the membrane proteins of endothelial cells are isolated to identify which of them show an apparent binding activity for the A2 protein. A2-affinity column chromatography is used to capture and isolate the potential membrane proteins. The eluted proteins are analyzed by SDS-PAGE and identified using mass spectrometry (MS).

Ten T75 cm$^2$ flasks of 90-95% confluent cells are washed with ice-cold buffer (PBS), collected with a cell scraper, centrifuged, and the pellets collected. The cell pellet is then suspended in buffer (10 mM Tris-HCl, 1.5 mM EDTA, 12 mM monothioglycerol, 10 mM sodium molybdate, 10% glycerol, 0.1% Triton X-100) with protease inhibitors (10 μg/ml leupeptin, 1 mM phenyl-methylsulfonyl fluoride, 10 μg/ml aprotinin, 1 μg/ml pepstatin). After homogenization on ice (sonication), the sample is centrifuged at 12,000×g for 10 min at 4° C. and the supernatant removed. The supernatant is then centrifuged at 100,000×g for 2 hr at 4° C. The pellet (membrane fraction) is resuspended in PBS containing 0.1% Tween-20. Then, this soluble membrane fraction is passed through an A2-affinity column (1 ml of beads immobilized with recombinant VWF-A2 protein). The column is washed with the running buffer and the bound proteins are eluted using 0.5, 1.0 or 2.0 M sodium chloride. To assure the removal of all the bound proteins a last elution will be performed with a buffer pH ~2.9. This last fraction is then equilibrated with another buffer to raise the pH to ~7.0. The collected fractions is analyzed in SDS-PAGE, the bands are visualized using either Coomassie blue or silver stain and each of these bands are excised for mass spectrometry (MS) analysis for protein identification. The excised membrane is subjected to trypsin digestion, and an aliquot of the peptides generated from the digestion are spotted onto MS target plates and mixed with the appropriate matrix for MS/MS analysis by MALDI-tof/tof on the Applied Biosystem 4800 mass spectrometer.

In certain aspects of the invention, the site recognized by the A2 protein in the potential receptor remains intact after electrophoresis. Thus, alternatively, the proteins from the cell membrane fraction are resolved under reducing- or non-reducing conditions by SDS-PAGE in duplicate and transferred to a membrane. This membrane is then cut, staining one half with Coomassie blue or silver stain, and the other half is incubated with 5% milk to block the membrane. Then, this half of the membrane is probed with the A2 protein and the bound A2 is detected using an anti-histidine tag antibody horse radish peroxidase (HRP) conjugated (Cruz et al., 2003). By chemiluminescence technique, the resultant (bands) spots in the X-ray film are then matched with the stained membrane, allowing excision of it from the membrane for the identification of the proteins. The identified proteins can further be validated by obtaining antibodies for these proteins and using techniques such as Western blotting and ELISA. In addition, the antibodies against the resultant identified protein(s) can be used to block the binding activity of the A2 protein to endothelial cells and/or to perform immunoprecipitation assays to confirm the interaction between the A2 protein and its receptor.

In the event that two or more proteins co-migrate in the SDS-PAGE, the sample is resolved in a two-dimensional gel electrophoresis. The bands are analyzed as described above.

Because it has been observed that the A2 protein reduced both platelet and leukocyte interaction with endothelial cells in vitro under flow conditions, it is examined if the A2 protein contains binding activity for one the following receptors: E-selectin, P-selectin, ICAM-1, and VCAM-1. These receptors have been reported to play a role in mediating the platelet- and leukocyte-endothelial interaction. As previously reported (Morales et al., 2006; Cruz et al., 2005), the binding is tested of the recombinant form of each of the four human cell adhesion molecule (R&D System) to VWF-A2 protein using surface plasmon resonance (SPR). The Biacore® 2000 (SPR) instrument may be employed, and in the case that a specific interaction is observed between the cell adhesion molecule and the A2 protein, one may proceed to determine equilibrium association (Kon) and dissociation (Koff) rate constants and KD. First, the recombinant A2 protein is captured via its histidine-tag onto a chip coated with nickel. After equilibration with the running buffer, each recombinant cell adhesion molecule is perfused at different concentrations. The chip is then regenerated with 50 mM EDTA.

Alternatively, one may examine whether function-blocking monoclonal antibodies against each of these receptors (E-selectin, P-selectin, ICAM-1, and VCAM-1), are capable of inhibiting the interaction of the A2 protein with endothelial cells using a method of immunofluorescence. Cells exhibiting fluorescence under the FITC filter are considered to have stained positive for the A2 protein. Substitution of the first antibody with an irrelevant IgG molecule at the same concentration as the anti-receptors' antibodies may be used as a positive control or total binding for A2 protein. In comparison with the positive control slide, a diminished fluorescence signal indicates that the antibody used in that particular experiment impaired the binding of the A2 protein.

The A2 protein bound to endothelial cells is detected by the following procedure: endothelial cells are seeded onto coverslips and allowed to attach. The cells are washed with PBS and treated with histamine (100 μM) to stimulate the expression of the adhesion molecules prior to fixation. Then, the cells are fixed in 1% p-formaldehyde in PBS, and treated with Triton X-100 (0.1% in PBS). Cells are incubated with one of the antibodies against the receptors in PBS for 2 hours, rinsed in PBS three times, and then incubated with the A2 protein in PBS for 1 hour. After another washing, a chicken anti-histidine tag antibody FITC conjugated is added and incubated for 1 h. Coverslips are rinsed in PBS three times and mounted on microscope slides. All the above procedures are performed at room temperature.

Another alternative approach that may be utilized is described in FIG. 11. In this case, plates containing confluent endothelial cells are incubated with one of the monoclonal antibodies for the receptors for one hour, followed by the perfusion of A2-coated beads. The number of beads attached between cells treated with the anti-receptor antibody or irrelevant IgG molecule is compared, the latter representing a positive control (total binding) for A2 protein.

Interestingly, both LPS and A2 protein interact with EC stimulating the secretion of VWF. In specific embodiments, then, they share the same receptor in EC and the A2 protein blocks the binding of LPS to this receptor. One of the LPS receptors well studied is the TLR-4. Therefore, the possibility that the A2 binds to TLR-4 is examined using the methods described for the cell adhesion molecules elsewhere herein. Antibodies against TLR-4 and the recombinant form for TLR-4 are commercially available (R&D Systems).

Examine the Effect of Recombinant VWF-A2 Protein on the Expression of Cytokines, Chemokines and Cell Adhesion Molecules in HUVEC Activation of vascular endothelium by LPS results in EC production of various proinflammatory molecules, including soluble cytokines and chemokines (Pober and Cotran, 1990; Mantovani et al., 1992). Here, the effect of recombinant VWF-A2 domain on the expression of some of the most common cytokines and chemokines in HUVEC stimulated with LPS is analyzed. These are IL-1, IL-6, IL-8, MCP-1, eNOS, granulocyte-macrophage colony stimulating factor (GM-CSF), and fractalkine (CX3CL1) (Weglarz et al., 2003; Hatakeyama et al., 2004; Klein et al., 2000; Cardaropoli et al., 2003). The cells will be seeded in 12-well plates and grown until confluence. The cells will be incubated for 0, 2, 4, 8 or 24 h with LPS (100 ng/ml) and/or A2 protein (80 μg/ml). The concentration of LPS is based on previous reports that describe that the production of some of the cytokines by HUVEC reach the peak level with that dose (Zeuke et al., 2002; Frankel et al., 2006), and the effectiveness of that concentration of the A2 protein in activating the cells is shown herein (FIG. 10). In each experiment, control HUVEC is included to determine basal expression of the testing inflammatory markers. Supernatants are collected and assessed for the production of the respective inflammatory markers by using commercially available ELISA kits (Invitrogen and R&D Systems). These assays are performed according to the manufacturer's instructions.

In addition to using ELISA kits, the expression levels of E-selectin, P-selectin, ICAM-1 and VCAM-1 in HUVEC are examined by flow cytometry. HUVEC are seeded in six-well plates and after growing to confluency, cells are incubated with LPS and/or A2 protein for 2 or 6 h. The mean fluorescence values corresponding to the cell adhesion molecules in non treated cells is compared with those from cells treated with LPS, LPS/A2, or A2 only.

Cells are harvested with a cell dissociation solution and washed with PBS and resuspended in 100 μl PBS. Cells are then incubated with the primary antibody (against one of the receptors) for 30 min. After washing, the cells are incubated with a secondary FITC labeled antibody for 30 min. After another wash, the cells are resuspendend in PBS containing 1.5% paraformaldehyde and analyzed by FACS.

Analyze the Expression Levels of mRNA of Inflammatory Markers in HUVEC

In certain embodiments of the invention, there is a correlation between the protein concentration and the expression levels of mRNA as a consequence of the treatment with the A2 protein and/or LPS in HUVEC. For this purpose, HUVEC cells are incubated 0, 2, 4, 8 or 24 h with LPS and/or A2 protein as described elsewhere herein. Total RNA is extracted from HUVEC using the TRIzol® reagent according to the manufacturer's instructions and analyzed as described elsewhere herein. mRNA levels are determined for IL-1, IL-6, IL-8, MCP-1, eNOS, GM-CSF, fractalkine (CX3CL1), E- and P-selectin, ICAM-1, VCAM-1, and TLR-4. The primer pairs for each of these proteins are commercially available (R&D Systems). In addition, as mentioned earlier, one may analyze ADAMTS-13, VWF, TM and EPCR. Primer pairs for ADAMTS-13 and VWF may be utilized as reported (Turner et al., 2006). In addition, primers for Glyceraldehyde-3-phosphate dehydrogenase (GAPDH) may be used for detection of a housekeeping gene in HUVEC. The primers for TM and EPCR have been described elsewhere (Murugesan et al., 2000; Feistritzer et al., 2003).

Following are exemplary primers for use in RT-PCR:

```
1) Forward primer ADAMTS13 Tsp1
GACAGTTACCCCCAACCTGA              (SEQ ID NO: 4)

Reverse primer
TGGATGTCAGCATCTTCCTG,             (SEQ ID NO: 5)
product size = 246 bp.

2) Forward primer ADAMTS13 CUB
AGCCAACAGGAACCATTGAC              (SEQ ID NO: 6)

Reverse primer
GCTTCCTGCACATCTTCCTC,             (SEQ ID NO: 7)
product size = 172 bp.

3) Forward primer VWF
AAGCCAATATAGGGCCTCGT              (SEQ ID NO: 8)

Reverse primer
CTCAGCAAATGGGCTTTCTC,             (SEQ ID NO: 9)
product size = 109 bp.

4) Forward primer GAPDH:
AGGGGAGATTCAGTGTGGTG              (SEQ ID NO: 10)

Reverse primer
CGACCACTTTGTCAAGCTCA,             (SEQ ID NO: 11)
product size = 202 bp.
```

```
-continued
5) Forward primer EPCR:
GGCAGTTTCATCATTGCTGG              (SEQ ID NO: 12)

Reverse primer
TTGAACGCCTCAGGTGATTC,             (SEQ ID NO: 13)
product size = 409 bp.

6) Forward primer TM:
TCCCCTCGGCTTACAGCTAATG            (SEQ ID NO: 14)

Reverse primer
TGGTACTCGCAGTTGGCTCTGAAG,         (SEQ ID NO: 15)
product size = 483 bp.
```

Example 7

Recombinant Von Willebrand Factor A2 Domain Polypeptide Interacts with the A1 Domain in VWF and Inhibits Platelet Adhesion Under High Flow Conditions Platelet adhesion at sites of vascular injury contributes to the arrest of bleeding as well as to the pathologic occlusion of diseased vessels under elevated shear stress. Under high shear stress, the platelet-von Willebrand factor (VWF) interaction is essential for platelet adhesion.

Mature VWF consists of a 2,050-residue subunit that contains multiple copies of A, B, C, and D type domains that are arranged in the order D'-D3-A1-A2-A3-D4-B1-B2-B3-C1-C2-CK (cystine knot)(Sadler, 1998; Verweij et al., 1986; Shelton-Inloes et al., 1986). The central portion of the VWF subunit contains a triplicate repeat sequence, or A domains. The A1 domain contains binding sites for GPIbα, heparin, sulfatides and collagen (Cruz et al., 2000; Mohri et al., 1989; Borthakur et al., 2000; Mazzucato et al., 1999; Morales et al., 2006). Its homologous A3 domain only binds to collagen fibrils types I and III, while the A2 domain contains the cleavage site for the metalloprotease ADAMTS-13 (Cruz et al., 1995; Lankhof et al., 1996; Cruz et al., 2003).

The relationship between the three A domains in VWF is not well defined. However, there are reports that indirectly imply a close relationship between the A2 and the A1 domains. For example, one study demonstrated that deletion of the A2 domain in VWF increased ristocetin-induced GPIb binding (Lankhof et al., 1997), indicating that the A2 domain may regulates the binding of its neighboring A1 domain to platelets GPIbα. In addition, another study indicated that the A1 domain in VWF inhibits the cleavage of the A2 domain, and that the interaction of A1 domain with platelet GPIbα terminates such inhibition, making the A2 domain more susceptible to be cleaved by ADAMTS-13 (Nishio et al., 2004). These reports indicate that a reciprocal regulatory function between the two A domains may be mediated through a direct contact.

Therefore, in this study the inventor has used recombinant polypeptides to characterize interaction between the A1 and A2 domains. The results obtained in this study indicate that a direct interaction of the A2 domain with the adjacent A1 domain in VWF inhibits the binding to GPIb, in certain embodiments.

Example 8

Figure 12:
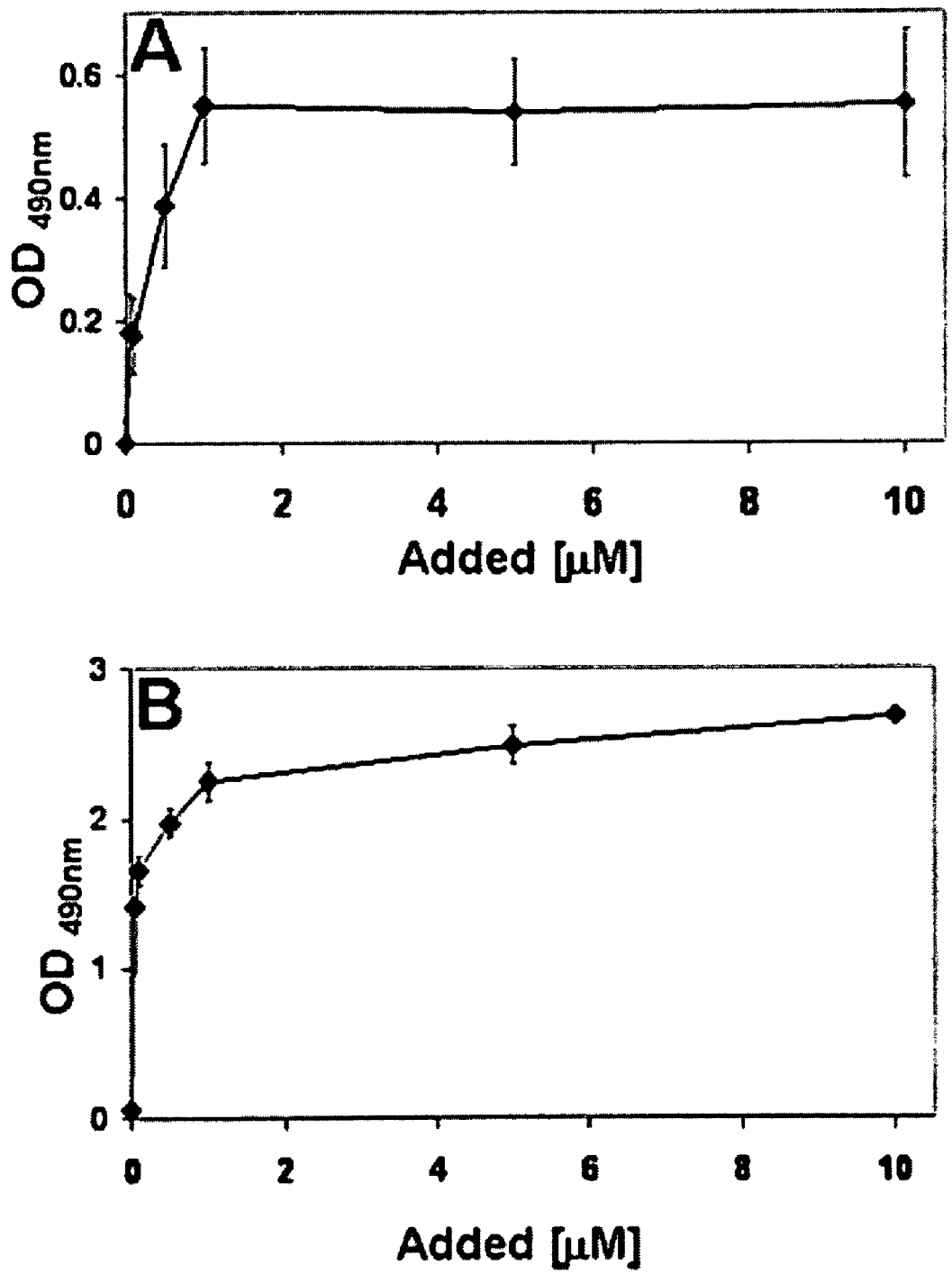
FIGS. 12A-12B demonstrate saturable binding of recombinant VWF-A2 domain to VWF or A1 domain polypeptide.
Figure 13:
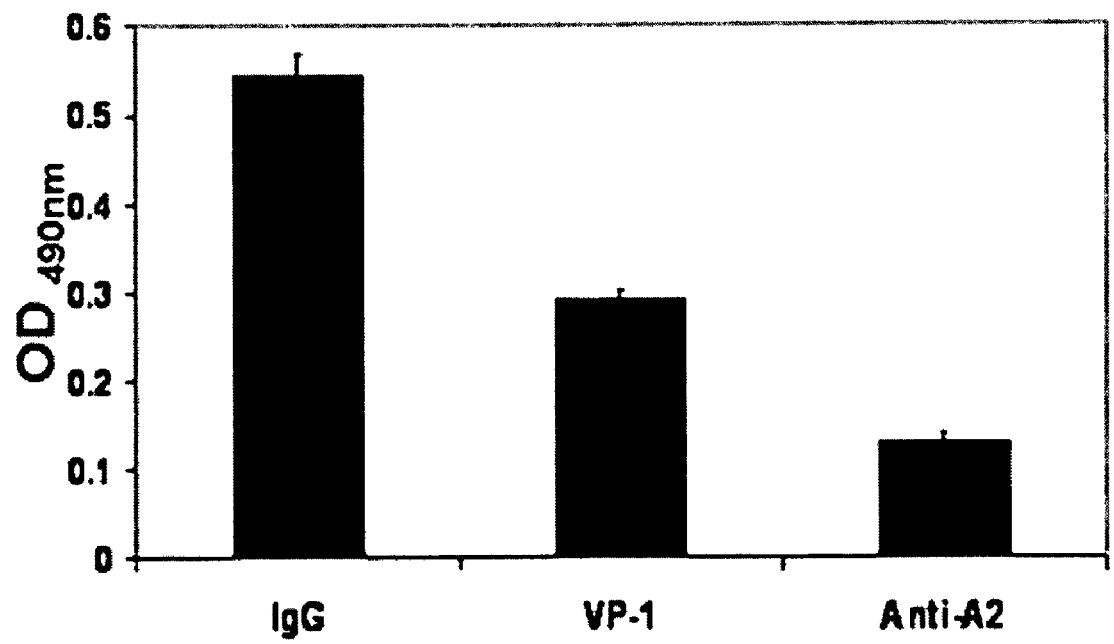
FIG. 13 illustrates antibody blocking of VWF-A2 polypeptide binding to VWF. Monoclonal antibodies Anti-A2 and VP-1 were tested for their ability to inhibit the binding of A2 polypeptide to immobilized full length VWF. The VWF-A2 protein (0.3 µM) was pre-incubated with either antibody (10 µg/ml) for 10 min and then tested in the VWF-binding assay. Each column represents the mean±S.D. of six determinations.

Recombinant A2 Domain Polypeptide Specifically Interacts with the A1 Domain in VWF As previously described (Morales et al., 2006; Cruz et al., 1995; Cruz et al., 2003), both recombinants A domains were monomeric when analyzed by SDS/PAGE under nonreducing conditions, excluding the possibility of disulfide-mediated oligomerization or aggregation (not shown). First, the capacity of the recombinant A2 domain polypeptide to bind immobilized recombinant A1 domain polypeptide is tested. As shown in FIG. 12B, the A2 domain bound to immobilized A1 domain in a concentration-dependent and saturable manner with a half-maximal binding observed at ~0.065 µM. Similarly, the A1 polypeptide bound to immobilized A2 domain with a comparable half-maximal binding of ~0.05 µM. Next, the ability of the A2 domain polypeptide to bind to the A1 domain in full length VWF was tested. FIG. 12A demonstrates that the A2 domain polypeptide specifically bound to immobilized VWF. The half-maximal binding occurred at approximately 0.2 µM. Alternatively, the A1 domain polypeptide bound to immobilized VWF with a binding activity higher than the A2 protein, probably because there is another recognition site for the A1 domain within D'D3 domains (Ulrichts et al., 2006). As shown in FIG. 13, the interaction of the A2 domain polypeptide to VWF was effectively inhibited by monoclonal antibodies against human VWF-A2 domain, Anti-A2 and VP-1 (75% and 45% inhibition, respectively).

Figure 14:
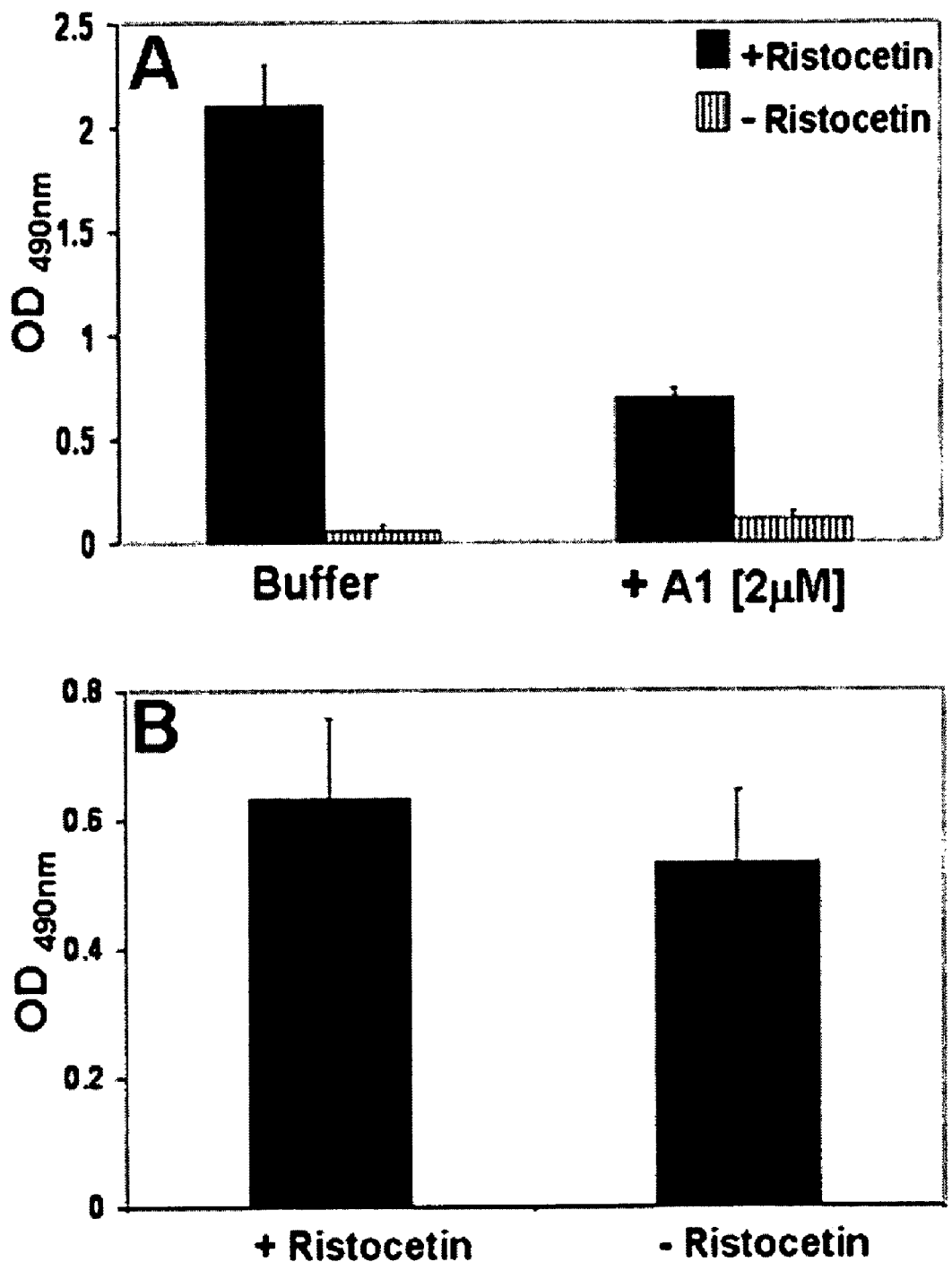
FIGS. 14A-14B show binding of VWF or ULVWF to immobilized recombinant VWF-A2 domain polypeptide.

The observation in which the A2 domain polypeptide specifically bound to immobilized A1 polypeptide or multimeric VWF, indicated that the A2 polypeptide recognizes only the active form of the A1 domain. To determine whether the A2 protein specifically interacts with the activated form of multimeric VWF, the binding of VWF to immobilized A2 domain polypeptide was examined with or without the modulator ristocetin. The multimeric VWF efficiently bound to the immobilized A2 domain polypeptide only in the presence of ristocetin (0.5 mg/ml) (FIG. 14A). The involvement of the A1 domain in the interaction between VWF and the A2 domain polypeptide was further demonstrated when the A1 domain polypeptide (2 µM) effectively blocked the ristocetin-induced VWF binding to immobilized A2 domain polypeptide (FIG. 14A).

The binding of ULVWF multimers to A2 domain polypeptide was examined, reasoning that ULVWF contains activated A1 domain and binds to platelet GPIbα without the need of any modulator (Arya et al., 2002). In sharp contrast with purified VWF (FIG. 14A), the ULVWF had virtually equal binding activity to immobilized A2 domain polypeptide in the presence or absence of ristocetin (FIG. 14B). These results clearly indicated that the interaction of isolated A2 domain with VWF occurs when the A1 domain is unshielded. Therefore, it was examined whether the function-blocking monoclonal antibodies against the A1 domain could inhibit ristocetin-induced VWF binding to A2 protein. The failure of the antibodies 5D2 or CR-1 to block the binding of VWF to immobilized A2 domain polypeptide, indicates that the contact site recognized by the A2 domain in the A1 domain is different than the GPIb site.

Example 9

Recombinant A2 Domain Polypeptide Blocks the Interaction of the A1 Domain with Platelet GPIBα

Figure 15:
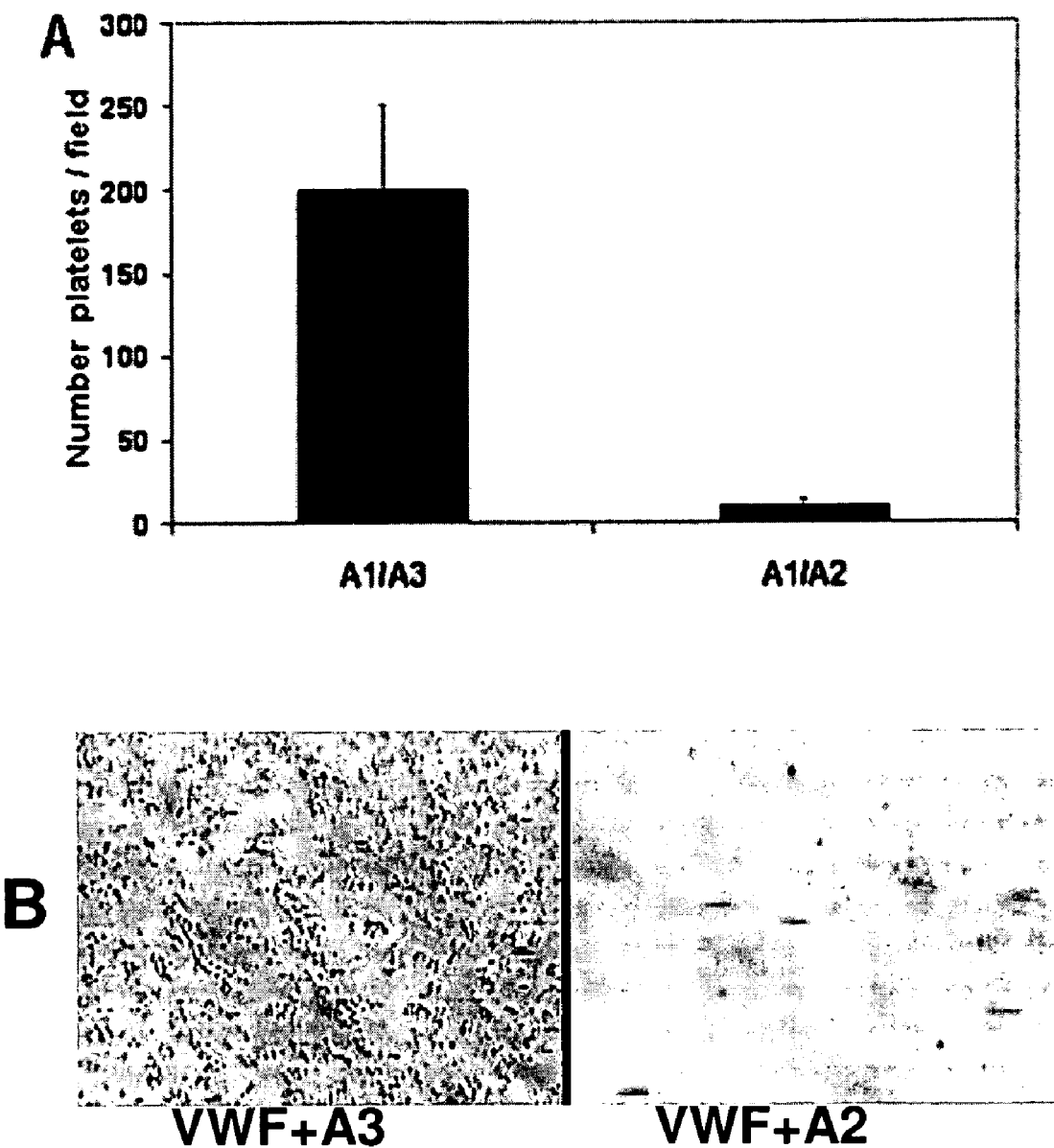
FIGS. 15A-15B show inhibition by recombinant VWF-A2 domain polypeptide of platelet adhesion to VWF-A1 polypeptide or multimeric VWF under high flow conditions.

The fact that the A1 domain polypeptide mediates flow dependent platelet adhesion by itself was exploited to examine the effect of the recombinant A2 domain polypeptide on the GPIbα binding (Cruz et al., 2005). Therefore, whole blood was perfused over a surface coated with recombinant A1 domain polypeptide pre-incubated with A2 or A3 domain polypeptide. Extensive platelet deposition was observed on surface incubated with the A3 domain, and virtually no tethering platelets on the surface incubated the A2 domain (FIG. 15A). Identical results were observed when reconstituted or plasma-free blood was used instead whole blood, demonstrating that the lack of platelet adhesion to the A1 domain is a direct consequence of the interaction with the A2 domain polypeptide. Comparable number of platelets was observed on surfaces coated with A1 domain and incubated with buffer or A3 domain polypeptide, while no platelets were detected on A3 or A2-coated plates (data not shown). The inhibitory activity of the A2 domain polypeptide was consistent with those obtained by substituting A1 domain polypeptide with multimeric VWF. Whole blood was perfused at high shear stress over a VWF-coated surface pre-incubated with A3 or A2 domain polypeptide. The adherent platelets were quantified. The platelet number on the VWF/A2 surface was approximately <5% of that on the VWF/A3 surface (FIG. 15B). These results indicate that a direct contact between the recombinant A2 domain polypeptide and the A1 domain in VWF blocks the interaction with GPIbα.

Figure 16:
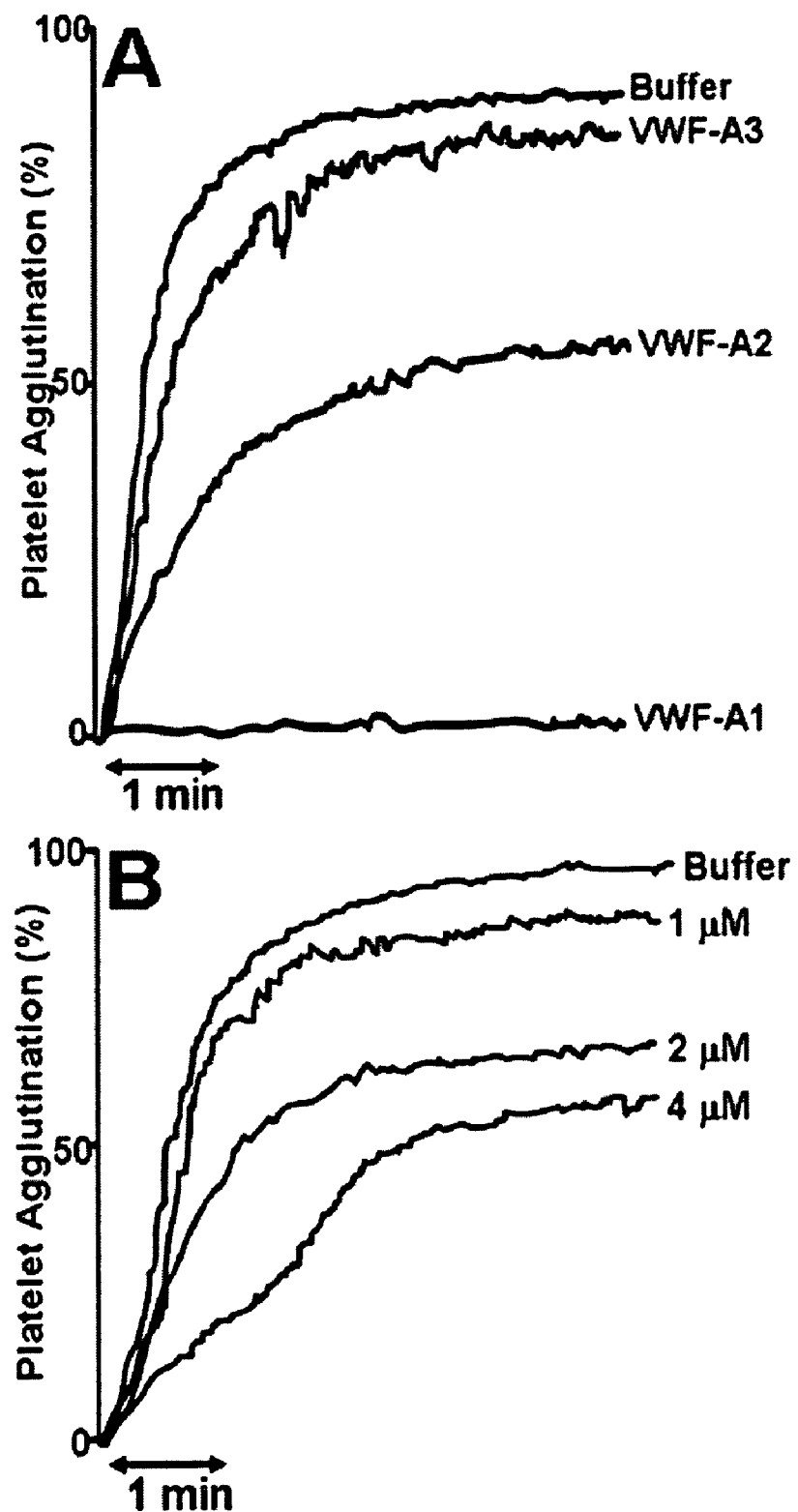
FIGS. 16A-16B demonstrate inhibition of ristocetin-induced platelet agglutination by VWF-A2 domain polypeptide.

The ability of the recombinant A2 domain polypeptide to block the binding of multimeric plasma VWF to platelet GPIbα. using ristocetin-induced platelet agglutination (RIPA) was also investigated. As previously reported, our recombinant A1 domain polypeptide completely inhibited RIPA (Cruz et al., 2000). By comparison, the inhibitory activity of the A2 domain polypeptide on RIPA was less effective than the A1 domain polypeptide but more potent than the A3 domain polypeptide (FIG. 16A). Further analyses demonstrated that the A2 domain polypeptide inhibited RIPA in a dose-dependent manner, blocking 50% of the agglutination with a concentration of 4 µM (FIG. 16B).

Significance of Certain Embodiments of the Invention

Previously, the recombinant A1 and A2 domain polypeptides that exhibit functions comparable with that of the A1 or A2 domain in multimeric VWF were characterized (Cruz et al., 2000; Cruz et al., 2003). These polypeptides have been used to examine the potential interaction between the A2 and A1 domains because several studies indirectly have implied that these two A domains may inhibit reciprocally the function of each domain (Lankhof et al., 1997; Nishio et al., 2004; De Cristofaro et al., 2006).

The capacity of A2 domain polypeptide of inhibiting the interaction between VWF and platelet GPIbα was clearly demonstrated by two approaches. First, A1 domain polypeptide or multimeric VWF-coated surface pre-incubated with the A2 polypeptide significantly reduced the number of tethering platelets under high flow conditions, and second, the soluble A2 domain also inhibited the interaction of plasma VWF with platelet GPIbα in RIPA. This study has demonstrated also that this novel inhibitory function of the A2 domain polypeptide was through a direct contact with the A1 domain. For example, (i) the A2 domain polypeptide markedly abolished the interaction of flowing platelets with the immobilized A1 domain polypeptide, (ii) the A1 domain polypeptide blocked the ristocetin-induced binding of multimeric VWF to the immobilized A2 domain polypeptide, and (iii) the specific binding activity between the A2 and A1 domain polypeptides. The putative recognition site for the A2 domain apparently is different to the GPIbα-site in A1 domain, because two function-blocking monoclonal antibodies against the A1 domain failed to inhibit the binding of VWF to A2 domain polypeptide. Possibly, the binding of the A2 domain influences the structural conformation of the A1 domain, affecting negatively the GPIbα site, in specific embodiments. On the other hand, although the antibodies against the A2 domain effectively blocked the binding of A2 domain polypeptide to immobilized VWF (FIG. 2), the ability of these antibodies to detect the A2 domain bound to the A1 domain polypeptide (FIG. 1B) indicates that the inhibition may be mainly a consequence of steric hindrance. The contact sites in each A1 and A2 domains may be determined.

The recombinant A2 domain polypeptide recognized only the active form of VWF as shown by using immobilized VWF or ristocetin-induced VWF activation (FIGS. 1A and 3A). Further evidence that the recombinant A2 domain polypeptide recognizes activated A1 domain comes from the analysis with ULVWF multimers. This is because it was previously reported that both ULVWF and the exemplary recombinant A1 domain polypeptide formed comparable high strength-bonds with GPIbα, indicating that the structural conformation of the A1 domain is similar in both situations (Arya et al., 2002). Therefore, these results indicate that the recombinant A2 domain, like the platelet GPIbα, has access to the contact site in the A1 domain after the conformational change of VWF.

Although in one embodiment there is no direct interaction between the A1 and A2 domains in the intact full length VWF, there are reports that imply a relationship between the A1 and A2 domains and their biological functions. For example, one study reported that a VWF mutant that lacked the A2 domain increased ristocetin-induced GPIb binding in comparison with wild type VWF (Lankhof et al., 1997). In addition, there are reports in which ristocetin or fluid shear stress can stimulate simultaneously the binding of A1 domain to GPIbα and the cleavage of the A2 domain by ADAMTS-13 (De Cristofaro et al., 2006; Tsai et al., 1994). This assumption may also explain the discrepancies between mutations and phenotypes observed in Type 2B von Willebrand disease (VWD; spontaneous binding to GPIbα) (Zimmerman et al., 1986; Gaucher et al., 1995; Federici et al., 1997; Ribba et al., 1997; Rendal et al., 2001), in which some mutations within the A1 domain also increased proteolysis of VWF by ADAMTS-13. Therefore, one can suggest that these naturally occurring mutations, the binding of VWF to collagen, or high fluid shear stress disrupts the potential A1-A2 interaction, relieving the inhibition for the binding to GPbα.

Finally, the A2 domain polypeptide blocked 50% RIPA with a concentration of 4 µM that is approximately 150 times the concentration of multimeric VWF (based on MW of 250 kDa) in our PRP suspension. In contrast, the A2 polypeptide bound to immobilized VWF with an apparent KD ~200 nM, while it had a significantly higher binding affinity for the immobilized A1 domain (apparent KD ~50 nM). It is most likely that the A1 domain adopts a different structural conformation in the three different conditions. For example, one marked difference is that the A1 domain is glycosylated in full length VWF, and we and others have reported that glycosylation in the A1 domain influences the biological function of the domain (Cruz et al., 1993; Esch et al., 2005). In addition, it is possible that the modulator ristocetin interferes with the interaction of the A2 protein and VWF because ristocetin binds to an amino acid sequence located between the A1 and A2 domain (Dong et al., 2001).

Therefore, recombinant polypeptides have been used to analyze the relationship between the A1 and A2 domains of VWF. The results have demonstrated that a recombinant VWF-A2 domain polypeptide binds directly to the active form of its homologous A1 domain, and that this interaction effectively blocks the binding of platelet GPIbα to VWF under flow conditions. These results indicate that a direct contact between the A1 and A2 domains in VWF inhibits the GPIbα binding. In addition, these results indicate that the A2 domain polypeptide or a fragment of it has the potential to be used as an anti-thrombotic agent that blocks specifically the interaction between the activated form of VWF and platelet GPIb.

Example 10

Exemplary Materials and Methods for Examples 7-9

Monoclonal antibodies and Recombinant proteins—Monoclonal antibodies CR1 and 5D2 (De Luca et al., 2000) against the VWF-A1 domain were obtained. Monoclonal antibody VP-1 against VWF-A2 domain was obtained. Monoclonal anti-human VWF-A2 domain antibody (Anti-A2) was purchased from R&D System, Inc. (Minneapolis, Minn.). The antibody 12F1 against the α2-I domain of the integrin α2β1 was used as a negative control. Recombinant VWF-A1 (amino acids Q1238-P1471), VWF-A2 (amino acids G1481-R1668) and VWF-A3 (amino acids S1671-G1874) domain polypeptides were expressed in E. coli as a fusion protein containing the His tag in the N terminus and purified as previously described (Cruz et al., 2000; Cruz et al., 2003; Bienkowska et al., 1997). An exemplary mRNA coding region of VWF-A2 domain is listed in SEQ ID NO: 31. The purity of the recombinant proteins was verified by SDS-gel electrophoresis. Multimeric VWF was purified from plasma or cryoprecipitate as was previously described (Cruz et al., 2000; Cruz et al., 1993). Multimers enriched in ultra-large (UL) VWF forms were obtained from the supernatant of histamine-stimulated human umbilical vein endothelial cells as we previously described (Arya et al., 2002).

Platelet Agglutination Assay—As we previously described (Cruz et al., 2000), ristocetin-induced platelet agglutination (RIPA) was carried out in siliconized glass cuvettes at 37° C. with constant stirring at 1,200 rpm in a four channel aggregometer (Bio/Data Corp. Horsham, Pa.). Suspensions of platelet-rich plasma (PRP) containing different concentrations of each VWF-A1, A2 or A3 domain polypeptide were prepared. After 2 min incubation at 37° C., agglutination was initiated by the addition of ristocetin (Sigma, St. Louis, Mo.) to a final concentration of 1 mg/ml.

Binding assays—The VWF-A2 protein was diluted to 5 µg/ml with 65 mM sodium phosphate buffer, pH 6.5 (PB), and added into microtiter wells (75 µl/well) and incubated for 1 h at 37° C. The wells were washed three times with phosphate buffered saline, pH 7.4 (PBS) and blocked with 3% (w/v) bovine serum albumin (BSA) in 25 mM Tris-HCl, 150 mM NaCl, pH 7.4 (TBS) containing 0.05% (v/v) Tween-20 (TBS-T) for 1 h at 37° C. A solution of VWF (5 µg/ml) or ULVWF (0.5 µg/ml) mixed with ristocetin (0.5 mg/ml) or TBS was added and incubated for 1 h at 37° C. To test the ability of A1 domain polypeptide or monoclonal antibodies against A1 domain in blocking the interaction between the VWF and insoluble A2 polypeptide either A1 polypeptide (2 µM), CR-1, or 5D2 (10 µg/ml) was added to the mixture of VWF and ristocetin or TBS. Wells were washed with TBS-T and anti-VWF-horseradish peroxidase conjugate (1:500, DAKO, Carpinteria, Calif.) was added and incubated for 45 min at 37° C. After washed three times with TBS-T, the substrate o-phenylenediamine (OPD from Sigma) was added. After 10-15 min of substrate conversion, reactions were stopped with 0.025 ml of 2N H2SO4, and the plates were read at 490 nm.

To test the binding of A2 or A1 polypeptide to immobilized VWF, the wells were coated with 75 µl of purified plasma VWF (1 or 5 µg/ml) diluted in PB and incubated for 1 hr at 37° C. The wells were washed three times with PBS and blocked with 3% (w/v) BSA in TBS-T for 1 h at 37° C. Increasing concentrations of recombinant A2 or A1 polypeptide were added to the wells and incubated for 1 h at 37° C. Additionally, to test the ability of monoclonal antibodies against human VWF-A2 domain, A2 polypeptide (300 nM) was mixed with Anti-A2 or VP-1 antibody (10 µg/ml) and incubated at room temperature for 10 minutes prior the incubation in the wells for 1 h at 37° C. After washing three times with TBS-T, a peroxidase-conjugated monoclonal anti-histag antibody (Sigma) was added (1:10,000) and incubated for 45 min at 37° C. The wells were again washed and the substrate OPD was added. After 15-25 min of substrate conversion, reactions were stopped with 0.025 ml of 2 N $H_2SO_4$, and the plates were read at 490 nm. Net specific binding was determined by subtracting OD values from wells coated only with BSA from the total binding values.

Analyses of the binding of A2 polypeptide to immobilized A1 domain polypeptide or vice versa were performed by diluting A2 or A1 polypeptide to 5 µg/ml in PB and incubated for 1 h at 37° C. After washing twice with PBS to remove unadsorbed protein, wells were blocked by the addition of 3% (w/v) BSA in TBS-T for 1 h at 37° C. Increasing concentrations of the analyte were added to the wells and incubated for 1 h at 37° C. After washing three times with TBS-T, the bound A2 or A1 polypeptide was detected with monoclonal Anti-A2 antibody (1 µg/ml) or monoclonal antibody CR-1 (1 µg/ml), respectively. After incubation of 1 h at 37° C., the wells were again washed and a peroxidase-conjugated goat anti-mouse IgG antibody (1:3000) was added and incubated for 45 min at 37° C. Measurements were performed as described above and net specific binding was determined by subtracting OD values from wells coated only with BSA from the total binding values obtained as described above.

Preparation of proteins coated coverslips—The coverslips were prepared as we previously described (Cruz et al., 2000; Cruz et al., 2005). Individual A1, A2, or A3 domain polypeptide was diluted to 4 µM in TBS, pH 7.4, and the purified plasma VWF was diluted to 50 µg/ml in TBS and added to coverslips and incubated for 60 min at 37° C. Then, either A2 or A3 domain polypeptide (4 µM) was added to the A1- or VWF-coated coverslips and incubated for 45 min at 37° C. and then used immediately in blood perfusion studies as described below.

Preparation of Plasma-Free Blood—Approval was Obtained from the Baylor College of Medicine institutional review board for these studies. Informed consent was provided according to the Declaration of Helsinki. For experiments using plasma-free blood, the blood was prepared as recently described elsewhere (Morales et al., 2006).

Flow Assays—The flow assays were performed as we previously described (Cruz et al., 2005). A syringe pump (Harvard Apparatus Inc., Holliston, Mass.) was used to aspirate whole blood through the flow chamber. Flow rate of 0.6 ml/min produced a wall shear rate of 1500 $s^{-1}$. Whole blood was perfused for 2 min followed by TBS. Tethered platelets were observed with phase contrast objectives and recorded by videomicroscopy. The number of platelets tethered to the surface was determined by overlaying a 15 square grid on 8 frames and counting and averaging the number of platelets in 6 randomly selected squares. For some assays (plates containing A1/A2, A2 or A3 polypeptide), the whole frame was counted. Some experiments were performed in duplicate or triplicate using different blood donors.

Protein Quantitation-Protein concentration was determined by the BCA method (Pierce). Coomassie Blue staining of SDS-PAGE gel was used to assess the purity of the VWF-A domain proteins.

Example 11

A2 Domain Blocking of A1 Domain and Platelet GPIbα

Figure 18:
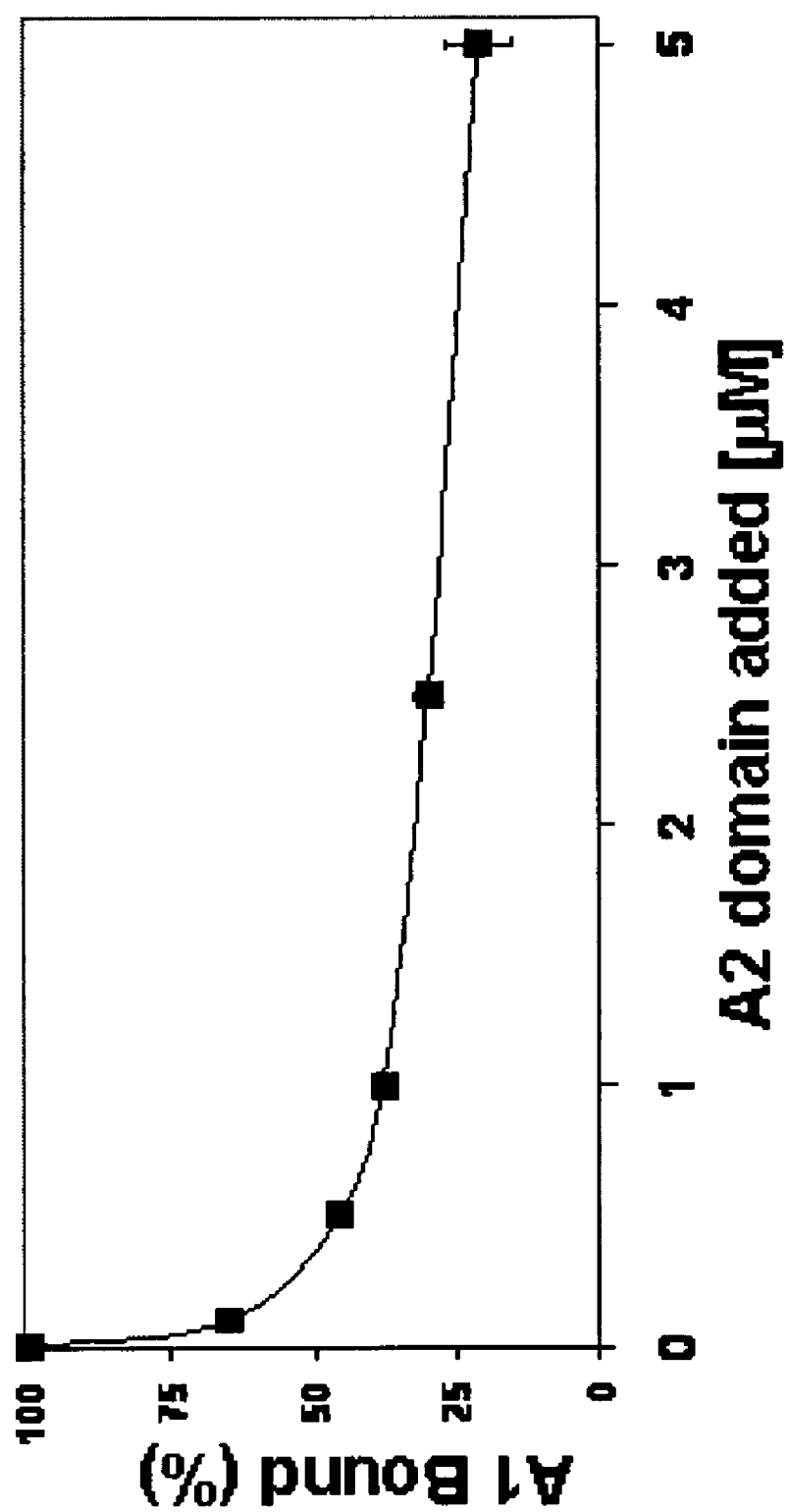
FIG. 18 demonstrates inhibition of recombinant A1 domain binding to platelet GPIbα by the A2 domain polypeptide. The binding of the A1 domain (0.25 µM) to immobilized fixed platelets was measured in the presence of purified A2 domain protein at the indicated concentrations or the same volume of TBS in the control mixture. 100% is defined as the fraction of added A1 domain polypeptide bound with no A2 domain. Each point represents mean±S.D. of two independent sets of triplicate determinations.

The capacity of the A2 domain in blocking the interaction between the A1 domain and platelet GPIbα under static conditions was assessed. The inhibition of the binding of the A1 domain to immobilized fixed platelets by the A2 domain is shown in FIG. 18. The $IC_{50}$ for the A2 domain protein was 0.30 μM. This assay also demonstrates that both the A1 and A2 domain polypeptides are capable of interacting with each other in solution.

Example 12

Effect of the A2 Domain on the GPIbα-Binding Activity of the Adjacent A1 Domain The A1A2 segment of human VWF was designed to evaluate the influence of the A2 domain on the GPIbα-binding activity of the adjacent A1 domain. The His-tag in the A1A2 protein allows the isolation of the protein using nickel column chromatography followed by a heparin column, which suggests that the adjacent A2 domain does not impair the heparin binding site in the A1 domain. The calculated molecular mass for the sequence between Q1238 and R1668 is 48,245 Da. The 12 additional amino acids from the vector sequence add another 1,613 Da, bringing the total estimated molecular mass to 49,858 Da. This is in agreement with the estimated molecular mass of the purified material of 55,000 Da (FIG. 19A, inset) as assessed by SDS-PAGE. The recombinant A1A2 protein was monomeric when analyzed by SDS-PAGE under nonreducing conditions, excluding the possibility of disulfide-mediated oligomerization or aggregation. As previously reported for the recombinant A1 domain protein, a slight differential in migration for the A1A2 protein under reduced and non-reduced conditions provided evidence for the formation of a disulfide bond between C1272 and C1458 (Cruz et al., 1993). In addition, we tested the structural integrity of the A1A2 protein with monoclonal antibodies using capture ELISA. Both VP-1 and Anti-A2 antibodies against the human VWF-A2 domain bound normally to the A1A2 protein (78% and 90%, respectively, of binding to single A2 domain polypeptide) indicating that the A2 domain in the A1A2 protein is correctly folded and that the adjacent A1 domain does not affect a critical structural feature of the bound epitope. However, both CR-1 and 6G1 antibodies against human VWF-A1 domain bound to the A1A2 protein between 35% and 45% of binding to single A1 domain polypeptide.

Figure 19:
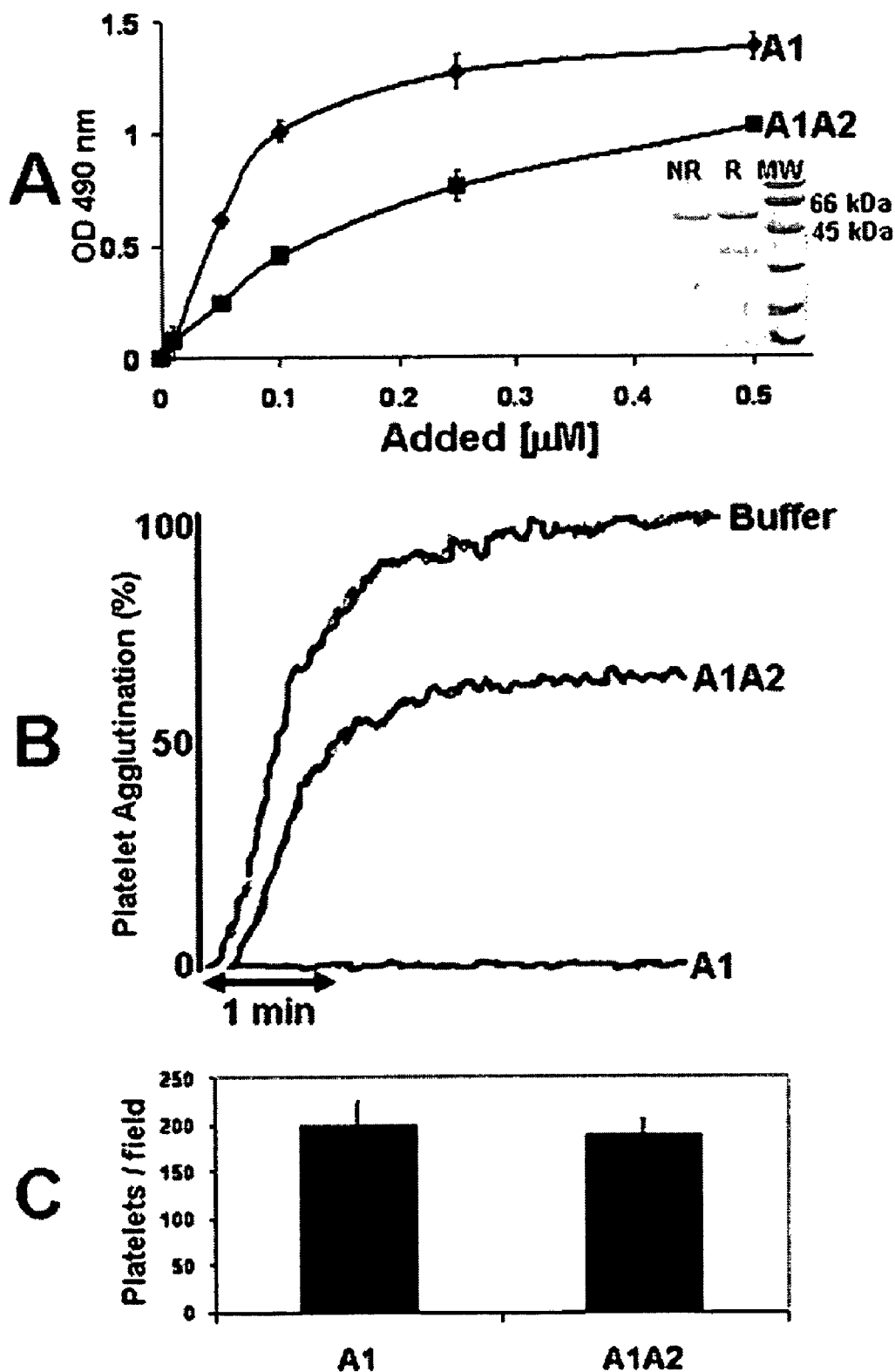
FIGS. 19A-19C show the effect of the A2 domain on the binding to GPIbα of the adjacent A1 domain.

The purified A1A2 protein was then tested for its ability to bind platelet GPIbα. FIG. 19A shows the specific binding of the A1A2 protein to immobilized fixed platelets. It bound in a concentration-dependent and saturable manner with a half-maximal binding occurring at approximately ~130 nM. In contrast, the A1 domain polypeptide had a greater binding activity with a half-maximal binding occurring at ~40 nM. The ability of the recombinant A1A2 protein to block the binding of multimeric plasma VWF to platelet GPIbα using ristocetin-induced platelet agglutination (RIPA) was also tested. As previously reported, the recombinant A1 domain polypeptide completely inhibited RIPA at a concentration of 2 μM (Cruz et al., 2000). By comparison, the inhibitory activity of the A1A2 protein on RIPA was less effective than the A1 domain polypeptide (FIG. 19B). Lastly, an equivalent numbers of tethering platelets were observed between surfaces coated with A1 or A1A2 protein under flow conditions (FIG. 19C).

Example 13

Exemplary Peptide and Effects on SIPA, RIPA, and Platelet Adhesion to Immobilized Collagen Under High Flow Conditions The A1 domain of von Willebrand factor (VWF) is flanked by the A2 domain at the C-terminus. In specific embodiments of the invention, the A2 domain is involved in regulating the A1-GPIb binding. The present inventors has investigated the effect of the A2 domain on the binding activity of the A1 domain using recombinant A domain polypeptides, multimeric VWF, monoclonal antibodies and synthetic peptides.

The A2 domain bound to the A1 domain polypeptide and full length VWF with a half-maximal binding observed at 60 and 160 nM, respectively. This interaction was inhibited by antibodies against either the A2 domain or the A1 domain and by the purified A1 domain itself. The A2 domain blocked GPIb-mediated platelet adhesion under high flow conditions by recognizing the GPIb-binding conformation in the A1 domain because it only interacted with immobilized VWF or VWF activated by the modulator ristocetin. In contrast to plasma VWF, the ultra-large (UL)VWF multimers and a recombinant VWF-A1A2A3 polypeptide containing a gain-of-function mutation (R1308L) of Type 2B von Willebrand disease (VWD) bound to the A2 domain without the need of ristocetin. An exemplary peptide that is 10 residues long (B9), derived from the A2 domain, is identified that effectively inhibited ristocetin-induced platelet agglutination, shear-induced platelet aggregation and platelet adhesion to collagen under flow conditions. It also blocked the adhesion of flowing platelets to newly released ULVWF from endothelial cells. Thus, the A2 domain polypeptide specifically binds to the active conformation of VWF. The purified A2 domain or a small fragment of it blocks the interaction with platelet GPIb under high flow conditions.

Therefore, after analysis of over 40 synthetic peptides comprising the A2 domain sequence of VWF (length of 10 amino acids each with an overlap of six residues), the inventor has identified one that efficiently inhibits both RIPA (ristocetin-induced platelet agglutination) and platelet adhesion to collagen under high flow conditions. The former is incubating the peptide (50 μg/ml) with platelet rich plasma (PRP) for 2 minutes prior to the addition of the modulator ristocetin, while the latter is by incubating the peptide in whole blood for 1 minute prior to perfusing it over the collagen surface. It blocked RIPA by 100% and at 75 μg/ml it blocked 100% of platelet adhesion. These assays have been performed using two different preparations of the peptides and the results have been reproducible. The peptide (B9) interacts with the A1 domain of VWF.

Figure 20:
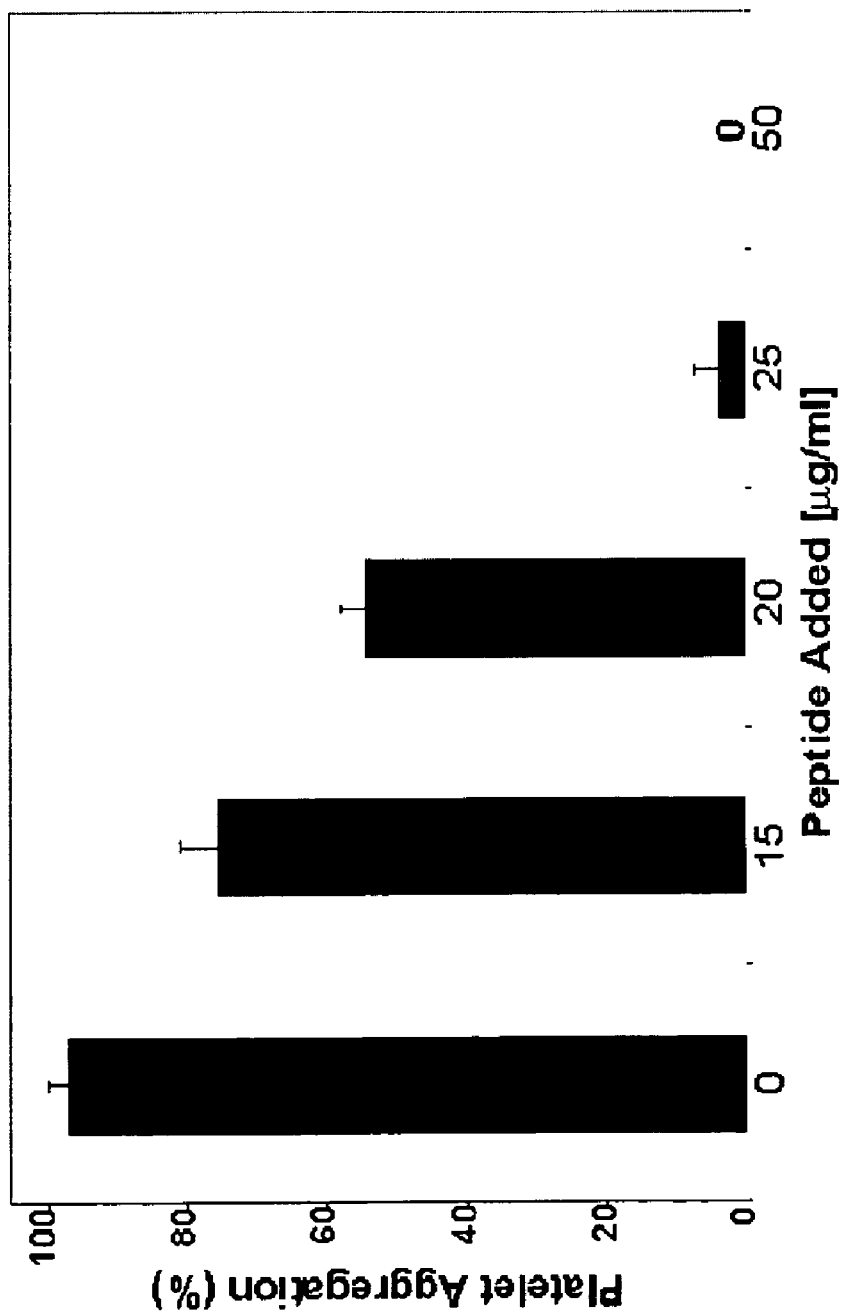
FIG. 20 shows shear-induced platelet aggregation (SIPA) at 10,000$^{-s}$ for 60 seconds with an exemplary peptide.

FIG. 20 shows effect of B9 peptide on shear-induced platelet aggregation. Shear-induced aggregation in platelet-rich plasma was measured in the absence (buffer) or after pre-incubating the sample with B9 (at concentrations as indicated) for 2 minutes at ambient temperature before the application at 120 dynes/cm$^2$ of shear stress in a cone-and-plate viscometer. Results are the means of 4 experiments performed using different donors.

Figure 21:
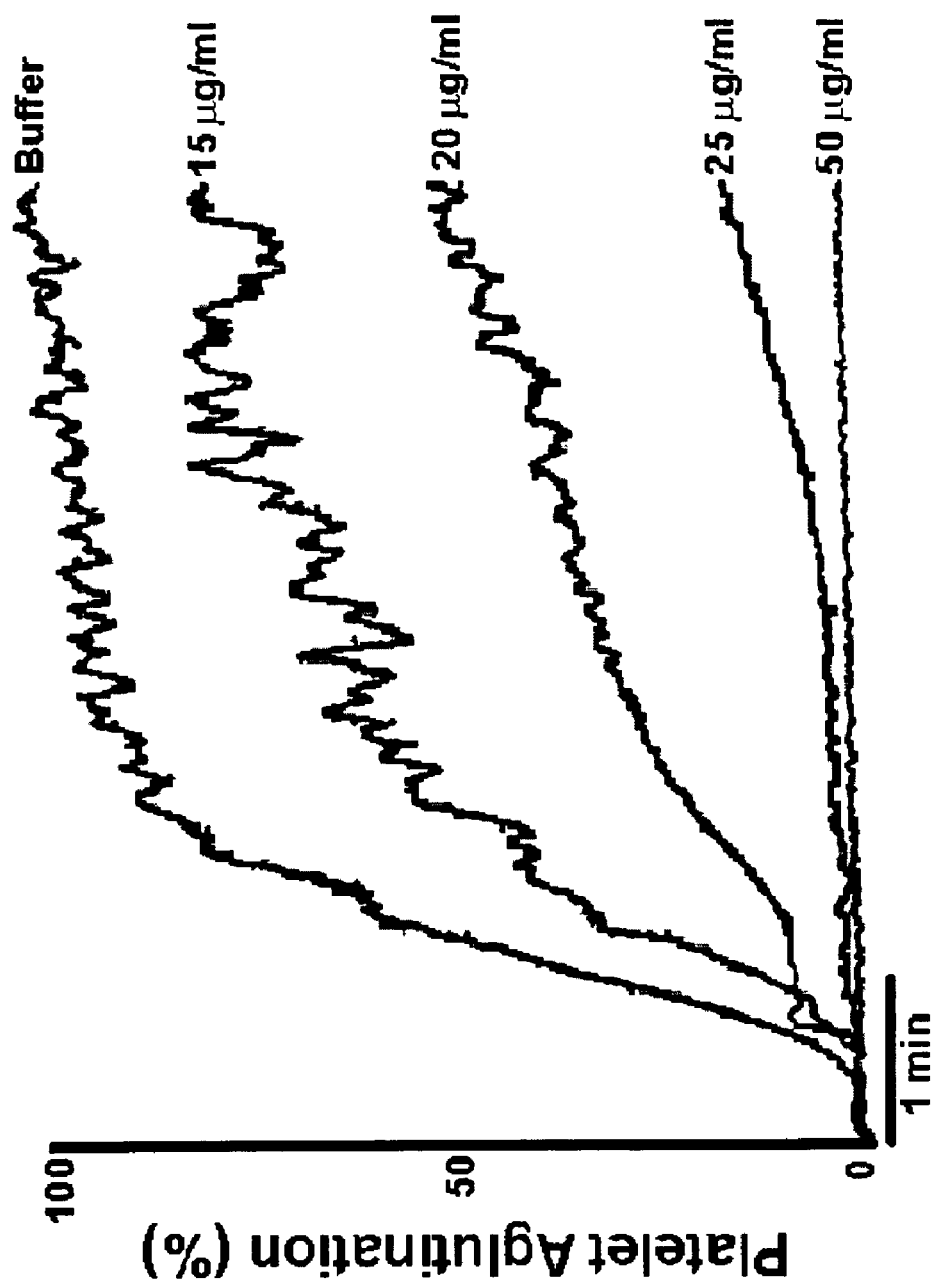
FIG. 21 shows the effect of an exemplary peptide on ristocetin-induced platelet agglutination (RIPA).

FIG. 21 shows inhibition of platelet agglutination by the exemplary B9 peptide. Increasing concentrations of the B9 peptide were incubated with diluted PRP (1:2) for 2 min at 37° C. in an aggregometer cuvette. Agglutination was initiated by the addition of 1.0 mg/ml risrocetin. The figure is epresentative of six determinations.

Figure 22:
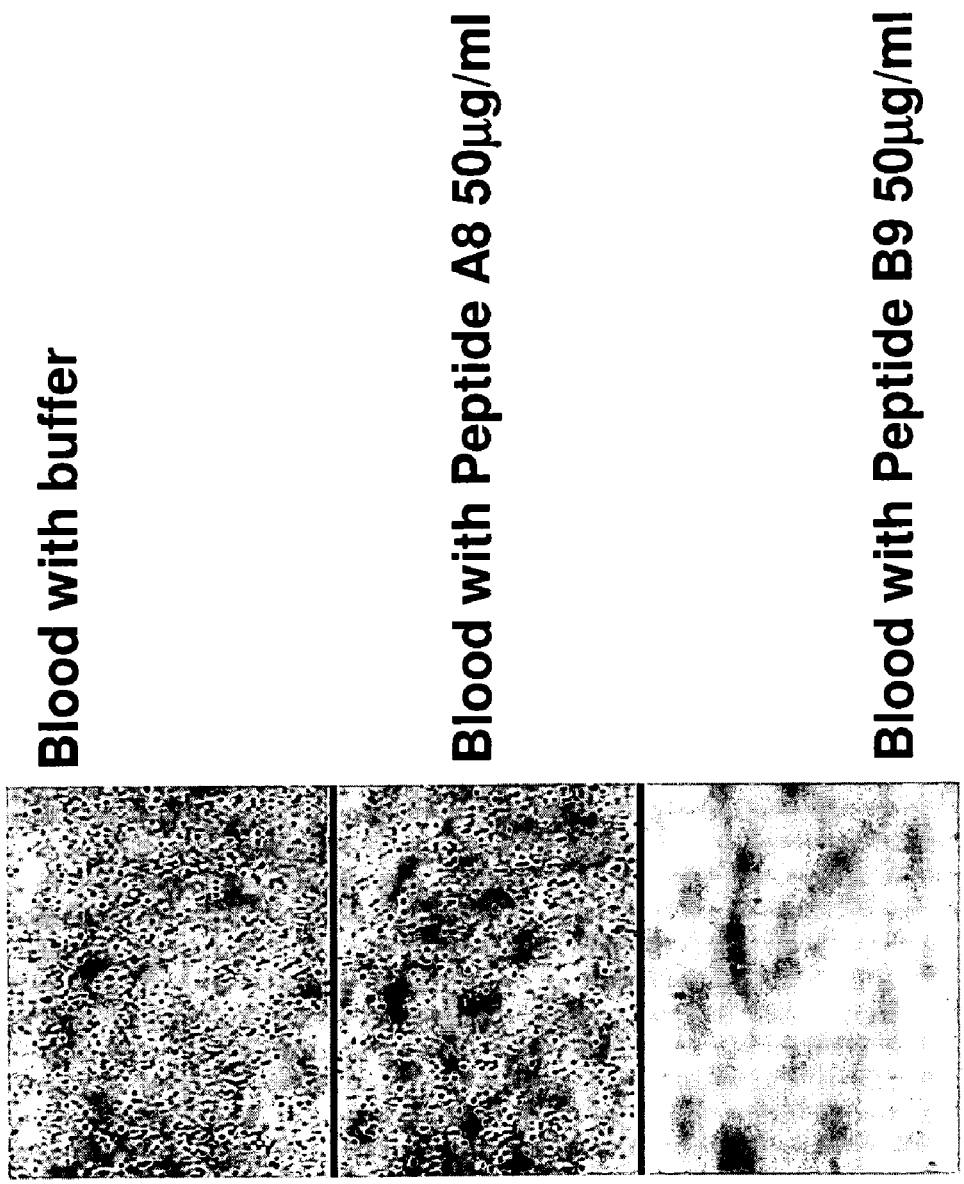
FIG. 22 demonstrates platelet adhesion to immobilized collagen under high flow conditions (½) with an exemplary peptide.

FIG. 22 demonstrates interaction of flowing platelets with a collagen surface. Whole blood was pre-incubated with either buffer, peptide A8 (IGEADFNRSK; SEQ ID NO:29) or B9 for 2 minutes prior to be perfused at a shear rate of 1,500 s$^{-1}$ over collagen. The photomicrographs depict the platelets tethered to the surface after 2 min of perfusion and represent three separate experiments with blood from different donors.

In addition, FIG. 23A shows that RIPA was inhibited by the N-terminal fragment polypeptide of A2 (SEQ ID NO:2). FIG. 23B demonstrates interaction of flowing platelets with a collagen surface. Blood was pre-incubated with either buffer or SEQ ID NO:2 for 2 minutes prior to being perfused at a shear rate of 1,500 s$^{-1}$ over collagen. The photomicrographs depict the platelets tethered to the surface after 2 minutes of perfusion. FIG. 23B shows that SEQ ID NO:2 reduced both platelet adhesion to collagen and the formation of microaggregates (right panel) as compared with blood incubated with buffer only in the left panel. The results obtained in both RIPA and flow assays with SEQ ID NO:2 suggest the location for the contact region of the A1 domain on A2.

Figure 24:
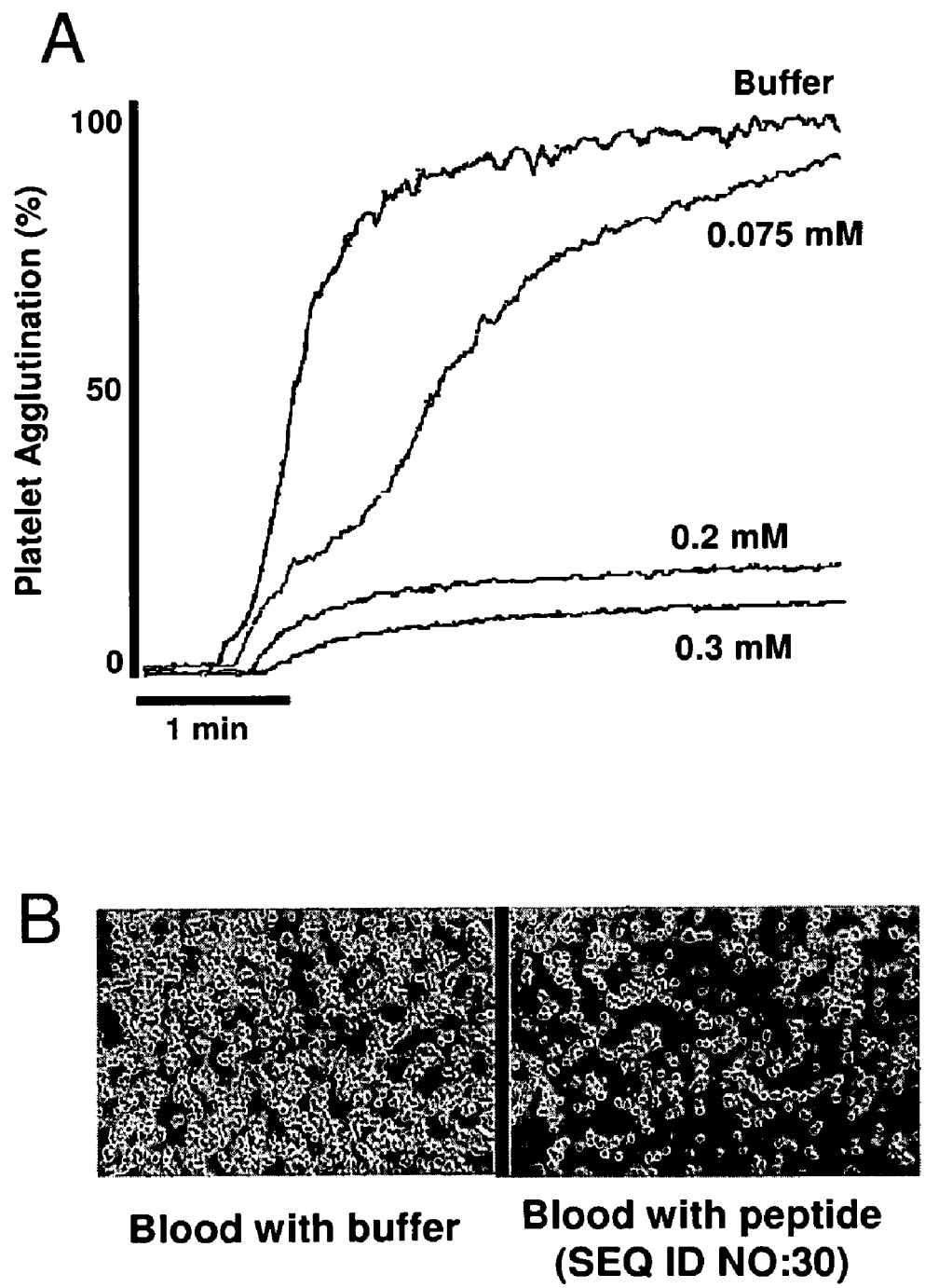
FIGS. 24A-24B show the effect of exemplary peptide of SEQ ID NO:30 on thrombosis.

Based on the sequence of SEQ ID NO:2, 24 peptides were synthesized, each with 10 amino acid length and with 5 residues overlapping. These peptides were tested for their effect on RIPA. The 4 peptides that encompass the amino acid sequence M1521-M1545 inhibitory activity on RIPA. In addition, the peptide 1536HVTVLQYSYM1545 (SEQ ID NO:30) had a strong inhibitory effect. FIG. 24A shows that this peptide inhibited RIPA in a dose dependent manner. This peptide was also tested for its effect on platelet adhesion to collagen under high flow conditions (FIG. 24B). As described above, whole blood incubated with this peptide (0.3 mM) was perfused over the collagen surface as shown in the right panel of FIG. 24B, the number of platelets which adhered to the collagen was significantly diminished in comparison with blood containing only buffer (left panel).

Exemplary peptides of the invention include SEQ ID NO:26 (B8) (SKGDILQRVR), SEQ ID NO:27 (ILQRVREIRY) (B9), SEQ ID NO:28 (VREIRYQGGN) (B10), and SEQ ID NO:30 (HVTVLQYSYM). In specific embodiments, SEQ ID:30>SEQ ID:27>SEQ ID:28>SEQ ID:26 in potency.

Example 14

Further Identification of A2-Derived Peptides Capable of Blocking the Interaction Between VWF and Platelet GPIBα

The inventor has previously determined the existence of peptides from the A2 domain sequence that inhibit RIPA and platelet adhesion to collagen under flow conditions. This study is to further test the potency of A2 domain antithrombotic agents that target the A1 domain in VWF and to test them in animal models.

Peptides are constructed that are 9 residues long and overlapping 7 residues from SEQ ID NO:2 to examine their ability to block RIPA and platelet adhesion to collagen under flow conditions, These peptides are tested over a range of concentrations between 0.01 mM and 0.5 mM, as was previously shown. The peptides with the highest potency (>50% inhibition) in blocking the VWF-GPIbα interaction are aligned based on the overlapping sequence to delineate the minimum sequence of amino acid residues required to achieve the most effective inhibition. For example, if three successive peptides demonstrate the strongest inhibitory effect, it will indicate that a peptide of at least 13 amino acid residues long is the most promising antithrombotic agent. Then, the resultant peptide is synthesized and is tested again using the same procedures as for the smaller peptides. Alternatively, if the inhibitory potency of a nine residue peptide is significantly higher than its two flanking peptides (requires <50% of the concentration of other two peptides to achieve same inhibition), it is then tested in a mouse model as described in Example 15.

Methods—The peptides that show the greatest capacity to inhibit the VWF-GPIbα interaction are tested for their binding activity to the A1 domain. It has been demonstrated that SPR can be used to study the direct binding of small molecules to larger targets (Nguyen et al., 2007). Therefore, as previously described (Cruz et al., 2005; Morales et al., 2006), SPR is used to determine the binding kinetics of different peptides to the immobilized recombinant A1A2A3 polypeptide or full length VWF. Alternatively, biotin-labeled peptides are synthesized to analyze their binding to immobilized A1A2A3 or multimeric VWF using ELISA, in which the bound biotin-conjugated peptides are detected using horseradish peroxidase-conjugated streptavidin. In addition, the $K_D$ is evaluated from the ELISA using the KaleidaGraph software as recently described (Martin et al., 2007)

Example 15

Examine the Antithrombotic Effect of A2-Derived Peptides in Animal Models

Animal models are used to determine the effect of the peptide in conditions associated with VWF-induced thrombosis. ADAMTS-13$^{-/-}$ (knock out) mouse intercrossed into CASA/Rk is used. This animal model is available and is an excellent model to study thrombotic conditions where VWF plays a pathogenic role (Motto et al., 2005). These animals develop spontaneous thrombotic thrombocytopenic purpura (TTP) and die in about 10 days if treated with Shiga toxin 2 (STX-2). One group of animals are treated with both STX-2 and peptide and the progression of thrombotic microangiopathy is compared with a group treated with STX-2 only. The study uses the A2 peptides from Example 14 with the strongest inhibitory activity as determined by in vitro experiments delineated previously. The peptide dosage used in vivo will take into consideration the concentration required to inhibit thrombus formation in the in vitro studies, the concentration of VWF in plasma, and the blood volume and weight of the animals. Assuming 0.15 mM of peptide is required to inhibit thrombus formation in 2 ml of blood, then if the concentration of plasma VWF is 10 µg/ml or 40 nM and a 20 gm mouse has 3.5 ml of blood, the dose is 15 mg/kg (peptide/mouse weight) (Harkness and Wagner, 1989). Because the half-life of plasma VWF in mice is about 2.8 hours (Lenting et al., 2004), the peptide is administered every 3 hours. The survival rates are measured and clinical and laboratory parameters related to the development of thrombotic microangiopathy such as platelet count, hemoglobin, blood urea nitrogen (BUN) levels, the presence of schistocytes on peripheral smear, and the formation of VWF-rich micro-thrombi in targeted organs, are monitored. The following lab exemplary equipment is used to facilitate these studies; a SCIL Vet abc, hematology analyzer, and a SCIL Reflovet® Plus veterinary chemistry analyzer. Improvements in survival and a milder clinical course in the group of animals treated with the A2-derived peptide is anticipated.

The study also evaluates the role of the peptide in the formation of microthrombi using intravital microscopy. This procedure determines the rate of thrombus formation in thrombosis-prone mutant animals that are pre-treated with peptide.

The effect of the peptide on circulating VWF is evaluated by VWF-collagen binding activity (Morales et al., 2006; Estavillo et al., 1999) using plasma VWF obtained from mice treated with either peptide or saline. The effect of the peptide on platelet function is tested by comparing bleeding time between the peptide-treated mice vs. non-treated controls. A longer bleeding time in the peptide-treated group would correlate with the decreased collagen binding activity of plasma VWF shown in preliminary data.

Methods—The study determines the in vivo effect of the peptide under conditions associated with abnormally high levels of ultra large forms of VWF multimers. Research will evaluate the effect of A2-derived peptide in the development of thrombosis using an ADAMTS-13$^{-/-}$ mouse that is in a CASA/Rk background because it is a well-recognized animal model for the studies of thrombotic microangiopathies where VWF is involved (Motto et al, 2005). Microangiopathy is induced by systemic injection of Shiga toxin-2 (STX-2). One group will be treated with both STX-2 (intraperitoneal, IP) and A2-derived peptide (intravenous, IV) and another with STX-2 alone (IP). Using an initial dose of 15 mg/kg (peptide/mouse weight), the frequency of peptide treatment is every 3 hours. Control animals receive buffer to account for the volume and stress of injection. The starting dose is 5 mg/kg/day and is adjusted according to study findings.

Study 1: Survival

| Experimental groups | STX-2 (IP) | Peptide (IV) | (10 animals/group) |
|---|---|---|---|
| 1) ADAMTS-13 −/− CASA/Rk | (125 ng/Kg) | vehicle | (Experimental control) |
| 2) ADAMTS-13 −/− CASA/Rk | (125 ng/Kg) | 5 mg/kg/day | (Experimental test) |
| 3) ADAMTS-13 −/− CASA/Rk | | 5 mg/kg/day | (Experimental control) |
| 4) ADAMTS-13 −/− CASA/Rk | | vehicle | (Experimental control) |

ADAMTS-13 −/− CASA/Rk dies in ~10 days when treated with STX-2 (Motto et al., 2005). In certain aspects, animals treated with peptide survive longer because the peptide inhibits the formation of thrombotic microangiopathy, which causes organ death.

Study 2: Evaluation of the Thrombotic Phenotype in Response to A2-Derived Peptide Treatment.

Another set of animals are treated with the same dose of peptide set by study 1 and are evaluated for the thrombotic phenotype that is associated with VWF. Thrombotic microangiopathy is induced with STX-2. Two animals from each group are sacrificed every 24 hours over a period of 10 days.

| Experimental groups | STX-2 (IP) | Peptide (IV) | (25 animals/group) |
|---|---|---|---|
| 1) ADAMTS-13 −/− CASA/Rk | (125 ng/Kg) | | (Experimental control) |
| 2) ADAMTS-13 −/− CASA/Rk | (125 ng/Kg) | X mg/kg/day | (Experimental test) |
| 3) ADAMTS-13 −/− CASA/Rk | | X mg/kg/day | (Experimental control) |
| 4) ADAMTS-13 −/− CASA/Rk | | vehicle | (Experimental control) |

The study measures the following: platelet count, hemoglobin, blood urea nitrogen (BUN), and the presence of schistocytes on peripheral smear. For the blood smear, 3 µl of sample/slide is used. Slides are air dried, dipped into CAMCO quick stain for 5-10 min, rinsed with deionized water for 15-20 min, and finally air dried and mounted with Cytoseal™ XYL. The study also looks for the formation of VWF-rich microthrombi in different organs (kidney, brain, intestine, peritoneum, liver, spleen, adrenal and heart). Dissected organs are stored in the solution Z-fix (Anatech Ltd., MI) containing formaldehyde. Samples are embedded in paraffin using the automated system Vibratome TPC (Vibratome, MO). The paraffin blocks are sliced with microtome to produce 4 micron thick samples, baked and stained. A less aggressive phenotype in the group of animals treated with the A2-derived peptide is anticipated.

Study 3: Evaluation of the Effect of the A2-Derived Peptide on VWF and Platelets.

The effect of the A2-derived peptide on VWF is determined by VWF-collagen binding activity as described elsewhere (Morales et al., 2006; Estavillo 1999). Wild type C57BL/6 mice are divided into 3 groups (named 1 hr, 3 hrs and 6 hrs) and treated with peptide. Each group is then sacrificed at corresponding time points. Plasma VWF is obtained from mice treated with either peptide or vehicle.

| Experimental groups | Peptide (IV) | (6 animals/group) |
|---|---|---|
| 1) C57BL/6 WT | X mg/kg | (Experimental test) |
| 2) C57BL/6 WT | none | (Experimental control) |
| 3) C57BL/6 WT | vehicle | (Experimental control) |

Study 4: The effect of treatment of the A2-derived peptide on platelet function is evaluated by tail-bleeding time. Mice are anesthetized with combo rodent III, 3 mm of the tail tip is then be cut off and immediately placed in 1 ml of PBS that has been pre-warmed to 37° C. and contained in a 1.5 ml tube. The tail is transferred to a new tube every 30 min and the time it takes for bleeding to stop is recorded. No animal is allowed to bleed for more than 10 min. Wild type C57BL/6 mice are divided into 3 groups (named 1 hr, 3 hrs and 6 hrs), treated with peptide, and then measured for bleeding time at the pre-assigned time point.

| Experimental groups | Peptide (IV) | (6 animals/group) |
|---|---|---|
| 1) C57BL/6 WT | X mg/kg | (Experimental test) |
| 2) C57BL/6 WT | none | (Experimental control) |
| 3) C57BL/6 WT | vehicle | (Experimental control) |

If the peptide causes prolonged bleeding time, it is expected that it will correlate with a decreased collagen binding activity of plasma VWF from mice treated with peptide.

Study 5: Evaluation of the role of the peptide in the formation of microthrombi. This is assessed by intravital microscopy. The study uses ADAMTS-13$^{-/-}$ mice in CASA/Rk background which is a well-known animal model for the studies of thrombotic microangiopathies where VWF is strongly involved. Intravital microscopy is designed to observe the rate of thrombus formation in the microvasculature in a living animal. The time that it takes from the initiation of the injury until the cessation of blood flow is recorded.

| Experimental groups | Peptide | (5 animals/group) |
|---|---|---|
| 1)ADAMTS-13 −/− CASA/Rk | X mg/kg | (Experimental test) |
| 2)ADAMTS-13 −/− CASA/Rk | none | (Experimental control) |
| 3)ADAMTS-13 −/− CASA/Rk | vehicle | (Experimental control) |

A delay is expected in the formation of thrombi and vessel occlusion in the animals treated with the A2 peptides compared to the ones treated with buffer only.

Example 16

A2 Domain Binds to VIMENTIN

Figure 25:
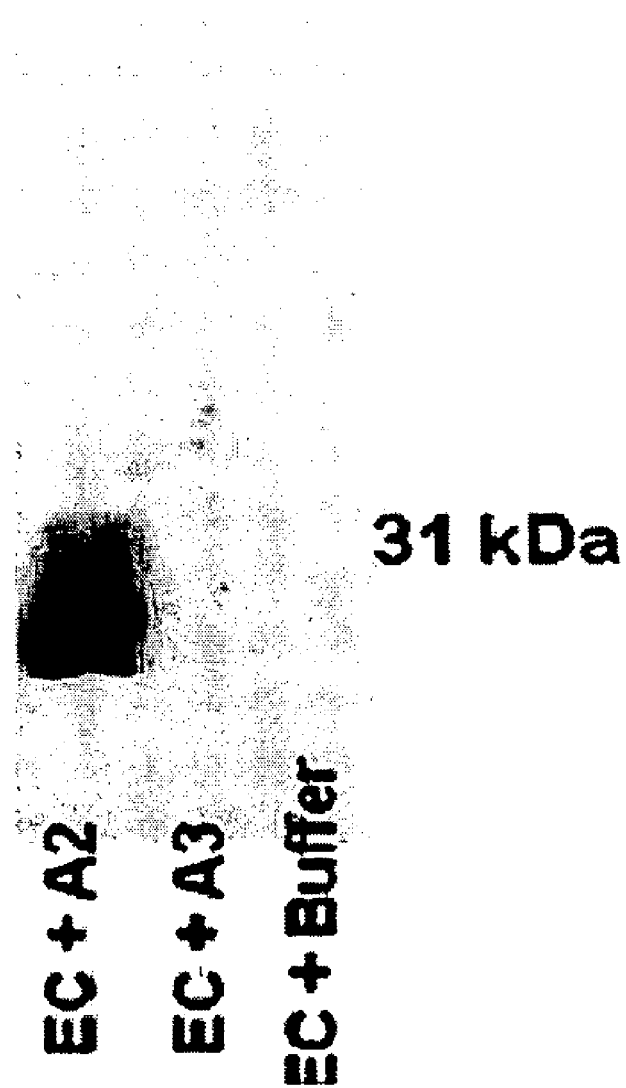
FIG. 25 shows HUVEC incubated with either A2 or A3 protein of buffer. The A2 protein was visualized using an anti-his tag antibody as binding to the endothelial cells, while A3 did not.
Figure 26:
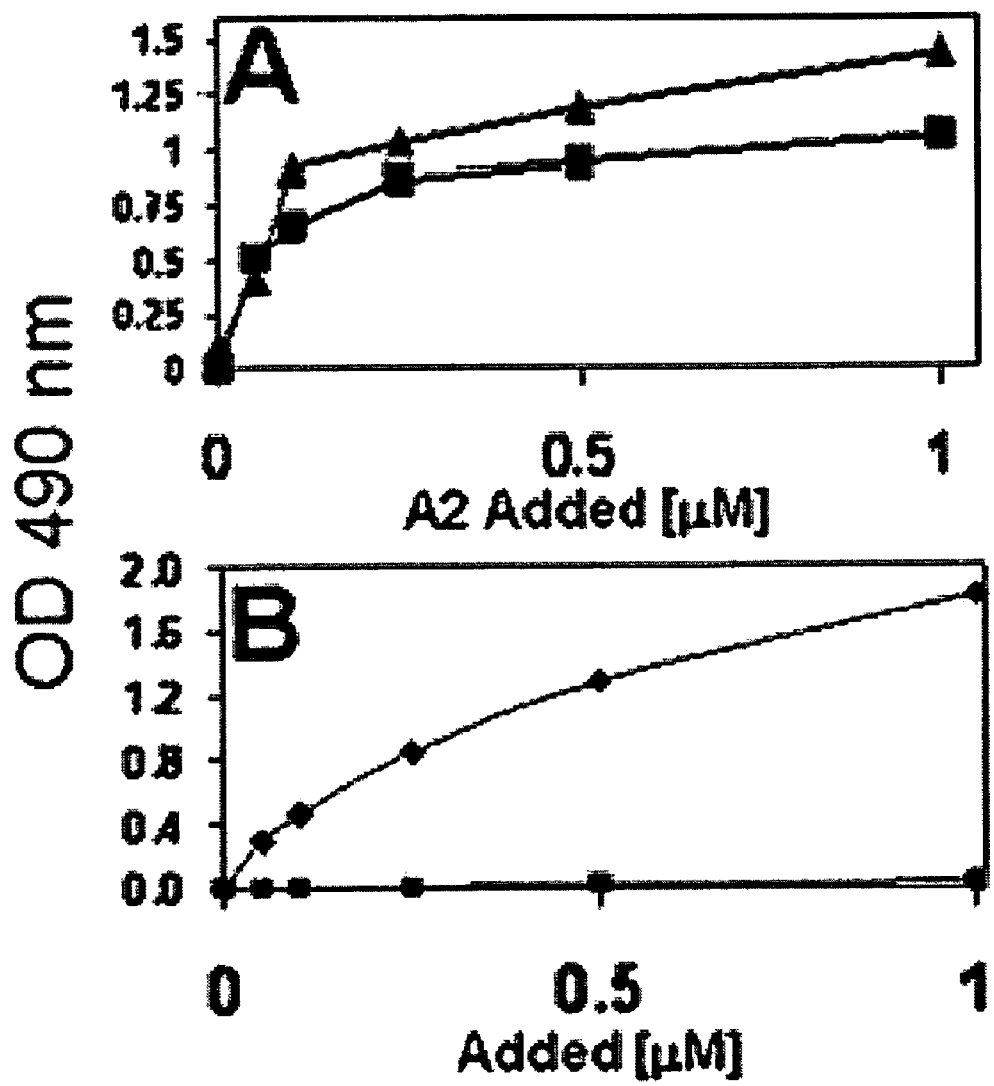
FIGS. 26A-26B show the interaction between the N-terminal A2 domain, and a A2 domain peptide and recombinant human vimentin.

The inventor has observed that the isolated form of the A2 domain of VWF led to a complete recovery of the LPS-treated mice with 100% survival compared with LPS only (18%). This beneficial effect observed from the A2 protein indicates that the protein works by interacting with endothelial cells (EC), counteracting some of the effects induced by EC activation, in specific embodiments. The inventors have demonstrated that the A2 polypeptide binds to EC (FIG. 25). HUVEC were incubated with either A2 or A3 protein (80 μg/ml) or buffer for 4 hours at 37° C. Cells were rinsed with PBS, scraped and centrifuged. The pellet was analyzed by Western Blot. Unlike the A3, the A2 protein was clearly visualized using Anti-his tag antibody (FIG. 25). Subsequently, a colloidal blue staining of protein immunoprecipitated from human umbilical vein endothelial cell (HUVEC) lysate, using A2 protein and anti-A2 antibody beads, revealed a prominent protein band of 52 kDa in molecular mass under reduced conditions. The band was excised for mass spectrometry (MS) analysis, and identified as vimentin. This result was reproduced three times using different batches of HUVECs.

FIG. 25A-26B demonstrate the specific binding activity between vimentin and the A2 polypeptide. The interaction between the A2 and recombinant human vimentin was analyzed by testing the binding of the purified A2 domain polypeptide to immobilized vimentin visualized by two different antibodies: Anti-A2 (triangles) or VP-1 (squares) (FIG. 25A), and the biding of the A2 G1481-Y1605 (SEQ ID NO:2) (diamond) or A2 M1606-R1668 (squares) fragments to immobilized vimentin (FIG. 25B). Increasing fragments of each polypeptide were incubated with immobilized vimentin. Bound A2 protein was determined by ELISA. Bound fragments were detected using VP-1 or anti-his tag antibody. Both graphs depict the specific binding after being subtracted from non-specific binding.

Example 17

Characterization of the A2-VIMENTIN Interaction

The inventor has observed that the A2 domain of VWF interacts with vimentin. Characterization of the A2 to vimentin interaction is further studied to map the vimentin binding site in the A2 domain. This demonstrates which amino acid residues in the A2 domain form part of the contact site for vimentin. The preliminary data indicates that the binding site for vimentin is in SEQ ID NO:2 (FIG. 26B). To localize the binding site, synthetic peptides covering the complete sequence of SEQ ID NO:2 are screened. The peptides of 12 amino acid residues in length and overlapping by four residues are biotinylated in the C-terminal. These soluble peptides are analyzed for both the binding of these soluble peptides to immobilized vimentin and the binding of soluble vimentin to the biotinylated peptides captured by avidin-coated plates. The bound analytes are detected using NeutrAvidin-HRP conjugated for the peptides or monoclonal antibodies for vimentin. The resultant peptides with the strongest binding activity are subsequently tested for their capacity to inhibit the binding of soluble A2 polypeptide to immobilized vimentin. Once the sequence(s) with the highest binding and blocking activity are identified, potential amino acid residues are substituted by synthesizing the mutant peptide or introducing the mutation in either SEQ ID NO:2 or the whole A2 protein. The last two are expressed in bacteria and purified the same as wild type. The capacity of the resultant mutants to bind vimentin are tested using ELISA and SPR. The resultant mutants with a significantly decreased vimentin-binding affinity/function (<50% wild-type activity), demonstrate the role of the mutated residue in vimentin binding. Furthermore, the resultant peptides or sequences with binding activity for vimentin are also tested for their capacity of recuperating the LPS treated mice.

Example 18

Detection of Activated VWF in Circulation

As shown by the inventor, the A2 domain polypeptide can be used to distinguish between the activated and non-activated VWF. This property of the A2 domain polypeptide allows the direct detection of active VWF in plasma, making an immunosorbent assay suitable to analyze the presence of active VWF in the plasma of patients with pathologic conditions. This study demonstrates a method of using the A2 polypeptide to determine the levels of circulating active VWF in blood. The binding capacity of different concentrations of plasma VWF is assessed (VWF:Ag is quantified by using a commercial available ELISA kit): 0.10, 0.25, 0.50 and 0.75 μg/ml from healthy donors (n=40). Each diluted sample (total volume/well=75 μl) is tested with or without ristocetin (0.5 mg/ml) to examine the difference in the binding capacity within the same individual. The healthy plasma samples are tested in quadruplicate in ten separated studies to determine the interexperiment variation and the reference baseline value for the assay. Furthermore, the binding activity for normal pool plasma (NPP) from the 40 donors is evaluated to compare with the values obtained for each individual. A low and similar binding capacity is anticipated for the samples without ristocetin in all the testing samples. Parallel studies are performed by using the nanobody AU/VWFa-11, which has been recently used for the detection of activated VWF in plasma of patients characterized by spontaneous VWF-platelet interactions (Hulstein et al., 2005). Because of the unique property (recognizes active conformation of the A1 domain and blocks the binding of the A1 to GPIbα), it is anticipated that the A2 polypeptide detects a different conformation of the exposed or activated A1 domain in the multimeric plasma VWF, being more sensitive and/or specific, in certain embodiments. The use of this nanobody is to compare and validate the results obtained with the A2 polypeptide.

Plasma samples from patients with lacunar stroke are obtained to assess the levels of activated VWF in plasma using the assay with the A2 polypeptide and the nanobody.

Alternatively, to confirm the results, the binding activity of plasma VWF to GPIbα are assessed using immobilized fixed platelets as have been previously demonstrated (Martin et al., 2007) A fixed concentration of VWF (0.5-1.0 µg/ml) is mixed with increasing concentrations of ristocetin (0, 0.10, 0.25, 0.50, 0.75 and 1.0 mg/ml) and incubated into the wells coated with the fixed platelets. After incubation for one hour at 37° C., the wells are washed and the bound VWF is detected with anti-human antibody VWF as described (Martin et al., 2007). A higher binding activity is anticipated for most of the patients than each individual healthy donor and the NPP at the low concentration range of the ristocetin, corroborating the presence of activated VWF in circulation.

Exemplary Methods. Microtiter wells are coated overnight at 4° C. with either 5 µg/mL A2 polypeptide or nanobody in 65 mM sodium phosphate buffer, pH 6.5 (PB) or carbonate buffer pH 9.6, respectively. Wells are blocked with 3% (w/v) bovine serum albumin (BSA) in phosphate buffered saline, pH 7.4 (PBS). All samples are diluted in PBS to reach the proposed VWF concentration between 0.10 and 0.75 µg/ml. Wells are washed and incubated with the increasing concentrations of VWF in the absence or presence of ristocetin (0.5 mg/mL) (1 hour 37° C.). After washing, the bound VWF is detected with HRP-conjugated polyclonal anti-VWF. NPP is used as standard in every assay. As described for the nanobody, we will determine the ratio between the slope for the different plasma samples over the slope for NPP to designate it as the activation factor (Hulsein et al., 2005). The slope of the healthy plasma samples in the presence of ristocetin may represent the binding activity of the plasma samples from patients in the absence of ristocetin.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Aird, W. C. 2003. The role of the endothelium in severe sepsis and multiple organ dysfunction syndrome. Blood 101: 3765-3777.

Alexander, C. and Rietschel, E. T. 2001. Bacterial lipopolysaccharides and innate immunity. J. Endotoxin.Res. 7:167-202.

Andonegui, G., Kerfoot, S. M., McNagny, K., Ebbert, K. V. J., Patel, K. D., and Kubes, P. 2005. Platelets express functional Toll-like receptor-4. Blood 106:2417-2423.

Arya, M., Anvari, B., Romo, G. M., Cruz, M. A., Dong, J. F., McIntire, L. V., Moake, J. L., and Lopez, J. A. 2002. Ultralarge multimers of von Willebrand factor form spontaneous high-strength bonds with the platelet glycoprotein Ib-IX complex: studies using optical tweezers. Blood 99:3971-3977.

Beacham, D. A., Wise, R. J., Turci, S. M., and Handin, R. I. 1992. Selective inactivation of the Arg-Gly-Asp-Ser (RGDS) binding site in von Willebrand factor by site-directed mutagenesis. J. Biol. Chem. 267:3409-3415.

Bemardo, A., Ball, C., Nolasco, L., Moake, J. F., and Dong, J. F. 2004. Effects of inflammatory cytokines on the release and cleavage of the endothelial cell-derived ultralarge von Willebrand factor multimers under flow. Blood 104:100-106.

Bonthron, D. T., Handin, R. I., Kaufman, R. J., Wasley, L. C., Orr, E. C., Mitsock, L. M., Ewenstein, B., Loscalzo, J., Ginsburg, D., and Orkin, S.H.1986. Structure of pre-pro-von Willebrand factor and its expression in heterologous cells. Nature 324:270-273.

Cardaropoli, S., Silvagno, F., Morra, E., Pescarmona, G. P., and Todros, T. 2003. Infectious and inflammatory stimuli decrease endothelial nitric oxide synthase activity in vitro. J. Hypertens. 21:2103-2110.

Cerwinka, W. H., Cooper, D., Krieglstein, C. F., Feelisch, M., and Granger, D. N. 2002. Nitric oxide modulates endotoxin-induced platelet-endothelial cell adhesion in intestinal venules. Am. J Physiol Heart Circ.Physiol 282:H1111-H1117.

Chen, J. and Lopez, J. A. 2005. Interactions of platelets with subendothelium and endothelium. Microcirculation. 12:235-246.

Christophe, O., Obert, B., Meyer, D., and Girma, J. P. 1991. The binding domain of von Willebrand factor to sulfatides is distinct from those interacting with glycoprotein Ib, heparin, and collagen and resides between amino acid residues Leu 512 and Lys 673. Blood 78:2310-2317.

Copeland, S., Warren, H. S., Lowry, S. F., Calvano, S. E., and Remick, D. 2005. Acute inflammatory response to endotoxin in mice and humans. Clin.Diagn.Lab Immunol. 12:60-67.

Corral, J., Yelamos, J., Hernandez-Espinosa, D., Monreal, Y., Mota, R., Arcas, I., Minano, A., Parrilla, P., and Vicente, V. 2005. Role of lipopolysaccharide and cecal ligation and puncture on blood coagulation and inflammation in sensitive and resistant mice models. Am. J. Pathol. 166:1089-1098.

Cruz, M. A., Chen, J., Whitelock, J. L., Morales, L. D., and Lopez, J. A. 2005. The platelet glycoprotein Ib-von Willebrand factor interaction activates the collagen receptor alpha2beta1 to bind collagen: activation-dependent conformational change of the alpha2-I domain. Blood 105:1986-1991.

Cruz, M. A., Handin, R. I., and Wise, R. J. 1993. The interaction of the von Willebrand factor-A1 domain with platelet glycoprotein Ib/IX. The role of glycosylation and disulfide bonding in a monomeric recombinant A1 domain protein. J. Biol. Chem. 268:21238-21245.

Cruz, M. A., Whitelock, J., and Dong, J. F. 2003. Evaluation of ADAMTS-13 activity in plasma using recombinant von Willebrand Factor A2 domain polypeptide as substrate. Thromb Haemost 90:1204-1209.

Cruz, M. A., Yuan, H., Lee, J. R., Wise, R. J., and Handin, R. I. 1995. Interaction of the von Willebrand factor (vWF) with collagen. Localization of the primary collagen-binding site by analysis of recombinant vWF a domain polypeptides. J. Biol. Chem. 270:10822-10827.

Dauphinee, S. M. and Karsan, A. 2006. Lipopolysaccharide signaling in endothelial cells. Lab Invest 86:9-22.

Dixon, B. 2004. The role of microvascular thrombosis in sepsis. Anaesth.Intensive Care 32:619-629.

Dong, J. F., Moake, J. L., Nolasco, L., Bemardo, A., Arceneaux, W., Shrimpton, C. N., Schade, A. J., McIntire, L. V., Fujikawa, K., and Lopez, J. A. 2002. ADAMTS-13 rapidly cleaves newly secreted ultralarge von Willebrand factor multimers on the endothelial surface under flowing conditions. Blood 100:4033-4039.

Dong, J. F., Whitelock, J., Bernardo, A., Ball, C., and Cruz, M. A. 2004. Variations among normal individuals in the cleavage of endothelial-derived ultra-large von Willebrand factor under flow. J Thromb Haemost 2:1460-1466.

Dremsizov, T. T., Kellum, J. A., and Angus, D.C. 2004. Incidence and definition of sepsis and associated organ dysfunction. Int.J. Artif.Organs 27:352-359.

Endenburg, S. C., Hantgan, R. R., Lindeboom-Blokzijl, L., Lankhof, H., Jerome, W. G., Lewis, J. C., Sixma, J. J., and De Groot, P. G. 1995. On the role of von Willebrand factor in promoting platelet adhesion to fibrin in flowing blood. Blood 86:4158-4165.

Estavillo, D., Ritchie, A., Diacovo, T. G., and Cruz, M. A. 1999. Functional analysis of a recombinant glycoprotein Ia/IIa (Integrin α2β1) I domain that inhibits platelet adhesion to collagen and endothelial matrix under flow conditions. J. Biol. Chem. 274:35921-35926.

Feistritzer, C., Sturn, D. H., Kaneider, N. C., Djanani, A., and Wiedermann, C. J. 2003. Endothelial protein C receptor-dependent inhibition of human eosinophil chemotaxis by protein C. J. Allergy Clin.Immunol. 112:375-381

Frankel, S. K., Cosgrove, G. P., Cha, S. I., Cool, C. D., Wynes, M. W., Edelman, B. L., Brown, K. K., and Riches, D. W. 2006. TNF-alpha sensitizes normal and fibrotic human lung fibroblasts to Fas-induced apoptosis. Am. J. Respir. Cell Mol. Biol. 34:293-304.

Fujikawa, K., Suzuki, H., McMullen, B., and Chung, D. 2001. Purification of human von Willebrand factor-cleaving protease and its identification as a new member of the metalloproteinase family. Blood 98:1662-1666.

Furlan, M., Robles, R., and Lammle, B. 1996. Partial purification and characterization of a protease from human plasma cleaving von Willebrand factor to fragments produced by in vivo proteolysis. Blood 87:4223-4234.

G. Borthakur, M. A. Cruz, J. F. Dong, L. Mcintire, F. Li, J. A. López, and P. Thiagarajan. 2003. Sulfatides inhibit platelet adhesion to von Willebrand factor in flowing blood. Journal of Thrombosis and Haemostasis 1:1288-1295.

Gimbrone, M. A., Jr., Topper, J. N., Nagel, T., Anderson, K. R., and Garcia-Cardena, G. 2000. Endothelial dysfunction, hemodynamic forces, and atherogenesis. Ann.N.Y.Acad.Sci. 902:230-239.

Girma, J. P., Meyer, D., Verweij, C. L., Pannekoek, H., and Sixma, J. J. 1987. Structure-function relationship of human von Willebrand factor. Blood 70:605-611.

Guidet, B., Aegerter, P., Gauzit, R., Meshaka, P., and Dreyfuss, D. 2005. Incidence and impact of organ dysfunctions associated with sepsis. Chest 127:942-951.

Harkness J E and Wagner J E. 1989. Biology and Husbandry. In The biology and medicine of rabbits and rodents. Harkness J E and Wagner J E, editors. Lea & Febiger, Philadelphia. 372.

Hatakeyama, M., Imaizumi, T., Tamo, W., Yamashita, K., Yoshida, H., Fukuda, I., and Satoh, K. 2004. Heparin inhibits IFN-gamma-induced fractalkine/CX3CL1 expression in human endothelial cells. Inflammation 28:7-13.

Hoylaerts, M. F., Yamamoto, H., Nuyts, K., Vreys, I., Deckmyn, H., and Vermylen, J. 1997. von Willebrand factor binds to native collagen VI primarily via its A1 domain. Biochem.J. 324 (Pt 1):185-191.

Hulstein, J. J., De Groot, P. G., Silence, K., Veyradier, A., Fijnheer, R., and Lenting, P. J. 2005. A novel nanobody that detects the gain-of-function phenotype of von Willebrand factor in ADAMTS13 deficiency and von Willebrand disease type 2B. Blood 106:3035-3042.

Ivaska, J., Pallari, H. M., Nevo, J., and Eriksson, J. E. 2007. Novel functions of vimentin in cell adhesion, migration, and signaling. Exp.Cell Res. 313:2050-2062.

Iwaki, T., Cruz, D. T., Martin, J. A., and Castellino, F. J. 2005. A cardioprotective role for the endothelial protein C receptor in lipopolysaccharide-induced endotoxemia in the mouse. Blood 105:2364-2371.

Katayama, T., Ikeda, Y., Handa, M., Tamatani, T., Sakamoto, S., Ito, M., Ishimura, Y., and Suematsu, M. 2000. Immunoneutralization of glycoprotein Ibalpha attenuates endotoxin-induced interactions of platelets and leukocytes with rat venular endothelium in vivo. Circ.Res. 86:1031-1037.

Keuren, J. F., Baruch, D., Legendre, P., Denis, C. V., Lenting, P. J., Girma, J. P., and Lindhout, T. 2004. von Willebrand factor C1C2 domain is involved in platelet adhesion to polymerized fibrin at high shear rate. Blood 103:1741-1746.

Klein, J. B., Rane, M. J., Scherzer, J. A., Coxon, P. Y., Kettritz, R., Mathiesen, J. M., Buridi, A., and McLeish, K. R. 2000. Granulocyte-macrophage colony-stimulating factor delays neutrophil constitutive apoptosis through phosphoinositide 3-kinase and extracellular signal-regulated kinase pathways. J. Immunol. 164:4286-4291.

Kokame, K., Matsumoto, M., Fujimura, Y., and Miyata, T. 2004. VWF73, a region from D1596 to R1668 of von Willebrand factor, provides a minimal substrate for ADAMTS-13. Blood 103:607-612.

Koppelman, S. J., van Hoeij, M., Vink, T., Lankhof, H., Schiphorst, M. E., Damas, C., Vlot, A. J., Wise, R., Bouma, B. N., and Sixma, J. J. 1996. Requirements of von Willebrand factor to protect factor VIII from inactivation by activated protein C. Blood 87:2292-2300.

Kort, W. J., Hekking-Weijma, J. M., TenKate, M. T., Sorm, V., and VanStrik, R. 1998. A microchip implant system as a method to determine body temperature of terminally ill rats and mice. Lab Anim 32:260-269.

Lankhof, H., van Hoeij, M., Schiphorst, M. E., Bracke, M., Wu, Y. P., Ijsseldijk, M. J., Vink, T., De Groot, P. G., and Sixma, J. J. 1996. A3 domain is essential for interaction of von Willebrand factor with collagen type III. Thromb.Haemost. 75:950-958.

Lenting, P. J., Westein, E., Terraube, V., Ribba, A. S., Huizinga, E. G., Meyer, D., De Groot, P. G., and Denis, C. V. 2004. An experimental model to study the in vivo survival of von Willebrand factor. Basic aspects and application to the R1205H mutation. J. Biol. Chem. 279:12102-12109.

Li, W., Zheng, X., Gu, J., Hunter, J., Ferrell, G. L., Lupu, F., Esmon, N. L., and Esmon, C. T. 2005. Overexpressing endothelial cell protein C receptor alters the hemostatic balance and protects mice from endotoxin. J Thromb Haemost 3:1351-1359.

Loscalzo, J., Inbal, A., and Handin, R. I. 1986. von Willebrand protein facilitates platelet incorporation in polymerizing fibrin. J. Clin.Invest 78:1112-1119.

Mantovani, A., Bussolino, F., and Dejana, E. 1992. Cytokine regulation of endothelial cell function. FASEB J 6:2591-2599.

Martin, C., Morales, L. D., and Cruz, M. A. 2007. Purified A2 domain of VWF binds to the active conformation of VWF and blocks the interaction with platelet GPIbalpha. J Thromb Haemost. 5:1363-70.

Mazzucato, M., Spessotto, P., Masotti, A., De Appollonia, L., Cozzi, M. R., Yoshioka, A., Perris, R., Colombatti, A., and De Marco, L. 1999. Identification of domains responsible for von Willebrand factor type VI collagen interaction mediating platelet adhesion under high flow. J. Biol. Chem. 274:3033-3041.

Meisner, M. 2005. Biomarkers of sepsis: clinically useful? Curr.Opin.Crit. Care 11:473-480.

Moake, J. L. 2002. Thrombotic thrombocytopenic purpura: the systemic clumping "plague". Annu.Rev. Med. 53:75-88.

Morales, L. D., MARTIN, C., and Cruz, M. A. 2006. The interaction of von Willebrand factor-A1 domain with collagen: mutation G1324S (type 2M von Willebrand disease)

impairs the conformational change in A1 domain induced by collagen. Journal of Thrombosis and Haemostasis 4:417-425.

Motto, D. G., Chauhan, A. K., Zhu, G., Homeister, J., Lamb, C. B., Desch, K. C., Zhang, W., Tsai, H. M., Wagner, D. D., and Ginsburg, D. 2005. Shigatoxin triggers thrombotic thrombocytopenic purpura in genetically susceptible ADAMTS13-deficient mice. J. Clin.Invest 115:2752-2761.

Murugesan, G., Rani, M. R., Ransohoff, R. M., Marchant, R. E., and Kottke-Marchant, K. 2000. Endothelial cell expression of monocyte chemotactic protein-1, tissue factor, and thrombomodulin on hydrophilic plasma polymers. J. Biomed.Mater.Res. 49:396-408.

Nachman, R., Levine, R., and Jaffe, E. A. 1977. Synthesis of factor VIII antigen by cultured guinea pig megakaryocytes. J. Clin.Invest 60:914-921.

Nguyen, B., Tanious, F. A., and Wilson, W. D. 2007. Biosensor-surface plasmon resonance: quantitative analysis of small molecule-nucleic acid interactions. Methods 42:150-161.

O'Brien, J. M., Jr., Ali, N. A., and Abraham, E. 2005. Year in review in Critical Care, 2004: sepsis and multi-organ failure. Crit. Care 9:409-413.

Ono, T., Mimuro, J., Madoiwa, S., Soejima, K., Kashiwakura, Y., Ishiwata, A., Takano, K., Ohmori, T., and Sakata, Y. 2006. Severe secondary deficiency of von Willebrand factor-cleaving protease (ADAMTS13) in patients with sepsis-induced disseminated intravascular coagulation: its correlation with development of renal failure. Blood 107:528-534.

Perrault, C., Ajzenberg, N., Legendre, P., Rastegar-Lari, G., Meyer, D., Lopez, J. A., and Baruch, D. 1999. Modulation by heparin of the interaction of the A1 domain of Von Willebrand factor with glycoprotein Ib. Blood 94:4186-4194.

Peters, K., Unger, R. E., Brunner, J., and Kirkpatrick, C. J. 2003. Molecular basis of endothelial dysfunction in sepsis. Cardiovasc.Res. 60:49-57.

Pinsky, M. R. 2004. Dysregulation of the immune response in severe sepsis. Am. J. Med.Sci. 328:220-229.

Pober, J. S, and Cotran, R. S. 1990. Cytokines and endothelial cell biology. Physiol Rev. 70:427-451.

Reininger, A. J., Agneskirchner, J., Bode, P. A., Spannagl, M., and Wurzinger, L. J. 2000. c7E3 Fab inhibits low shear flow modulated platelet adhesion to endothelium and surface-absorbed fibrinogen by blocking platelet GP IIb/IIIa as well as endothelial vitronectin receptor—results from patients with acute myocardial infarction and healthy controls. Thromb Haemost 83:217-223.

Remington's Pharmaceutical Sciences, 18th Ed. Mack Printing Company, 1990.

Riedemann, N. C., Guo, R. F., and Ward, P. A. 2003. The enigma of sepsis. J. Clin.Invest 112:460-467.

Rumbaut, R. E., Bellera, R. V., Randhawa, J. K., Shrimpton, C. N., Dasgupta, S. K., Dong, J. F., and Burns, A. R. 2006. Endotoxin enhances microvascular thrombosis in mouse cremaster venules via a TLR4-dependent, neutrophil-independent mechanism. Am. J Physiol Heart Circ.Physiol 290:H1671-H1679.

Rumbaut, R. E., Randhawa, J. K., Smith, C. W., and Burns, A. R. 2004. Mouse cremaster venules are predisposed to light/dye-induced thrombosis independent of wall shear rate, CD18, ICAM-1, or P-selectin. Microcirculation. 11:239-247.

Schorer, A. E., Moldow, C. F., and Rick, M. E. 1987. Interleukin 1 or endotoxin increases the release of von Willebrand factor from human endothelial cells. Br.J. Haematol. 67:193-197.

Sobel, M., Soler, D. F., Kermode, J. C., and Harris, R. B. 1992. Localization and characterization of a heparin binding domain peptide of human von Willebrand factor. J. Biol. Chem. 267:8857-8862.

Soothill, J. S., Morton, D. B., and Ahmad, A. 1992. The HID50 (hypothermia-inducing dose 50): an alternative to the LD50 for measurement of bacterial virulence. Int.J. Exp.Pathol. 73:95-98.

Springer, T. A. 1994. Traffic signals for lymphocyte recirculation and leukocyte emigration: the multistep paradigm. Cell 76:301-314.

Sussman, I. I. and Rand, J.H.1982. Subendothelial deposition of von Willebrand's factor requires the presence of endothelial cells. J.Lab Clin.Med. 100:526-532.

Tetta, C., Fonsato, V., Ronco, C., and Camussi, G. 2005. Recent insights into the pathogenesis of severe sepsis. Crit. Care Resusc. 7:32-39.

Tsai, H. M. 1996. Physiologic cleavage of von Willebrand factor by a plasma protease is dependent on its conformation and requires calcium ion. Blood 87:4235-4244.

Turner, N., Nolasco, L., Tao, Z., Dong, J. F., and Moake, J. 2006. Human endothelial cells synthesize and release ADAMTS-13. J Thromb Haemost 4:1396-1404.

van Mourik, J. A., Romani, D. W., and Voorberg, J. 2002. Biogenesis and exocytosis of Weibel-Palade bodies. Histochem.Cell Biol. 117:113-122.

Vasudevan, S., Roberts, J. R., McClintock, R. A., Dent, J. A., Celikel, R., Ware, J., Varughese, K. I., and Ruggeri, Z. M. 2000. Modeling and functional analysis of the interaction between von Willebrand factor A1 domain and glycoprotein Ibalpha. J. Biol. Chem. 275:12763-12768.

Verweij, C. L., Diergaarde, P. J., Hart, M., and Pannekoek, H.1986. Full-length von Willebrand factor (vWF) cDNA encodes a highly repetitive protein considerably larger than the mature vWF subunit. EMBO J. 5:1839-1847.

Weglarz, L., Dzierzewicz, Z., Skop, B., Orchel, A., Parfiniewicz, B., Wisniowska, B., Swiatkowska, L., and Wilczok, T. 2003. *Desulfovibrio* desulfuricans lipopolysaccharides induce endothelial cell IL-6 and IL-8 secretion and E-selectin and VCAM-1 expression. Cell Mol. Biol.Lett. 8:991-1003.

Whitelock, J. L., Nolasco, L., Bernardo, A., Moake, J., Dong, J. F., and Cruz, M. A. 2004. ADAMTS-13 activity in plasma is rapidly measured by a new ELISA method that uses recombinant VWF-A2 domain as substrate. J Thromb Haemost 2:485-491.

Whittaker, C. A. and Hynes, R. O. 2002. Distribution and evolution of von Willebrand/integrin A domains: widely dispersed domains with roles in cell adhesion and elsewhere. Mol. Biol.Cell 13:3369-3387.

Wong, P. M., Chugn, S. W., and Sultzer, B. M. 2000. Genes, receptors, signals and responses to lipopolysaccharide endotoxin. Scand.J. Immunol. 51:123-127.

Zeuke, S., Ulmer, A. J., Kusumoto, S., Katus, H. A., and Heine, H.2002. TLR4-mediated inflammatory activation of human coronary artery endothelial cells by LPS. Cardiovasc.Res. 56:126-134.

Zheng, X., Chung, D., Takayama, T. K., Majerus, E. M., Sadler, J. E., and Fujikawa, K. 2001. Structure of von Willebrand factor-cleaving protease (ADAMTS13), a metalloprotease involved in thrombotic thrombocytopenic purpura. J. Biol. Chem. 276:41059-41063.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

---

What is claimed is:

1. A method of treating one or more of sepsis, thrombosis, and systemic inflammatory reaction syndrome (SIRS) in an individual, comprising delivering to the individual a therapeutically effective amount of an A2 domain of von Willebrand factor, or a functionally active fragment of said A2 domain, wherein said A2 domain of von Willebrand factor or said functionally active fragment of said A2 domain is further defined as a polypeptide comprising at least 75% identity, at least 80% identity, at least 85% identity, at least 90% identity, at least 95% identity, at least 97% identity, at least 98% identity, or at least 99% identity to SEQ ID NO:1, SEQ ID NO:2, SEQ ID NO:19, SEQ ID NO:20, SEQ ID NO:21, SEQ ID NO:22, SEQ ID NO:23, SEQ ID NO:26, SEQ ID NO:27, SEQ ID NO:28, or SEQ ID NO:30 that inhibits ristocetin-induced platelet agglutination, shear-induced platelet aggregation, and platelet adhesion to collagen under flow conditions.

2. The method of claim 1, wherein the A2 domain is delivered to the individual as a polypeptide.

3. The method of claim 2, wherein the polypeptide is comprised in a carrier.

4. The method of claim 3, wherein the carrier comprises lipid.

5. The method of claim 3, wherein the carrier comprises liposome.

6. The method of claim 1, wherein the individual is a patient in a hospital.

7. The method of claim 1, wherein the individual has undergone surgery, is undergoing surgery, or will undergo surgery.

8. The method of claim 1, wherein the A2 domain is delivered intravenously.

9. The method of claim 1, further comprising delivering one or more antibiotics to the individual.

* * * * *